United States Patent
Kirn et al.

(10) Patent No.: US 11,685,904 B2
(45) Date of Patent: Jun. 27, 2023

(54) RECOMBINANT VACCINIA VIRUS AND METHODS OF USE THEREOF

(71) Applicant: Ignite Immunotherapy, Inc., New York, NY (US)

(72) Inventors: David H. Kirn, Mill Valley, CA (US); Liliana Maruri Avidal, Oakland, CA (US); Prajit Limsirichai, Washington, DC (US)

(73) Assignee: Ignite Immunotherapy, Inc., New York, NY (US)

( * ) Notice: Subject to any disclaimer, the term of this patent is extended or adjusted under 35 U.S.C. 154(b) by 547 days.

(21) Appl. No.: 16/786,134

(22) Filed: Feb. 10, 2020

(65) Prior Publication Data
US 2020/0263145 A1     Aug. 20, 2020

Related U.S. Application Data

(60) Provisional application No. 62/885,487, filed on Aug. 12, 2019, provisional application No. 62/805,794, filed on Feb. 14, 2019.

(51) Int. Cl.
| | |
|---|---|
| *C12N 7/00* | (2006.01) |
| *A61K 31/522* | (2006.01) |
| *A61K 35/768* | (2015.01) |
| *C12N 9/12* | (2006.01) |

(52) U.S. Cl.
CPC .............. *C12N 7/00* (2013.01); *A61K 31/522* (2013.01); *A61K 35/768* (2013.01); *C12N 9/1211* (2013.01); *C12Y 207/01021* (2013.01); *C12N 2710/24122* (2013.01); *C12N 2710/24132* (2013.01)

(58) Field of Classification Search
CPC .......... A61P 35/00; A61P 35/04; A61P 43/00; A61P 29/00; A61P 37/00; A61P 37/02; A61P 31/12; A61P 9/00; A61P 11/00; C12N 2710/24143; C12N 15/74; C12N 15/86; C12N 2710/24121; C12N 2710/24134; C12N 2710/24161; C12N 2710/24122; C12N 15/70; C12N 1/20; C12N 1/36; C12N 2502/99; C12N 2510/00; C12N 2710/00033; C12N 2710/10051; C12N 2710/16051; C12N 2710/24151; C12N 2720/12051; C12N 2750/10022; C12N 2750/10033; C12N 2760/16134; C12N 2760/18051; C12N 2760/20051; C12N 2760/20251; C12N 2770/20022; C12N 2770/20034; C12N 2770/32051; C12N 2770/36051; C12N 2710/24132; C12N 9/1211; A61K 35/768; A61K 39/39558; C12Y 207/01021
See application file for complete search history.

(56) References Cited

U.S. PATENT DOCUMENTS

| | | | | |
|---|---|---|---|---|
| 7,888,091 B2* | 2/2011 | Black | ..... | A61P 35/00 435/320.1 |
| 7,888,114 B2* | 2/2011 | Black | ..... | A61P 37/00 435/320.1 |
| 8,163,528 B2* | 4/2012 | Black | ..... | A61P 33/00 435/320.1 |
| 8,236,541 B2* | 8/2012 | Black | ..... | A61P 31/18 435/320.1 |
| 8,323,959 B2* | 12/2012 | Szalay | ..... | C12N 7/00 536/23.7 |
| 8,329,164 B2 | 12/2012 | David et al. | | |
| 8,986,674 B2 | 3/2015 | David et al. | | |
| 2012/0276053 A1 | 11/2012 | Kern | | |
| 2014/0288163 A1 | 9/2014 | Levy et al. | | |
| 2016/0235793 A1 | 8/2016 | Thorne | | |

FOREIGN PATENT DOCUMENTS

| | | |
|---|---|---|
| WO | 2005/047458 | 5/2005 |
| WO | WO 2014/153258 | 9/2014 |
| WO | WO 2017/037523 | 3/2017 |

OTHER PUBLICATIONS

Liu et al. Nature Communications, published on May 2017, 8:14754 | DOI: 10.1038/ncomms14754 | www.nature.com/naturecommunications pp. 1-12.*
Wildner et al. Cancer Research 1999, vol. 59 (2), pp. 410-413.*
U.S. Appl. No. 16/738,535, filed Jan. 9, 2020.
Culver, K., et al., "In vivo gene transfer with retroviral vector-producer cells for treatment of experimental brain tumors", Science, vol. 256, 1992, pp. 1550-1552.
Panicali, D., et al., "Construction of poxviruses as cloning vectors: insertion of the thymidine kinase gene from herpes simplex virus into the DNA of infectious vaccinia virus", Proceedings of the National Academy of Sciences, vol. 79, No. 16, 1982, pp. 4927-4931.
International Search Report, PCT/IB2020/051025, dated Apr. 5, 2020.
Fillat, C., et al., "Suicide Gene Therapy Mediated by the Herpes Simplex Virus Thymidine Kinase Gene / Ganciclovir System: Fifteen Years of Application", Current Gene Therapy, 2003, pp. 13-26, vol. 3, Issue 1.

(Continued)

*Primary Examiner* — Bao Q Li
(74) *Attorney, Agent, or Firm* — Austin W. Zhang

(57) ABSTRACT

The present disclosure provides a replication-competent, recombinant oncolytic vaccinia virus, compositions comprising the vaccinia virus, and use of the vaccinia virus or composition for inducing oncolysis in an individual having a tumor.

15 Claims, 18 Drawing Sheets
Specification includes a Sequence Listing.

(56) References Cited

OTHER PUBLICATIONS

Mejias-Perez, E., et al., "Development of a Safe and Effective Vaccinia Virus Oncolytic Vector WR-Δ4 with a Set of Gene Deletions on Several Viral Pathways", Mol. Ther. Oncolytics, 2018, pp. 1-40, vol. 8, Issue 27.

Blasco, R., et al., "Dissociation of Progeny Vaccinia Virus from the Cell Membrane is Regulated by a Viral Envelope Glycoprotein: Effect of a Point Mutation in the Lectin Homology Domain of the A34R Gene", J. Virology,1993, pp. 3319-3325, vol. 67, No. 6.

Thirunavukarasu, P., et al., "A Rationally Designed A34R Mutant Oncolytic Poxvirus: Improved Efficacy in Peritoneal Carcinomatosis", Mol. Ther., 2013, pp. 1024-1033, vol. 21, No. 5.

Bakhtiar Ul Islam, S M., et al, "Engineering and Characterization of Oncolytic Vaccinia Virus Expressing Truncated Herpes Simplex Virus Thymidine Kinase", Cancers, 2020,12, 228; doi:10.3390/cancers12010228.

\* cited by examiner

FIG. 1

FIG. 4A
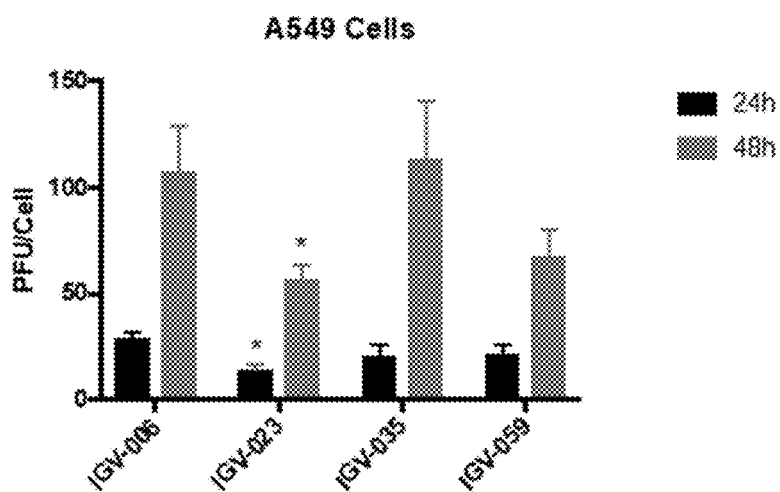
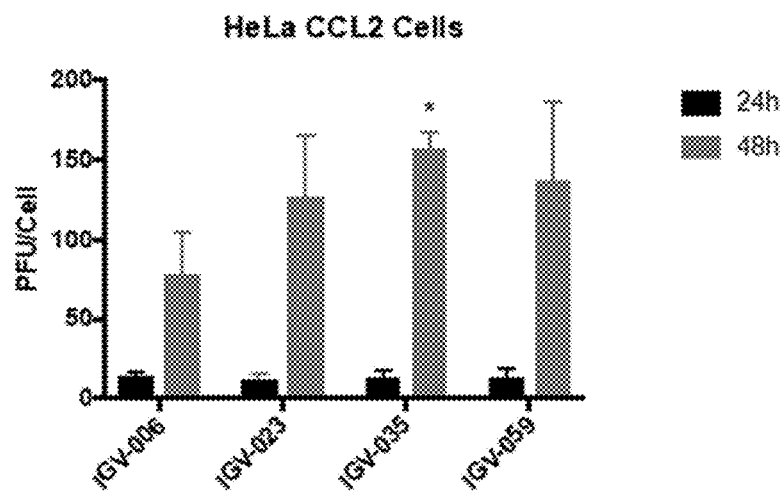
FIG. 4B
FIG. 4C
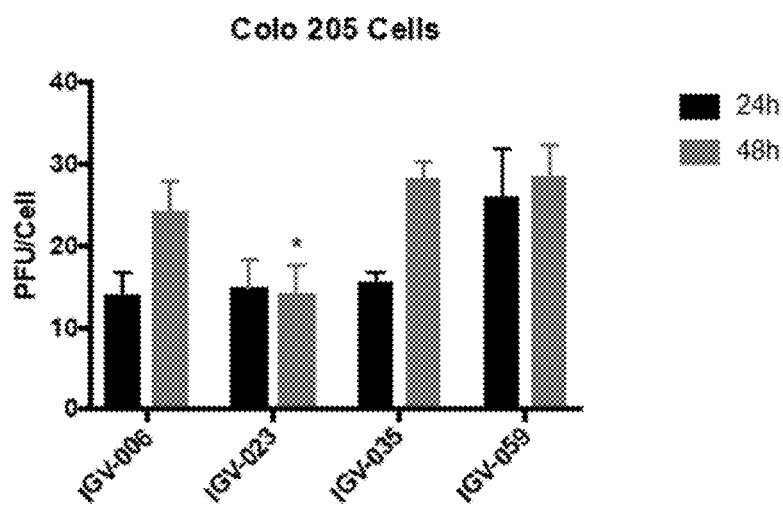

RECOMBINANT VACCINIA VIRUS AND METHODS OF USE THEREOF

CROSS REFERENCE TO RELATED APPLICATIONS

The present application claims the benefit of priority to U.S. Provisional Application No. 62/885,487, filed on Aug. 12, 2019, and to U.S. Provisional Application No. 62/805,794, filed on Feb. 14, 2019, each of which is incorporated by reference herein in their entireties.

INCORPORATION BY REFERENCE OF SEQUENCE LISTING PROVIDED AS A TEXT FILE

A Sequence Listing is provided herewith as a text file, "PC40317_SequenceListing_ST25.txt" created on Jan. 24, 2020 and having a size of 21 KB. The contents of the text file are incorporated by reference herein in their entirety.

INTRODUCTION

Oncolytic viruses (OVs) are viruses that selectively replicate in cancer cells. Live replicating OVs have been tested in clinical trials in a variety of human cancers. OVs can induce anti-tumor immune responses, as well as direct lysis of tumor cells. Common OVs include attenuated strains of Herpes Simplex Virus (HSV), Adenovirus (Ad), Measles Virus (MV), Coxsackie virus (CV), Vesicular Stomatitis Virus (VSV), and Vaccinia Virus (VV).

Vaccinia virus replicates in the cytoplasm of a host cell. The large vaccinia virus genome codes for various enzymes and proteins used for viral DNA replication. During replication, vaccinia produces several infectious forms which differ in their outer membranes: the intracellular mature virion (IMV), the intracellular enveloped virion (IEV), the cell-associated enveloped virion (CEV) and the extracellular enveloped virion (EEV). IMV is the most abundant infectious form and is thought to be responsible for spread between hosts; the CEV is believed to play a role in cell-to-cell spread; and the EEV is thought to be important for long range dissemination within the host organism.

SUMMARY

The present disclosure provides a replication-competent, recombinant oncolytic vaccinia virus comprising a nucleotide sequence encoding a heterologous thymidine kinase polypeptide; and compositions comprising the replication-competent, recombinant oncolytic vaccinia virus. The present disclosure provides methods of inducing oncolysis in an individual having a tumor, the methods comprising administering to the individual an effective amount of a replication-competent, recombinant oncolytic vaccinia virus of the present disclosure or a composition of the present disclosure.

BRIEF DESCRIPTION OF THE DRAWINGS

FIG. 1 provides an alignment of amino acid sequences of wild-type herpes simplex virus (HSV) thymidine kinase (TK) (HSV-TK) (SEQ ID NO:1) and HSV-TK variants (SEQ ID NO:2, 3, 4).

FIGS. 4A-4F depict the effect of HSV-TK expression on vaccinia virus replication in representative human cancer cell lines and normal primary human cells.

DEFINITIONS

Figure 2:
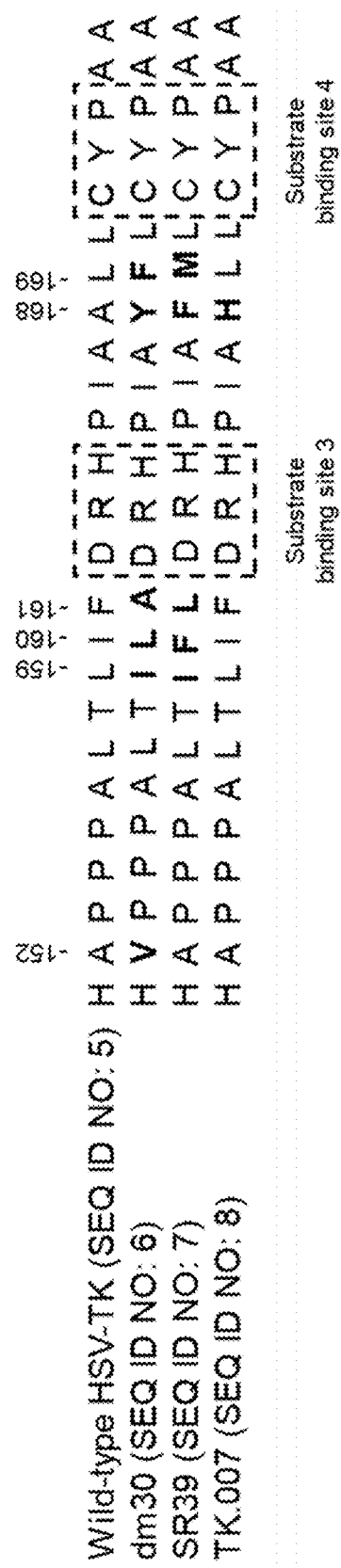
FIG. 2 provides an alignment of amino acids 151-175 of HSV-TK (SEQ ID NO:5) and corresponding regions of HSV-TK variants (SEQ ID NO:6, 7, 8).

As used herein, an "oncolytic" vaccinia virus is a vaccinia virus that preferentially infects and kills cancer cells, compared to normal (non-cancerous) cells.

"Heterologous," as used herein, means a nucleotide or polypeptide sequence that is not found in the native nucleic acid or protein of a given organism, respectively. For example, in the context of a recombinant vaccinia virus of the present disclosure, a nucleic acid comprising a nucleotide sequence encoding a "heterologous" thymidine kinase (TK) (where the heterologous TK is a variant (TKv) polypeptide) is a nucleic acid that is not found naturally in vaccinia virus, i.e., the encoded TKv polypeptide is not encoded by naturally-occurring vaccinia virus.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (e.g., rats, mice), lagomorphs (e.g., rabbits), non-human primates, humans, canines, felines, ungulates (e.g., equines, bovines, ovines, porcines, caprines), etc.

A "therapeutically effective amount" or "efficacious amount" refers to the amount of an agent (e.g., a replication-competent, recombinant oncolytic vaccinia virus of the present disclosure), or combined amounts of two agents (e.g., a replication-competent, recombinant oncolytic vaccinia virus of the present disclosure and a second therapeutic agent), that, when administered to a mammal or other subject for treating a disease, is sufficient to effect such treatment for the disease. The "therapeutically effective amount" will vary depending on the agent(s), the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a vaccinia virus" includes a plurality of such vaccinia viruses and reference to "the variant thymidine kinase polypeptide" includes reference to one or more variant thymidine kinase polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a replication-competent, recombinant oncolytic vaccinia virus comprising a nucleotide sequence encoding a heterologous thymidine kinase (TK) polypeptide, wherein the heterologous TK polypeptide is a variant of herpes simplex virus (HSV) TK; and compositions comprising the replication-competent, recombinant oncolytic vaccinia virus. The present disclosure provides methods of inducing oncolysis in an individual having a tumor, the methods comprising administering to the individual an effective amount of a replication-competent, recombinant oncolytic vaccinia virus of the present disclosure or a composition of the present disclosure.

Oncolytic Vaccinia Virus

The present disclosure provides a replication-competent, recombinant oncolytic vaccinia virus comprising a nucleotide sequence encoding a heterologous TK polypeptide, where the heterologous TK polypeptide is a variant of a herpes simplex virus TK (HSV-TK) polypeptide. A heterologous TK polypeptide that is a variant of wild-type HSV-TK is referred to herein as an "HSV-TKv polypeptide," "TKv polypeptide," or simply "TKv."

A replication-competent, recombinant oncolytic vaccinia virus of the present disclosure, when present in a host cell, does not substantially provide for production of the vaccinia virus thymidine kinase or otherwise lacks the vaccinia virus thymidine kinase activity. A virus that lacks endogenous vaccinia virus thymidine kinase activity may be referred to as being "thymidine kinase negative," "TK negative," "thymidine kinase deficient," or "TK deficient." In some cases, the virus can be rendered TK deficient by insertion of another gene in the TK locus. In some cases, a recombinant vaccinia virus of the present disclosure may be rendered TK deficient by deletion of a portion or the entire TK coding region. For example, in some cases, a replication-competent, recombinant oncolytic vaccinia virus of the present disclosure comprises a J2R deletion. See, e.g., Mejía-Perez et al. (2018) *Mol. Ther. Oncolytics* 8:27. In some cases, a replication-competent, recombinant oncolytic vaccinia virus of the present disclosure comprises an insertion into the J2R region, thereby resulting in reduced or no vaccinia virus TK activity. In wild-type vaccinia virus, the J2R region encodes vaccinia virus TK. In some instances, the TKv-encoding nucleotide sequence replaces all or a part of the vaccinia virus TK-encoding nucleotide sequence. For example, in some cases, the heterologous TK polypeptide-encoding nucleotide sequence replaces at least 10%, at least 15%, at least 20%, at least 25%, at least 30%, at least 40%, at least 50%, at least 75%, or 100%, of the J2R region of vaccinia virus. In some cases, replication-competent, recombinant oncolytic vaccinia virus of the present disclosure comprises a modification such that transcription of the endogenous (vaccinia virus-encoded) TK-encoding gene is reduced or eliminated. For example, in some cases, transcription of the endogenous (vaccinia virus-encoded) TK-encoding gene is reduced by at least 50%, at least 60%, at least 70%, at least 80%, at least 90%, or more than 90%, or 100% compared to the transcription of the endogenous (vaccinia virus-encoded) TK-encoding gene without the modification.

In some cases, replication of the replication-competent, recombinant oncolytic vaccinia virus is inhibited with ganciclovir at a lower concentration than the concentration at which replication of a replication-competent, recombinant oncolytic vaccinia virus encoding a wild-type HSV-TK polypeptide is inhibited. For example, the ganciclovir inhibitory concentration at which replication of a replication-competent, recombinant oncolytic vaccinia virus of the present disclosure that encodes a variant of wild-type HSV-TK is inhibited by 50% of maximum ($IC_{50}$) is at least 10%, at least 15%, at least 20%, at least 25%, at least 30%, at least 40%, at least 50%, at least 60%, at least 70%, or at least 80% lower than the ganciclovir $IC_{50}$ for inhibition of replication of a replication-competent, recombinant oncolytic vaccinia virus encoding a wild-type HSV-TK polypeptide. In some cases, said $IC_{50}$ is determined in vitro using HeLa cells in the conditions disclosed at Example 1 (sensitivity of viral replication to ganciclovir).

Heterologous TK Polypeptides

As noted above, a replication-competent, recombinant oncolytic vaccinia virus of the present disclosure comprises a nucleotide sequence encoding a TKv polypeptide. The TKv polypeptide is in some cases a type I TK polypeptide. In some cases, a TK polypeptide is capable of catalyzing phosphorylation of deoxyguanosine (dG) to generate dG monophosphate. In some cases, the TK polypeptide that is capable of catalyzing phosphorylation of both deoxythymidine (dT) and deoxyguanosine (dG) to generate dT monophosphate and dG monophosphate, respectively.

A heterologous TK polypeptide encoded by a nucleotide sequence present in a replication-competent, recombinant oncolytic vaccinia virus of the present disclosure is a variant of wild-type HSV-TK, where the TKv polypeptide comprises one or more amino acid substitutions relative to wild-type HSV-TK (SEQ ID NO:1). Thus, e.g., a TKv polypeptide encoded by a nucleotide sequence present in a replication-competent, recombinant oncolytic vaccinia virus of the present disclosure comprises from 1 to 40 amino acid substitutions relative to wild-type HSV-TK. For example, a TKv polypeptide encoded by a nucleotide sequence present in a replication-competent, recombinant oncolytic vaccinia virus of the present disclosure comprises from 1 to 5, from 5 to 10, from 10 to 15, from 15 to 20, from 20 to 25, from 25 to 30, from 30 to 35, or from 35 to 40, amino acid substitutions relative to wild-type HSV-TK (SEQ ID NO:1).

The amino acid sequence of a large number of human wild-type HSV TKs from different HSV strains or isolates is known in the art. For example, the HSV-TK amino acid sequence is available in GenBank for strain SC16 (Accession No. P06479; also set forth in SEQ ID NO:1), strain HFEM (Accession No. P08333), strain KOS (Accession No. P17402), strain 17 (Accession No. P03176), and strain CL101 (Accession No. P06478). These sequences exhibit a high degree of homology, sharing at least 98.67% sequence identity with the sequence of SEQ ID NO:1. In view of the high degree of homology of the wild-type HSV-TK sequences, a HSV-TK variant that may be included in the recombinant vaccinia virus of the present disclosure may be constructed from any of the wild-type HSV-TK, known now or discovered in the future, by introducing the specific mutations described herein with reference to the sequence of SEQ ID NO:1.

A heterologous TK polypeptide present in a replication-competent, recombinant oncolytic vaccinia virus of the present disclosure can comprise an amino acid sequence having at least 80%, at least 85%, at least 90%, at least 95%, at least 98%, or at least 99%, amino acid sequence identity to the following wild-type HSV-TK amino acid sequence:

```
                                            (SEQ ID NO: 1)
MASYPGHQHASAFDQAARSRGHSNRRTALRPRRQQEATEVRPEQKMPTL

LRVYIDGPHGMGKTTTTQLLVALGSRDDIVYVPEPMTYWRVLGASETIA

NIYTTQHRLDQGEISAGDAAVVMTSAQITMGMPYAVTDAVLAPHIGGEA

GSSHAPPPALTLIFDRHPIAALLCYPAARYLMGSMTPQAVLAFVALIPP

TLPGTNIVLGALPEDRHIDRLAKRQRPGERLDLAMLAAIRRVYGLLANT

VRYLQGGGSWREDWGQLSGTAVPPQGAEPQSNAGPRPHIGDTLFTLFRA

PELLAPNGDLYNVFAWALDVLAKRLRPMHVFILDYDQSPAGCRDALLQL

TSGMIQTHVTTPGSIPTICDLARTFAREMGEAN,
``` where the TKv polypeptide comprises one or more amino acid substitutions relative to SEQ ID NO:1.

In some cases, nucleotide sequences encoding a heterologous TK polypeptide present in a replication competent, recombinant oncolytic vaccinia virus of the present disclosure can comprise a nucleotide sequence encoding at least 80%, at least 85%, at least 90%, at least 95%, at least 98%, or at least 99%, nucleotide sequence identity to the following wild-type HSV-TK nucleotide sequence:

```
                                           (SEQ ID NO: 10)
ATGGCCTCATATCCTGGTCATCAACACGCTAGTGCCTTCGACCAGGCG

GCGAGATCTCGAGGACATTCGAATAGACGAACAGCATTACGTCCACGA

AGACAACAGGAGGCGACAGAGGTCCGACCTGAACAGAAAATGCCTACA

CTTTTGCGAGTCTACATAGATGGTCCCCACGGAATGGGTAAAACTACC

ACTACCCAGTTGTTAGTCGCCTTAGGTTCTCGAGACGATATTGTCTAT

GTGCCCGAGCCCATGACTTACTGGCGAGTCCTAGGTGCATCGGAAACG

ATAGCGAACATCTATACGACACAGCATCGTTTGGACCAGGGAGAGATC

TCGGCCGGTGACGCAGCAGTCGTAATGACAAGTGCTCAAATTACGATG

GGTATGCCTTATGCGGTAACTGACGCAGTCTTGGCTCCGCATATCGGT

GGAGAGGCCGGATCGTCACACGCTCCCCCTCCAGCGTTAACTCTAATT
```

-continued

```
TTCGACCGACACCCAATTGCTGCGCTTTTATGTTACCCCGCGGCAAGA

TATTTAATGGGATCAATGACCCCGCAAGCTGTGTTAGCTTTTGTGGCA

TTGATTCCGCCAACCTTACCTGGAACGAATATAGTCCTTGGTGCATTA

CCAGAGGATAGACATATTGACAGACTTGCTAAGCGACAGCGACCGGGA

GAGAGATTGGACTTAGCAATGTTGGCGGCCATAAGACGAGTCTACGGA

CTTTTGGCTAATACGGTTAGATATTTGCAAGGAGGAGGAAGTTGGCGA

GAGGATTGGGGTCAGTTGTCTGGTACTGCTGTGCCTCCGCAGGGAGCT

GAGCCTCAGTCTAACGCTGGACCACGACCTCACATCGGAGATACGTTA

TTTACCCTATTCCGTGCGCCGGAATTATTAGCACCCAACGGTGATCTA

ATACAACGTCTTTGCGTGGGCCTTGGACGTACTTGCAAAGCGTCTACG

TCCTATGCATGTCTTCATCCTAGACTACGACCAGTCGCCCGCGGGATG

TCGAGACGCCTTGCTACAGTTGACCTCGGGAATGATTCAGACACACGT

TCACCACCCCGGGATCCATACCCACTATTTGTGACTTAGCAAGAACAT

TTGCCCGAGAAATGGGTGAAGCTAAC.
```

This sequence is codon optimized for vaccinia virus. In some cases, the heterologous TK polypeptide comprises one or more amino acid substitutions relative to the wild-type HSV-TK amino acid sequence (set forth above; SEQ ID NO:1). For example, in some cases, the heterologous TK polypeptide comprises a substitution of one or more of L159, I160, F161, A168, and L169.

In some cases, the heterologous TK polypeptide comprises an amino acid sequence having at least 80%, at least 85%, at least 90%, at least 95%, at least 98%, or at least 99%, amino acid sequence identity to the wild-type HSV-TK amino acid sequence set forth above (SEQ ID NO:1), but has a substitution at L159, i.e., amino acid 159 is other than Leu. For example, amino acid 159 is Gly, Ala, Val, Ile, Pro, Phe, Tyr, Trp, Ser, Thr, Cys, Met, Gln, Asn, Lys, Arg, His, Asp, or Glu. In some cases, the substitution is an L1591 substitution. In some cases, the substitution is an L159A substitution. In some cases, the substitution is an L159V substitution.

In some cases, the heterologous TK polypeptide comprises an amino acid sequence having at least 80%, at least 85%, at least 90%, at least 95%, at least 98%, or at least 99%, amino acid sequence identity to the wild-type HSV-TK amino acid sequence set forth above (SEQ ID NO:1), but has a substitution at I160, i.e., amino acid 160 is other than Ile. For example, amino acid 160 is Gly, Ala, Val, Leu, Pro, Phe, Tyr, Trp, Ser, Thr, Cys, Met, Gln, Asn, Lys, Arg, His, Asp, or Glu. In some cases, the substitution is an I160L substitution. In some cases, the substitution is an I160V substitution. In some cases, the substitution is an I160A substitution. In some cases, the substitution is an I160F substitution. In some cases, the substitution is an I160Y substitution. In some cases, the substitution is an I160W substitution.

In some cases, the heterologous TK polypeptide comprises an amino acid sequence having at least 80%, at least 85%, at least 90%, at least 95%, at least 98%, or at least 99%, amino acid sequence identity to the wild-type HSV-TK amino acid sequence set forth above (SEQ ID NO:1), but has a substitution at F161, i.e., amino acid 161 is other than Phe. For example, amino acid 161 is Gly, Ala, Val, Leu, Ile, Pro, Tyr, Trp, Ser, Thr, Cys, Met, Gln, Asn, Lys, Arg, His, Asp, or Glu. In some cases, the substitution is an F161A substitution. In some cases, the substitution is an F161L substitution. In some cases, the substitution is an F161V substitution. In some cases, the substitution is an F161I substitution.

In some cases, the heterologous TK polypeptide comprises an amino acid sequence having at least 80%, at least 85%, at least 90%, at least 95%, at least 98%, or at least 99%, amino acid sequence identity to the wild-type HSV-TK amino acid sequence set forth above (SEQ ID NO:1), but has a substitution at A168, i.e., amino acid 168 is other than Ala. For example, amino acid 168 is Gly, Val, Leu, Ile, Pro, Phe, Tyr, Trp, Ser, Thr, Cys, Met, Gln, Asn, Lys, Arg, His, Asp, or Glu. In some cases, the substitution is A168H. In some cases, the substitution is A168R. In some cases, the substitution is A168K. In some cases, the substitution is A168Y. In some cases, the substitution is A168F. In some cases, the substitution is A168W. In some cases, the TKv polypeptide does not include any other substitutions other than a substitution of A168.

In some cases, the heterologous TK polypeptide comprises an amino acid sequence having at least 80%, at least 85%, at least 90%, at least 95%, at least 98%, or at least 99%, amino acid sequence identity to the wild-type HSV-TK amino acid sequence set forth above (SEQ ID NO:1), but has a substitution at L169, i.e., amino acid 169 is other than Leu. For example, amino acid 169 is Gly, Ala, Val, Ile, Pro, Phe, Tyr, Trp, Ser, Thr, Cys, Met, Gln, Asn, Lys, Arg, His, Asp, or Glu. In some cases, the substitution is L169F. In some cases, the substitution is L169M. In some cases, the substitution is L169Y. In some cases, the substitution is L169W.

In some cases, the heterologous TK polypeptide comprises an amino acid sequence having at least 80%, at least 85%, at least 90%, at least 95%, at least 98%, or at least 99%, amino acid sequence identity to the wild-type HSV-TK amino acid sequence set forth above (SEQ ID NO:1), where: i) amino acid 159 is other than Leu; ii) amino acid 160 is other than Ile; iii) amino acid 161 is other than Phe; iv) amino acid 168 is other than Ala; and v) amino acid 169 is other than Leu. In some cases, the heterologous TK polypeptide comprises an amino acid sequence having at least 80%, at least 85%, at least 90%, at least 95%, at least 98%, at least 99%, or 100%, amino acid sequence identity to the following amino acid sequence:

("dm30"; SEQ ID NO: 2)

MASYPGHQHASAFDQAARSRGHSNRRTALRPRRQQEATEVRPEQKMPT

LLRVYIDGPHGMGKTTTTQLLVALGSRDDIVYVPEPMTYWRVLGASET

IANIYTTQHRLDQGEISAGDAAVVMT AQITMGMPYAVTDAVLAPHIG

GEAGSSHVPPPALTILADRHPIAYFLCYPAARYLMGSMTPQAVLAFVA

LIPPTLPGTNIVLGALPEDRHIDRLAKRQRPGERLDLAMLAAIRRVYG

LLANTVRYLQGGGSWREDWGQLSGTAVPPQGAEPQSNAGPRPHIGDTL

FTLFRAPELLAPNGDLYNVFAWALDVLAKRLRPMHVFILDYDQSPAGC

RDALLQLTSGMIQTHVTTPGSIPTICDLARTFAREMGEAN, where amino acid 159 is Ile, amino acid 160 is Leu, amino acid 161 is Ala, amino acid 168 is Tyr, and amino acid 169 is Phe.

In some cases, nucleotide sequences encoding the heterologous TK polypeptide comprises a nucleotide sequence having at least 80%, at least 85%, at least 90%, at least 95%, at least 98%, or at least 99%, nucleotide sequence identity to the following nucleotide sequence:

(SEQ ID NO: 11)
ATGGCCTCATATCCTGGTCATCAACACGCTAGTGCCTTCGACCAGGCG

GCGAGATCTCGAGGACATTCGAATAGACGAACAGCATTACGTCCACGA

AGACAACAGGAGGCGACAGAGGTCCGACCTGAACAGAAAATGCCTACA

CTTTTGCGAGTCTACATAGATGGTCCCCACGGAATGGGTAAAACTACC

ACTACCCAGTTGTTAGTCGCCTTAGGTTCTCGAGACGATATTGTCTAT

GTGCCCGAGCCCATGACTTACTGGCGAGTCCTAGGTGCATCGGAAACG

ATAGCGAACATCTATACGACACAGCATCGTTTGGACCAGGGAGAGATC

TCGGCCGGTGACGCAGCAGTCGTAATGACAAGTGCTCAAATTACGATG

GGTATGCCTTATGCGGTAACTGACGCAGTCTTGGCTCCGCATATCGGT

GGAGAGGCCGGATCGTCACACGTGCCCCCTCCAGCGTTAACTATTTTA

GCGGACCGACACCCAATTGCTTACTTCTTATGTTACCCCGCGGCAAGA

TATTTAATGGGATCAATGACCCCGCAAGCTGTGTTAGCTTTTGTGGCA

TTGATTCCGCCAACCTTACCTGGAACGAATATAGTCCTTGGTGCATTA

CCAGAGGATAGACATATTGACAGACTTGCTAAGCGACAGCGACCGGGA

GAGAGATTGGACTTAGCAATGTTGGCGGCCATAAGACGAGTCTACGGA

CTTTTGGCTAATACGGTTAGATATTTGCAAGGAGGAGGAAGTTGGCGA

GAGGATTGGGGTCAGTTGTCTGGTACTGCTGTGCCTCCGCAGGGAGCT

GAGCCTCAGTCTAACGCTGGACCACGACCTCACATCGGAGATACGTTA

TTTACCCTATTCCGTGCGCCGGAATTATTAGCACCCAACGGTGATCTA

TACAACGTCTTTGCGTGGGCCTTGGACGTACTTGCAAAGCGTCTACGT

CCTATGCATGTCTTCATCCTAGACTACGACCAGTCGCCCGCGGGATGT

CGAGACGCCTTGCTACAGTTGACCTCGGGAATGATTCAGACACACGTC

ACCACCCCGGGATCCATACCCACTATTTGTGACTTAGCAAGAACATTT

GCCCGAGAAATGGGTGAAGCTAAC, wherein the encoded amino acid 159 is Ile, amino acid 160 is Leu, amino acid 161 is Ala, amino acid 168 is Tyr, and amino acid 169 is Phe. This sequence is codon optimized for vaccinia virus. In some cases, the heterologous TK polypeptide comprises an amino acid sequence having at least 80%, at least 85%, at least 90%, at least 95%, at least 98%, or at least 99%, amino acid sequence identity to the wild-type HSV-TK amino acid sequence set forth above (SEQ ID NO:1), where: i) amino acid 159 is other than Leu; ii) amino acid 160 is other than Ile; iii) amino acid 161 is other than Phe; iv) amino acid 168 is other than Ala; and v) amino acid 169 is other than Leu. In some cases, the heterologous TK polypeptide comprises an amino acid sequence having at least 80%, at least 85%, at least 90%, at least 95%, at least 98%, at least 99%, or 100%, amino acid sequence identity to the following amino acid sequence:

("SR39"; SEQ ID NO: 3)

MASYPGHQHASAFDQAARSRGHSNRRTALRPRRQQEATEVRPEQKMPTL
LRVYIDGPHGMGKTTTTQLLVALGSRDDIVYVPEPMTYWRVLGASETIA
NIYTTQHRLDQGEISAGDAAVVMTSAQITMGMPYAVTDAVLAPHIGGEA
GSSHAPPPALTIFLDRHPIAFMLCYPAARYLMGSMTPQAVLAFVALIPP

-continued

TLPGTNIVLGALPEDRHIDRLAKRQRPGERLDLAMLAAIRRVYGLLANT
VRYLQGGGSWREDWGQLSGTAVPPQGAEPQSNAGPRPHIGDTLFTLFRA
PELLAPNGDLYNVFAWALDVLAKRLRPMHVFILDYDQSPAGCRDALLQL
TSGMIQTHVTTPGSIPTICDLARTFAREMGEAN, where amino acid 159 is Ile, amino acid 160 is Phe, amino acid 161 is Leu, amino acid 168 is Phe, and amino acid 169 is Met.

In some cases, nucleotide sequences encoding the heterologous TK polypeptide comprises a nucleotide sequence having at least 80%, at least 85%, at least 90%, at least 95%, at least 98%, or at least 99%, nucleotide sequence identity to the following nucleotide sequence:

(SEQ ID NO: 12)

ATGGCCTCATATCCTGGTCATCAACACGCTAGTGCCTTCGACCAGGCG
GCGAGATCTCGAGGACATTCGAATAGACGAACAGCATTACGTCCACGA
AGACAACAGGAGGCGACAGAGGTCCGACCTGAACAGAAAATGCCTACA
CTTTTGCGAGTCTACATAGATGGTCCCCACGGAATGGGTAAAACTACC
ACTACCCAGTTGTTAGTCGCCTTAGGTTCTCGAGACGATATTGTCTAT
GTGCCCGAGCCCATGACTTACTGGCGAGTCCTAGGTGCATCGGAAACG
ATAGCGAACATCTATACGACACAGCATCGTTTGGACCAGGGAGAGATC
TCGGCCGGTGACGCAGCAGTCGTAATGACAAGTGCTCAAATTACGATG
GGTATGCCTTATGCGGTAACTGACGCAGTCTTGGCTCCGCATATCGGT
GGAGAGGCCGGATCGTCACACGCTCCCCCTCCAGCGTTAACTATTTTC
TTAGACCGACACCCAATTGCTTTCATGTTATGTTACCCCGCGGCAAGA
TATTTAATGGGATCAATGACCCCGCAAGCTGTGTTAGCTTTTGTGGCA
TTGATTCCGCCAACCTTACCTGGAACGAATATAGTCCTTGGTGCATTA
CCAGAGGATAGACATATTGACAGACTTGCTAAGCGACAGCGACCGGGA
GAGAGATTGGACTTAGCAATGTTGGCGGCCATAAGACGAGTCTACGGA
CTTTTGGCTAATACGGTTAGATATTTGCAAGGAGGAGGAAGTTGGCGA
GAGGATTGGGGTCAGTTGTCTGGTACTGCTGTGCCTCCGCAGGGAGCT
GAGCCTCAGTCTAACGCTGGACCACGACCTCACATCGGAGATACGTTA
TTTACCCTATTCCGTGCGCCGGAATTATTAGCACCCAACGGTGATCTA
TACAACGTCTTTGCGTGGGCCTTGGACGTACTTGCAAAGCGTCTACGT
CCTATGCATGTCTTCATCCTAGACTACGACCAGTCGCCCGCGGGATGT
CGAGACGCCTTGCTACAGTTGACCTCGGGAATGATTCAGACACACGTC
ACCACCCCGGGATCCATACCCACTATTTGTGACTTAGCAAGAACATTT
GCCCGAGAAATGGGTGAAGCTAAC, wherein the encoded amino acid 159 is Ile, amino acid 160 is Phe, amino acid 161 is Leu, amino acid 168 is Phe, and amino acid 169 is Met. This sequence is codon optimized for vaccinia virus.

In some cases, the heterologous TK polypeptide comprises an amino acid sequence having at least 80%, at least 85%, at least 90%, at least 95%, at least 98%, or at least 99%, amino acid sequence identity to the wild-type HSV-TK amino acid sequence set forth above (SEQ ID NO:1), where amino acid 168 is other than Ala, e.g., where amino acid 168 is Gly, Val, Ile, Leu, Pro, Phe, Tyr, Trp, Ser, Thr, Cys, Met, Gln, Asn, Lys, Arg, His, Asp, or Glu. In some cases, amino acid 168 is His. In some cases, amino acid 168 is Arg. In some cases, amino acid 168 is Lys. In some cases, the heterologous TK polypeptide comprises an amino acid sequence having at least 80%, at least 85%, at least 90%, at least 95%, at least 98%, at least 99%, or 100%, amino acid sequence identity to the following amino acid sequence:

("TK.007"; SEQ ID NO: 4)
MASYPGHQHASAFDQAARSRGHSNRRTALRPRRQQEATEVRPEQKMP

TLLRVYIDGPHGMGKTTTTQLLVALGSRDDIVYVPEPMTYWRVLGAS

ETIANIYTTQHRLDQGEISAGDAAVVMTSAQITMGMPYAVTDAVLAP

HIGGEAGSSHAPPPALTLIFDRHPIA<u>H</u>LLCYPAARYLMGSMTPQAVL

AFVALIPPTLPGTNIVLGALPEDRHIDRLAKRQRPGERLDLAMLAAI

RRVYGLLANTVRYLQGGGSWREDWGQLSGTAVPPQGAEPQSNAGPRP

HIGDTLFTLFRAPELLAPNGDLYNVFAWALDVLAKRLRPMHVFILDY

DQSPAGCRDALLQLTSGMIQTHVTTPGSIPTICDLARTFAREMGEAN, where amino acid 168 is His.

In some cases, nucleotide sequences encoding the heterologous TK polypeptide comprises a nucleotide sequence having at least 80%, at least 85%, at least 90%, at least 95%, at least 98%, or at least 99%, nucleotide sequence identity to the following nucleotide sequence:

(SEQ ID NO: 13)
ATGGCCTCATATCCTGGTCATCAACACGCTAGTGCCTTCGACCAGGC

GGCGAGATCTCGAGGACATTCGAATAGACGAACAGCATTACGTCCAC

GAAGACAACAGGAGGCGACAGAGGTCCGACCTGAACAGAAAATGCCT

ACACTTTTGCGAGTCTACATAGATGGTCCCCACGGAATGGGTAAAAC

TACCACTACCCAGTTGTTAGTCGCCTTAGGTTCTCGAGACGATATTG

TCTATGTGCCCGAGCCCATGACTTACTGGCGAGTCCTAGGTGCATCG

GAAACGATAGCGAACATCTATACGACACAGCATCGTTTGGACCAGGG

AGAGATCTCGGCCGGTGACGCAGCAGTCGTAATGACAAGTGCTCAAA

TTACGATGGGTATGCCTTATGCGGTAACTGACGCAGTCTTGGCTCCG

CATATCGGTGGAGAGGCCGGATCGTCACACGCTCCCCCTCCAGCGTT

AACTCTAATTTTCGACCGACACCCAATTGCTCACCTTTTATGTTACC

CCGCGGCAAGATATTTAATGGGATCAATGACCCCGCAAGCTGTGTTA

GCTTTTGTGGCATTGATTCCGCCAACCTTACCTGGAACGAATATAGT

CCTTGGTGCATTACCAGAGGATAGACATATTGACAGACTTGCTAAGC

GACAGCGACCGGGAGAGAGATTGGACTTAGCAATGTTGGCGGCCATA

AGACGAGTCTACGGACTTTTGGCTAATACGGTTAGATATTTGCAAGG

AGGAGGAAGTTGGCGAGAGGATTGGGGTCAGTTGTCTGGTACTGCTG

TGCCTCCGCAGGGAGCTGAGCCTCAGTCTAACGCTGGACCACGACCT

CACATCGGAGATACGTTATTTACCCTATTCCGTGCGCCGGAATTATT

AGCACCCAACGGTGATCTATACAACGTCTTTGCGTGGGCCTTGGACG

TACTTGCAAAGCGTCTACGTCCTATGCATGTCTTCATCCTAGACTAC

GACCAGTCGCCCGCGGGATGTCGAGACGCCTTGCTACAGTTGACCTC

GGGAATGATTCAGACACACGTCACCACCCCGGGATCCATACCCACTA

TTTGTGACTTAGCAAGAACATTTGCCCGAGAAATGGGTGAAGCTAAC, wherein the encoded amino acid 168 is His. This sequence is codon optimized for vaccinia virus.

The vaccinia virus used to construct a replication-competent, recombinant oncolytic vaccinia virus of the present disclosure can include attenuated and/or tumor-selective vaccinia viruses. As used herein, "attenuated" means low toxicity (for example, low virus replication, low cytolytic activity, low cytotoxic activity) to normal cells (for example, non-tumor cells). As used herein, "tumor selective" means toxicity to tumor cells (for example, oncolytic) higher than that to normal cells (for example, non-tumor cells). Vaccinia viruses genetically modified to be deficient in the function of a specific protein or to suppress the expression of a specific gene or protein (Guse et al. (2011) *Expert Opinion on Biological Therapy* 11:595) may be used in an oncolytic virus of the present disclosure. For example, in order to increase tumor selectivity of vaccinia virus, vaccinia virus deficient in the function of vaccinia growth factor (VGF) (McCart et al. (2001) *Cancer Research* 61:8751); vaccinia virus having a modified vaccinia virus TK gene, a modified hemagglutinin (HA) gene, and a modified F3 gene or an interrupted F3 locus (WO 2005/047458), vaccinia virus deficient in the function of VGF and O1L (WO 2015/076422); vaccinia virus in which a target sequence of a microRNA whose expression is decreased in cancer cells is inserted into the 3' noncoding region of the B5R gene (WO 2011/125469); vaccinia virus deficient in the function of HA and F14.5L (Zhang et al. (2007) *Cancer Research* 67:10038); vaccinia virus deficient in the function of ribonucleotide reductase (Gammon et al. (2010) *PLoS Pathogens* 6:e1000984); vaccinia virus deficient in the function of serine protease inhibitor (e.g., SPI-1, SPI-2) (Guo et al. (2005) *Cancer Research* 65:9991); vaccinia virus deficient in the function of SPI-1 and SPI-2 (Yang et al. (2007) *Gene Therapy* 14:638); vaccinia virus deficient in the function of ribonucleotide reductase genes F4L or I4L (Child et al. (1990) *Virology* 174:625; Potts et al. (2017) *EMBO Mol Med* 9:638); vaccinia virus deficient in the function of B18R (B19R in Copenhagen strain) (Symons et al. (1995) *Cell* 81:551; Kirn et al. (2008) *PLoS Medicine* 4:e353); vaccinia virus deficient in the function of A48R (Hughes et al. (1991) *Journal of Biological Chemistry* 266:20103); vaccinia virus deficient in the function of B8R (Verardi et al. (2001) *Journal of Virology* 75:11); vaccinia virus deficient in the function of B15R (B16R in Copenhagen strain) (Spriggs et al. (1992) *Cell* 71:145); vaccinia virus deficient in the function of A41R (Ng et al. (2001) *Journal of General Virology* 82:2095); vaccinia virus deficient in the function of A52R (Bowie et al. (2000) *Proc. Natl. Acad. Sci. USA* 97:10162); vaccinia virus deficient in the function of F1L (Gerlic et al. (2013) *Proc. Natl. Acad. Sci. USA* 110:7808); vaccinia virus deficient in the function of E3L (Chang et al. (1992) *Proc. Natl. Acad. Sci. USA* 89:4825); vaccinia virus deficient in the function of A44R-A46R (Bowie et al. (2000) *Proc. Natl. Acad. Sci. USA* 97:10162); vaccinia virus deficient in the function of K1L (Bravo Cruz et al. (2017) *Journal of Virology* 91:e00524); vaccinia virus deficient in the function of A48R, B18R, C11R, and TK (Mejías-Pérez et al. (2017) *Molecular Therapy: Oncolytics* 8:27); or vaccinia virus having mutations in the E3L and K3L regions (WO 2005/007824) may be used. Moreover, vaccinia virus deficient in the function of O1L may be used (Schweneker et al. (2012) *Journal of Virology* 86:2323). Moreover, vaccinia virus deficient in the extracellular region of B5R (Bell et al. (2004) *Virology* 325:425) or vaccinia virus deficient in the A34R region (Thirunavukarasu et al. (2013) *Molecular Therapy* 21:1024) may be used. Moreover, vaccinia virus deficient in interleukin-1b (IL-1b) receptor (WO 2005/030971) may be used. Such insertion of a foreign gene or deletion or mutation of a gene can be made, for example, by a known homologous recombination or site-directed mutagenesis. Moreover, vaccinia virus having a combination of two or more of such genetic modifications may be used in a replication-competent, recombinant oncolytic vaccinia virus of the present disclosure.

As used herein, "being deficient" means that the gene region specified by this term has reduced or no function and includes a deficiency resulting from one or more of: i) mutation (e.g., substitution, inversion, etc.) and/or truncation and/or deletion of the gene region specified by this term; ii) mutation and/or truncation and/or deletion of a promoter region controlling expression of the gene region; and iii) mutation and/or truncation and/or deletion of a polyadenylation sequence such that translation of a polypeptide encoded by the gene region is reduced or eliminated. A replication-competent, recombinant oncolytic vaccinia virus of the present disclosure that comprises a genetic alteration such that the replication-competent, recombinant oncolytic vaccinia virus is "deficient" in a given vaccinia virus gene exhibits reduced production and/or activity of a gene product (e.g., mRNA gene product; polypeptide gene product) of the gene; for example, the amount and/or activity of the gene product is less than 75%, less than 60%, less than 50%, less than 40%, less than 30%, less than 25%, less than 20%, less than 15%, less than 10%, less than 5%, or less than 1% of the amount and/or activity of the same gene product produced by wild-type vaccinia virus, or by a control vaccinia virus that does not comprise the genetic alteration. For example, "being deficient" may be a result of the deletion in a region consisting of the specified gene region or the deletion in a neighboring gene region comprising the specified gene region. As an example, a mutation and/or truncation and/or deletion of a promoter region that reduces transcription of a gene region can result in deficiency. A gene region can also be rendered deficient through incorporation of a transcriptional termination element such that translation of a polypeptide encoded by the gene region is reduced or eliminated. A gene region can also be rendered deficient through use of a gene-editing enzyme or a gene-editing complex (e.g., a CRISPR/Cas effector polypeptide complexed with a guide RNA) to reduce or eliminate transcription of the gene region. A gene region can also be rendered deficient through use of competitive reverse promoter/polymerase occupancy to reduce or eliminate transcription of the gene region. A gene region can also be rendered deficient by insertion of a nucleic acid into the gene region, thereby knocking out the gene region.

As noted above, a replication-competent, recombinant oncolytic vaccinia virus of the present disclosure will in some instances lack endogenous vaccinia virus thymidine kinase (TK) activity. In some cases, a replication-competent, recombinant oncolytic vaccinia virus of the present disclosure comprises a deletion of all or a portion of the vaccinia virus TK coding region, such that the replication-competent, recombinant oncolytic vaccinia virus is TK deficient. For example, in some cases, a replication-competent, recombinant oncolytic vaccinia virus of the present disclosure comprises a J2R deletion. See, e.g., Mejía-Perez et al. (2018) *Mol. Ther. Oncolytics* 8:27.

A replication-competent, recombinant oncolytic vaccinia virus of the present disclosure will in some instances comprise one or more modifications that enhance production of extracellular enveloped virus (EEV). For example, in some cases, a replication-competent, recombinant oncolytic vaccinia virus of the present disclosure comprises a modification in the vaccinia virus A34R gene that provides for a K151E substitution in the encoded A34 protein (formerly known as "gp22-24"). See, e.g., Blasco et al. (1993) *J. Virol.* 67(6):3319-3325; and Thirunavukarasu et al. (2013) *Mol. Ther.* 21:1024. The A34R gene encodes vaccinia virus gp22-24.

A replication-competent, recombinant oncolytic vaccinia virus of the present disclosure can be constructed from any of a variety of strains of vaccinia virus. Strains of vaccinia virus suitable for use include, but are not limited to, the strains Lister, New York City Board of Health (NYBH), Wyeth, Copenhagen, Western Reserve (WR), Modified Vaccinia Ankara (MVA), EM63, Ikeda, Dalian, LIVP, Tian Tan, IHD-J, Tashkent, Bern, Paris, Dairen and derivatives the like. In some cases, a replication-competent, recombinant oncolytic vaccinia virus of the present disclosure is a Copenhagen strain vaccinia virus. In some cases, a replication-competent, recombinant oncolytic vaccinia virus of the present disclosure is a WR strain vaccinia virus.

The nucleotide sequences of the genomes of vaccinia viruses of various strains are known in the art. See, e.g., Goebel et al. (1990) *Virology* 179:247; Goebel et al. (1990) *Virology* 179:517. The nucleotide sequence of the Copenhagen strain vaccinia virus is known; see, e.g., GenBank Accession No. M35027. The nucleotide sequence of the WR strain vaccinia virus is known; see, e.g., GenBank Accession No. AY243312; and GenBank Accession No. NC_006998. The WR strain of vaccinia virus is available from the American Type Culture Collection (ATCC); ATCC VR-1354.

A replication-competent, recombinant oncolytic vaccinia virus of the present disclosure exhibits oncolytic activity. Examples of methods for evaluating whether a given virus exhibits oncolytic activity include a method for evaluating decrease of the survival rate of cancer cells by the addition of the virus. Examples of cancer cells to be used for the evaluation include the malignant melanoma cell RPMI-7951 (for example, ATCC HTB-66), the lung adenocarcinoma HCC4006 (for example, ATCC CRL-2871), the lung carcinoma A549 (for example, ATCC CCL-185), the lung carcinoma HOP-62 (for example, DCTD Tumor Repository), the lung carcinoma EKVX (for example, DCTD Tumor Repository), the small cell lung cancer cell DMS 53 (for example, ATCC CRL-2062), the lung squamous cell carcinoma NCI-H226 (for example, ATCC CRL-5826), the kidney cancer cell Caki-1 (for example, ATCC HTB-46), the bladder cancer cell 647-V (for example, DSMZ ACC 414), the head and neck cancer cell Detroit 562 (for example, ATCC CCL-138), the breast cancer cell JIMT-1 (for example, DSMZ ACC 589), the breast cancer cell MDA-MB-231 (for example, ATCC HTB-26), the breast cancer cell MCF7 (for example, ATCC HTB-22), the breast cancer HS-578T (for example, ATCC HTB-126), the breast ductal carcinoma T-47D (for example, ATCC HTB-133), the esophageal cancer cell OE33 (for example, ECACC 96070808), the glioblastoma U-87MG (for example, ECACC 89081402), the neuroblastoma GOTO (for example, JCRB JCRB0612), the myeloma RPMI 8226 (for example, ATCC CCL-155), the ovarian cancer cell SK-OV-3 (for example, ATCC HTB-77), the ovarian cancer cell OVMANA (for example, JCRB JCRB1045), the cervical cancer cell line HeLa (for example, ATCC CCL-2), the colon cancer cell RKO (for example, ATCC CRL-2577), the colon cancer cell HT-29 (for example, ATCC HTB-38), the colon cancer Colo 205 (for example, ATCC CCL-222), the colon cancer SW620 (for example, ATCC CCL-227), the colorectal carcinoma HCT 116 (for example, ATCC CCL-247), the pancreatic cancer cell BxPC-3 (for example, ATCC CRL-1687), the bone osteosarcoma U-2 OS (for example, ATCC HTB-96), the prostate cancer cell LNCaP clone FGC (for example, ATCC CRL-1740), the hepatocellular carcinoma JHH-4 (for example, JCRB JCRB0435), the mesothelioma NCI-H28 (for example, ATCC CRL-5820), the cervical cancer cell SiHa (for example, ATCC HTB-35), and the gastric cancer cell Kato III (for example, RIKEN BRC RCB2088).

A nucleic acid comprising a nucleotide sequence encoding a TKv polypeptide can be introduced into vaccinia virus using established techniques. An example of such a technique is homologous recombination and reactivation (Yao and Evans (2003) *J Virol* 77(13):7281-90). For example, a plasmid (also referred to as transfer vector plasmid DNA) in which a nucleic acid comprising a nucleotide sequence encoding a TKv polypeptide is inserted can be generated, generating a recombinant transfer vector; the recombinant transfer vector can be introduced into cells transfected with digested genomic DNA from vaccinia virus and infected with a helper virus. The nucleic acid comprising a nucleotide sequence encoding the TKv polypeptide is then introduced into the vaccinia virus from the recombinant transfer vector via homologous recombination. The region in which a nucleic acid comprising a nucleotide sequence encoding a TKv polypeptide is introduced can be the endogenous vaccinia virus TK-encoding gene, e.g., J2R. The nucleic acid encoding a TKv polypeptide can replace all or a portion of vaccinia virus J2R. The nucleic acid encoding a TKv polypeptide can also replace all or a portion of any vaccinia gene that is not required for replication, including, but not limited to, B15R, B16R, B8R, B18R, C11R, C12L, B19R, A41L, A44L, A45R, A46R, A52R, or the like. The nucleic acid encoding a TKv polypeptide can also be introduced into an intergenic region in between two viral genes such as between the B15R and B17L genes.

In some cases, the nucleotide sequence encoding the TKv polypeptide is operably linked to a transcriptional control element, e.g., a promoter. In some cases, the promoter provides for expression of the TKv polypeptide in tumor cells. Suitable promoters include, but are not limited to, a pSEL promoter, a PSFJ1-10 promoter, a PSFJ2-16 promoter, a pHyb promoter, a Late-Early optimized promoter, a p7.5K promoter, a p11K promoter, a T7.10 promoter, a CPX promoter, a modified H5 promoter, a HF promoter, an H6 promoter, an H5 promoter, an H4 promoter, an F17 promoter, and a T7 hybrid promoter.

In some cases, the nucleotide sequence encoding the TKv polypeptide is operably linked to a regulatable promoter. In some cases, the regulatable promoter is a reversible promoter. In some cases, the nucleotide sequence encoding the TKv polypeptide is operably linked to a tetracycline-regulated promoter, (e.g., a promoter system such as TetActivators, TetON, TetOFF, Tet-On Advanced, Tet-On 3G, etc.). In some cases, the nucleotide sequence encoding the TKv polypeptide is operably linked to a repressible promoter. In some cases, the nucleotide sequence encoding the TKv polypeptide is operably linked to a promoter that is tetracycline repressible, e.g., the promoter is repressed in the presence of tetracycline or a tetracycline analog or derivative. In some cases, the nucleotide sequence encoding the TKv polypeptide is operably linked to a TetOFF promoter system. Bujard and Gossen (1992) *Proc. Natl. Acad. Sci. USA* 89:5547. For example, a TetOFF promoter system is repressed (inactive) in the presence of tetracycline (or suitable analog or derivative, such as doxycycline); once tetracycline is removed, the promoter is active and drives expression of the TKv polypeptide. In some cases, the nucleotide sequence encoding the TKv polypeptide is operably linked to a promoter that is tetracycline activatable, e.g., the promoter is activated in the presence of tetracycline or a tetracycline analog or derivative.

Compositions

The present disclosure provides a composition, which may be a pharmaceutical composition, comprising a replication-competent, recombinant oncolytic vaccinia virus of the present disclosure. In some cases, the composition is a pharmaceutical composition. In some cases, the pharmaceutical composition is suitable for administering to an individual in need thereof, where the individual is a human.

A pharmaceutical composition comprising a replication-competent, recombinant oncolytic vaccinia virus of the present disclosure can optionally include a pharmaceutically acceptable carrier(s) that facilitate processing of an active ingredient into pharmaceutically acceptable compositions. As used herein, the term “pharmacologically acceptable carrier” refers to any carrier that has substantially no long-term or permanent detrimental effect when administered and encompasses terms such as “pharmacologically acceptable vehicle, stabilizer, diluent, auxiliary or excipient.” Such a carrier generally is mixed with a replication-competent, recombinant oncolytic vaccinia virus of the present disclosure, and can be a solid, semi-solid, or liquid agent. It is understood that a replication-competent, recombinant oncolytic vaccinia virus of the present disclosure can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with a replication-competent, recombinant oncolytic vaccinia virus of the present disclosure, its use in pharmaceutically acceptable compositions is contemplated. Non-limiting examples of specific uses of such pharmaceutical carriers can be found in “Pharmaceutical Dosage Forms and Drug Delivery Systems” (Howard C. Ansel et al., eds., Lippincott Williams & Wilkins Publishers, 7$^{th}$ ed. 1999); “Remington: The Science and Practice of Pharmacy” (Alfonso R. Gennaro ed., Lippincott, Williams & Wilkins, 20$^{th}$ 2000); “Goodman & Gilman’s The Pharmacological Basis of Therapeutics” Joel G. Hardman et al., eds., McGraw-Hill Professional, 10$^{th}$ ed. 2001); and “Handbook of Pharmaceutical Excipients” (Raymond C. Rowe et al., APhA Publications, 4$^{th}$ edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A pharmaceutical composition of the present disclosure can comprise a replication-competent, recombinant oncolytic vaccinia virus of the present disclosure in an amount of from about $10^2$ plaque-forming units (pfu) per ml (pfu/ml) to about $10^4$ pfu/ml, from about $10^4$ pfu/ml to about $10^5$ pfu/ml, from about $10^5$ pfu/ml to about $10^6$ pfu/ml, from about $10^6$ pfu/ml to about $10^7$ pfu/ml, from about $10^7$ pfu/ml to about $10^8$ pfu/ml, from about $10^8$ pfu/ml to about $10^9$ pfu/ml, from about $10^9$ pfu/ml to about $10^{10}$ pfu/ml, from about $10^{10}$ pfu/ml to about $10^{11}$ pfu/ml, or from about $10^{11}$ pfu/ml to about $10^{12}$ pfu/ml.

Methods of Inducing Oncolysis

The present disclosure provides methods of inducing oncolysis in an individual having a tumor, the methods comprising administering to the individual an effective amount of a replication-competent, recombinant oncolytic vaccinia virus of the present disclosure or a composition of the present disclosure.

In some cases, an "effective amount" of a replication-competent, recombinant oncolytic vaccinia virus of the present disclosure is an amount that, when administered in one or more doses to an individual in need thereof, reduces the number of cancer cells in the individual. For example, in some cases, an "effective amount" of a replication-competent, recombinant oncolytic vaccinia virus of the present disclosure is an amount that, when administered in one or more doses to an individual in need thereof, reduces the number of cancer cells in the individual by at least 10%, at least 15%, at least 20%, at least 25%, at least 30%, at least 40%, at least 50%, at least 60%, at least 70%, at least 80%, at least 90%, or at least 95%, compared to the number of cancer cells in the individual before administration of the replication-competent, recombinant oncolytic vaccinia virus, or in the absence of administration with the replication-competent, recombinant oncolytic vaccinia virus. In some cases, an "effective amount" of a replication-competent, recombinant oncolytic vaccinia virus of the present disclosure is an amount that, when administered in one or more doses to an individual in need thereof, reduces the number of cancer cells in the individual to undetectable levels. In some cases, an "effective amount" of a replication-competent, recombinant oncolytic vaccinia virus of the present disclosure is an amount that, when administered in one or more doses to an individual in need thereof, reduces the tumor mass in the individual. For example, in some cases, an "effective amount" of a replication-competent, recombinant oncolytic vaccinia virus of the present disclosure is an amount that, when administered in one or more doses to an individual in need thereof, reduces the tumor mass in the individual by at least 10%, at least 15%, at least 20%, at least 25%, at least 30%, at least 40%, at least 50%, at least 60%, at least 70%, at least 80%, at least 90%, or at least 95%, compared to the tumor mass in the individual before administration of the replication-competent, recombinant oncolytic vaccinia virus, or in the absence of administration with the replication-competent, recombinant oncolytic vaccinia virus.

In some cases, an "effective amount" of a replication-competent, recombinant oncolytic vaccinia virus of the present disclosure is an amount that, when administered in one or more doses to an individual in need thereof, increases survival time of the individual. For example, in some cases, an "effective amount" of a replication-competent, recombinant oncolytic vaccinia virus of the present disclosure is an amount that, when administered in one or more doses to an individual in need thereof, increases survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the replication-competent, recombinant oncolytic vaccinia virus.

In some cases, an "effective amount" of a replication-competent, recombinant oncolytic vaccinia virus of the present disclosure is an amount that, when administered in one or more doses to an individual in need thereof, induces a durable anti-tumor immune response, e.g., an anti-tumor immune response that provides for reduction in tumor cell number and/or tumor mass and/or tumor growth for at least 1 month, at least 2 months, at least 6 months, or at least 1 year.

A suitable dosage can be determined by an attending physician or other qualified medical personnel, based on various clinical factors. As is well known in the medical arts, dosages for any one patient depend upon many factors, including the patient's size, body surface area, age, tumor burden, and other relevant factors.

A replication-competent, recombinant oncolytic vaccinia virus of the present disclosure can be administered in an amount of from about $10^2$ plaque-forming units (pfu) to about $10^4$ pfu, from about $10^4$ pfu to about $10^5$ pfu, from about $10^5$ pfu to about $10^6$ pfu, from about $10^6$ pfu to about $10^7$ pfu, from about $10^7$ pfu to about $10^8$ pfu, from about $10^8$ pfu to about $10^9$ pfu, from about $10^9$ pfu to about $10^{10}$ pfu, from about $10^{10}$ pfu to about $10^{11}$ pfu, or from about $10^{11}$ to about $10^{12}$ pfu, per dose.

In some cases, a replication-competent, recombinant oncolytic vaccinia virus of the present disclosure is administered in a total amount of from about $1\times10^9$ pfu to $5\times10^{11}$ pfu. In some cases, a replication-competent, recombinant oncolytic vaccinia virus of the present disclosure is administered in a total amount of from about $1\times10^9$ pfu to about $5\times10^9$ pfu, from about $5\times10^9$ pfu to about $10^{10}$ pfu, from about $10^{10}$ pfu to about $5\times10^{10}$ pfu, from about $5\times10^{10}$ pfu to about $10^{11}$ pfu, from about $10^{11}$ pfu to about $5\times10^{11}$ pfu, or from about $5\times10^{11}$ pfu to about $10^{12}$ pfu. In some cases, a replication-competent, recombinant oncolytic vaccinia virus of the present disclosure is administered in a total amount of about $2\times10^{10}$ pfu.

In some cases, a replication-competent, recombinant oncolytic vaccinia virus of the present disclosure is administered in an amount of from about $1\times10^8$ pfu/kg patient weight to about $5\times10^9$ pfu/kg patient weight. In some cases, a replication-competent, recombinant oncolytic vaccinia virus of the present disclosure is administered in an amount of from about $1\times10^8$ pfu/kg patient weight to about $5\times10^8$ pfu/kg patient weight, from about $5\times10^8$ pfu/kg patient weight to about $10^9$ pfu/kg patient weight, or from about $10^9$ pfu/kg patient weight to about $5\times10^9$ pfu/kg patient weight. In some cases, a replication-competent, recombinant oncolytic vaccinia virus of the present disclosure is administered in an amount of $1\times10^8$ pfu/kg patient weight. In some cases, a replication-competent, recombinant oncolytic vaccinia virus of the present disclosure is administered in an amount of $2\times10^8$ pfu/kg patient weight. In some cases, a replication-competent, recombinant oncolytic vaccinia virus of the present disclosure is administered in an amount of $3\times10^8$ pfu/kg patient weight. In some cases, a replication-competent, recombinant oncolytic vaccinia virus of the present disclosure is administered in an amount of $4\times10^8$ pfu/kg patient weight. In some cases, a replication-competent, recombinant oncolytic vaccinia virus of the present disclosure is administered in an amount of $5\times10^8$ pfu/kg patient weight.

In some cases, multiple doses of a replication-competent, recombinant oncolytic vaccinia virus of the present disclosure are administered. The frequency of administration of a replication-competent, recombinant oncolytic vaccinia virus of the present disclosure can vary depending on any of a variety of factors, e.g., severity of the symptoms, etc. For example, in some embodiments, a replication-competent, recombinant oncolytic vaccinia virus of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a replication-competent, recombinant oncolytic vaccinia virus of the present disclosure, e.g., the period of time over which a replication-competent, recombinant oncolytic vaccinia virus of the present disclosure is administered, can vary, depending on any of a variety of factors, e.g., patient response, etc. For example, a replication-competent, recombinant oncolytic vaccinia virus of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A replication-competent, recombinant oncolytic vaccinia virus of the present disclosure is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intratracheal, intrathecal, intracranial, subcutaneous, intradermal, topical application, intravenous, intraarterial, intraperitoneal, intrabladder, rectal, nasal, oral, and other enteral and parenteral routes of administration. Routes of administration may be combined, if desired, or adjusted depending upon the replication-competent, recombinant oncolytic vaccinia virus and/or the desired effect. A replication-competent, recombinant oncolytic vaccinia virus of the present disclosure can be administered in a single dose or in multiple doses.

In some cases, a replication-competent, recombinant oncolytic vaccinia virus of the present disclosure is administered intravenously. In some cases, a replication-competent, recombinant oncolytic vaccinia virus of the present disclosure is administered intramuscularly. In some cases, a replication-competent, recombinant oncolytic vaccinia virus of the present disclosure is administered locally. In some cases, a replication-competent, recombinant oncolytic vaccinia virus of the present disclosure is administered intratumorally. In some cases, a replication-competent, recombinant oncolytic vaccinia virus of the present disclosure is administered peritumorally. In some cases, a replication-competent, recombinant oncolytic vaccinia virus of the present disclosure is administered intracranially. In some cases, a replication-competent, recombinant oncolytic vaccinia virus of the present disclosure is administered subcutaneously. In some cases, a replication-competent, recombinant oncolytic vaccinia virus of the present disclosure is administered intra-arterially. In some cases, a replication-competent, recombinant oncolytic vaccinia virus of the present disclosure is administered intraperitoneally. In some cases, a replication-competent, recombinant oncolytic vaccinia virus of the present disclosure is administered via an intrabladder route of administration. In some cases, a replication-competent, recombinant oncolytic vaccinia virus of the present disclosure is administered intrathecally.

The present disclosure provides a replication-competent, recombinant oncolytic vaccinia virus of the present disclosure for use as a medicament.

The present disclosure provides a replication-competent, recombinant oncolytic vaccinia virus of the present disclosure for use in a method of inducing oncolysis in an individual having a tumor.

Combination

In some cases, a replication-competent, recombinant oncolytic vaccinia virus of the present disclosure is administered as an adjuvant therapy to a standard cancer therapy. Standard cancer therapies include surgery (e.g., surgical removal of cancerous tissue), radiation therapy, bone marrow transplantation, chemotherapeutic treatment, antibody treatment, biological response modifier treatment, immunotherapy treatment, and certain combinations of the foregoing. In some cases, a method of the present disclosure comprises: a) administering to an individual in need thereof a replication-competent, recombinant oncolytic vaccinia virus of the present disclosure, or a composition comprising same; and b) administering to the individual a second cancer therapy. In some cases, the second cancer therapy is selected from chemotherapy, biological therapy, radiotherapy, immunotherapy (including oncolytic vaccines), hormone therapy, anti-vascular therapy, cryotherapy, toxin therapy, oncolytic virus therapy (e.g., an oncolytic virus other than a replication-competent, recombinant oncolytic vaccinia virus of the present disclosure), a cell therapy, and surgery.

Radiation therapy includes, but is not limited to, x-rays or gamma rays that are delivered from either an externally applied source such as a beam, or by implantation of small radioactive sources.

Suitable antibodies for use in cancer treatment include, but are not limited to, e.g., avelumab (Bavencio®; an anti-PD-L1 antibody), trastuzumab (Herceptin), bevacizumab (Avastin™) cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), $^{90}$Y-labelled ibritumomab tiuxetan (Zevalin™), $^{131}$I-labelled tositumoma (Bexxar™), etc. Suitable antibodies for use in cancer treatment include, but are not limited to, e.g., Ipilimumab targeting CTLA-4 (as used in the treatment of Melanoma, Prostate Cancer, RCC); Tremelimumab targeting CTLA-4 (as used in the treatment of CRC, Gastric, Melanoma, NSCLC); Nivolumab targeting PD-1 (as used in the treatment of Melanoma, NSCLC, RCC); MK-3475 targeting PD-1 (as used in the treatment of Melanoma); Pidilizumab targeting PD-1 (as used in the treatment of Hematologic Malignancies); BMS-936559 targeting PD-L1 (as used in the treatment of Melanoma, NSCLC, Ovarian, RCC); MEDI4736 targeting PD-L1; MPDL33280A targeting PD-L1 (as used in the treatment of Melanoma); Rituximab targeting CD20 (as used in the treatment of Non-Hodgkin's lymphoma); Ibritumomab tiuxetan and tositumomab (as used in the treatment of Lymphoma); Brentuximab vedotin targeting CD30 (as used in the treatment of Hodgkin's lymphoma); Gemtuzumab ozogamicin targeting CD33 (as used in the treatment of Acute myelogenous leukemia); Alemtuzumab targeting CD52 (as used in the treatment of Chronic lymphocytic leukemia); IGN101 and adecatumumab targeting EpCAM (as used in the treatment of Epithelial tumors (breast, colon and lung)); Labetuzumab targeting CEA (as used in the treatment of Breast, colon and lung tumors); huA33 targeting gpA33 (as used in the treatment of Colorectal carcinoma); Pemtumomab and oregovomab targeting Mucins (as used in the treatment of Breast, colon, lung and ovarian tumors); CC49 (minretumomab) targeting TAG-72 (as used in the treatment of Breast, colon and lung tumors); cG250 targeting CAIX (as used in the treatment of Renal cell carcinoma); J591 targeting PSMA (as used in the treatment of Prostate carcinoma); MOv18 and MORAb-003 (farletuzumab) targeting Folate-binding protein (as used in the treatment of Ovarian tumors); 3F8, ch14.18 and KW-2871 targeting Gangliosides (such as GD2, GD3 and GM2) (as used in the treatment of Neuroectodermal tumors and some epithelial tumors); hu3S193 and IgN311 targeting Le y (as used in the treatment of Breast, colon, lung and prostate tumors); Bevacizumab targeting VEGF (as used in the treatment of Tumor vasculature); IM-2C6 and CDP791 targeting VEGFR (as used in the treatment of Epithelium-derived solid tumors); Etaracizumab targeting Integrin_V_3 (as used in the treatment of Tumor vasculature); Volociximab targeting Integrin_5_1 (as used in the treatment of Tumor vasculature); Cetuximab, panitumumab, nimotuzumab and 806 targeting EGFR (as used in the treatment of Glioma, lung, breast, colon, and head and neck tumors); Trastuzumab and pertuzumab targeting ERBB2 (as used in the treatment of Breast, colon, lung, ovarian and prostate tumors); MM-121 targeting ERBB3 (as used in the treatment of Breast, colon, lung, ovarian and prostate, tumors); AMG 102, METMAB and SCH 900105 targeting MET (as used in the treatment of Breast, ovary and lung tumors); AVE1642, IMC-A12, MK-0646, R1507 and CP 751871 targeting IGF1R (as used in the treatment of Glioma, lung, breast, head and neck, prostate and thyroid cancer); KB004 and IIIA4 targeting EPHA3 (as used in the treatment of Lung, kidney and colon tumors, melanoma, glioma and hematological malignancies); Mapatumumab (HGS-ETR1) targeting TRAILR1 (as used in the treatment of Colon, lung and pancreas tumors and hematological malignancies); HGS-ETR2 and CS-1008 targeting TRAILR2; Denosumab targeting RANKL (as used in the treatment of Prostate cancer and bone metastases); Sibrotuzumab and F19 targeting FAP (as used in the treatment of Colon, breast, lung, pancreas, and head and neck tumors); 81C6 targeting Tenascin (as used in the treatment of Glioma, breast and prostate tumors); Blinatumomab (Blincyto; Amgen) targeting CD3 (as used in the treatment of ALL); pembrolizumab targeting PD-1 as used in cancer immunotherapy; 9E10 antibody targeting c-Myc; and the like.

In some cases, a method of the present disclosure comprises administering: a) an effective amount of a replication-competent, recombinant oncolytic vaccinia virus of the present disclosure; and b) an anti-PD-1 antibody. In some cases, a method of the present disclosure comprises administering: a) an effective amount of a replication-competent, recombinant oncolytic vaccinia virus of the present disclosure; and b) an anti-PD-L1 antibody. Suitable anti-PD-1 antibodies include, but are not limited to, pembrolizumab (Keytruda®; MK-3475), Nivolumab (Opdivo®; BMS-926558; MDX1106), Pidilizumab (CT-011), AMP-224, AMP-514 (MEDI-0680), and PDR001 and PF-06801591. Suitable anti-PD-L1 antibodies include, but are not limited to, BMS-936559 (MDX1105), durvalumab (MEDI4736; Imfinzi), Atezolizumab (MPDL33280A; Tecentriq), MSB0010718C, and Avelumab (Bavencio; MSB0010718C). See, e.g., Sunshine and Taube (2015) *Curr. Opin. Pharmacol.* 23:32; and Heery et al. (2017) *The Lancet Oncology* 18:587; Iwai et al. (2017) *J. Biomed. Sci.* 24:26; Hu-Lieskovan et al. (2017) *Annals of Oncology* 28: issue Suppl. 5, mdx376.048; and U.S. Patent Publication No. 2016/0159905.

In some cases, a suitable antibody is a bispecific antibody, e.g., a bispecific monoclonal antibody. Catumaxomab, blinatumomab, solitomab, pasotuxizumab, and flotetuzumab are non-limiting examples of bispecific antibodies suitable for use in cancer therapy. See, e.g., Chames and Baty (2009) *MAbs* 1:539; and Sedykh et al. (2018) *Drug Des. Devel. Ther.* 12:195.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α.; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U, cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Cell therapy includes chimeric antigen receptor (CAR) T cell therapy (CAR-T therapy); natural killer (NK) cell therapy; dendritic cell (DC) therapy (e.g., DC-based vaccine); T cell receptor (TCR) engineered T cell-based therapy; and the like.

Synthetic Analogs of 2'-deoxyguanosine

A method of the present disclosure can comprise: a) administering an effective amount of a replication-competent, recombinant oncolytic vaccinia virus of the present disclosure; and b) administering an effective amount of a synthetic analog of 2'-deoxy-guanosine.

In some cases, an effective amount of a synthetic analog of 2'-deoxy-guanosine is an amount that is effective to reduce an adverse side effect of administration of a replication-competent, recombinant oncolytic vaccinia virus of the present disclosure. For example, a possible adverse side effect is skin lesions. In some cases, an effective amount of a synthetic analog of 2'-deoxy-guanosine is an amount that, when administered to an individual in one or more doses, is effective to reduce the number and/or severity and/or duration of vaccinia virus-induced skin lesions in the individual. For example, an effective amount of a synthetic analog of 2'-deoxy-guanosine can be an amount that, when administered to an individual in one or more doses, is effective to reduce the number and/or severity and/or duration of vaccinia virus-induced skin lesions in the individual by at least 10%, at least 15%, at least 20%, at least 25%, at least 30%, at least 40%, at least 50%, at least 60%, at least 75%, or more than 75%, compared with the number and/or severity and/or duration of vaccinia virus-induced skin lesions in the individual prior to administration of the synthetic analog of 2'-deoxy-guanosine or in the absence of administration of the synthetic analog of 2'-deoxy-guanosine. In some cases, an effective amount of a synthetic analog of 2'-deoxy-guanosine is an amount that, when administered to an individual in one or more doses, is effective to reduce shedding of virus from vaccinia virus-induced skin lesions. For example, in some cases, an effective amount of a synthetic analog of 2'-deoxy-guanosine is an amount that, when administered to an individual in one or more doses, is effective to reduce shedding of virus from vaccinia virus-induced skin lesions by at least 10%, at least 15%, at least 20%, at least 25%, at least 30%, at least 40%, at least 50%, at least 60%, at least 75%, or more than 75%, compared with the level or degree of virus shedding from vaccinia virus-induced skin lesions in the individual prior to administration of the synthetic analog of 2'-deoxy-guanosine or in the absence of administration of the synthetic analog of 2'-deoxy-guanosine. Where the adverse side effect is a skin lesion, in some cases, the synthetic analog of 2'-deoxy-guanosine can be administered by any convenient route of administration (e.g., topically, orally, intravenously, etc.). For example, where the adverse side effect is a skin lesion, in some cases, the synthetic analog of 2'-deoxy-guanosine can be administered topically.

Administration of a synthetic analog of 2'-deoxy-guanosine reduces replication of a replication-competent, recombinant oncolytic vaccinia virus of the present disclosure. Such reduction in replication of the replication-competent, recombinant oncolytic vaccinia virus of the present disclosure may be desirable, e.g., to control the level of replication-competent, recombinant oncolytic vaccinia virus in an individual, to control the effect of the replication-competent, recombinant oncolytic vaccinia virus, and the like. In some cases, an effective amount of a synthetic analog of 2'-deoxy-guanosine is an amount that, when administered to an individual in one or more doses, is effective to reduce replication of a replication-competent, recombinant oncolytic vaccinia virus of the present disclosure in an individual by at least 10%, at least 15%, at least 20%, at least 25%, at least 30%, at least 40%, at least 50%, at least 60%, at least 75%, or more than 75%, compared with the level of replication of the replication-competent, recombinant oncolytic vaccinia virus in the individual prior to administration of the synthetic analog of 2'-deoxy-guanosine or in the absence of administration of the synthetic analog of 2'-deoxy-guanosine.

A synthetic analog of 2'-deoxy-guanosine can be administered after administration of a replication-competent, recombinant oncolytic vaccinia virus of the present disclosure. For example, a synthetic analog of 2'-deoxy-guanosine can be administered 1 day to 7 days, from 7 days to 2 weeks, from 2 weeks to 1 month, from 1 month to 3 months, or more than 3 months, after administration of the replication-competent, recombinant oncolytic vaccinia virus.

In some cases, a synthetic analog of 2'-deoxy-guanosine can be administered to an individual once oncolytic vaccinia virus-induced slowing of tumor growth has occurred and/or once viral replication is at or just after its peak and/or once circulating antibody to vaccinia virus proteins are at or just after their peak. Whether slowing of tumor growth has occurred, following administration of a replication-competent, recombinant oncolytic vaccinia virus of the present disclosure, can be determined using any of a variety of established methods to measure tumor growth and/or cancer cell number. Whether replication of a replication-competent, recombinant oncolytic vaccinia virus of the present disclosure in an individual is at its peak or just after its peak can be determined by detecting and/or measuring levels of TKv polypeptide in the individual, as described herein, where a non-limiting example of a suitable method is PET. Whether circulating antibody to a replication-competent, recombinant oncolytic vaccinia virus of the present disclosure is at or just after its peak can be measured using standard methods for measuring the levels of an antibody, where such methods include, e.g., enzyme-linked immunosorbent assay (ELISA), radioimmunoassay (RIA), and the like.

As an example, a method of the present disclosure can comprise: a) administering to an individual in need thereof an effective amount of a replication-competent, recombinant oncolytic vaccinia virus of the present disclosure; b) measuring: i) tumor size and/or cancer cell number in the individual; and/or ii) levels of TKv polypeptide in the individual; and/or iii) levels of antibody to the replication-competent, recombinant oncolytic vaccinia virus in the individual; and c) where the measuring step indicates that: i) tumor growth has slowed and/or the number of cancer cells has decreased, compared to the tumor growth and/or the number of cancer cells before administration of the replication-competent, recombinant oncolytic vaccinia virus; and/or ii) the level of TKv polypeptide in the individual is at or just past its peak; and/or iii) the level of circulating antibody to the replication-competent, recombinant oncolytic vaccinia virus in the individual is at or just past its peak, administering a synthetic analog of 2'-deoxy-guanosine. For example, a method of the present disclosure can comprise: a) administering to an individual in need thereof an effective amount of a replication-competent, recombinant oncolytic vaccinia virus of the present disclosure; and b) administering to the individual an effective amount of a synthetic analog of 2'-deoxy-guanosine, where the administration step (b) is carried out from 5 days to 20 days (e.g., 5 days, 6 days, 7 days, 8 days, 9 days, 10 days, 11 days, 12 days, 13 days, 14 days, 15 days, 16 days, 17 days, 18 days, 19 days, or 20 days) after step (a).

Suitable synthetic analogs of 2'-deoxy-guanosine include, e.g., acyclovir (acycloguanosine), 5'-iododeoxyuridine (also referred to as "idoxuridine"), ganciclovir, valganciclovir, famciclovir, valaciclovir, 2'-fluoro-2'-deoxy-5-iodo-1-beta-d-arabinofuranosyluracil (FIAU), and the like. The structures of suitable synthetic analogs of 2'-deoxy-guanosine are shown below.

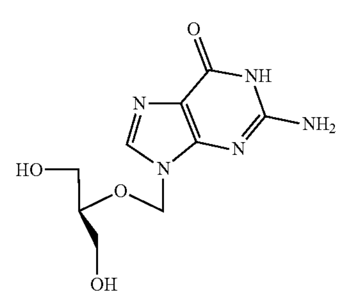

ganciclovir

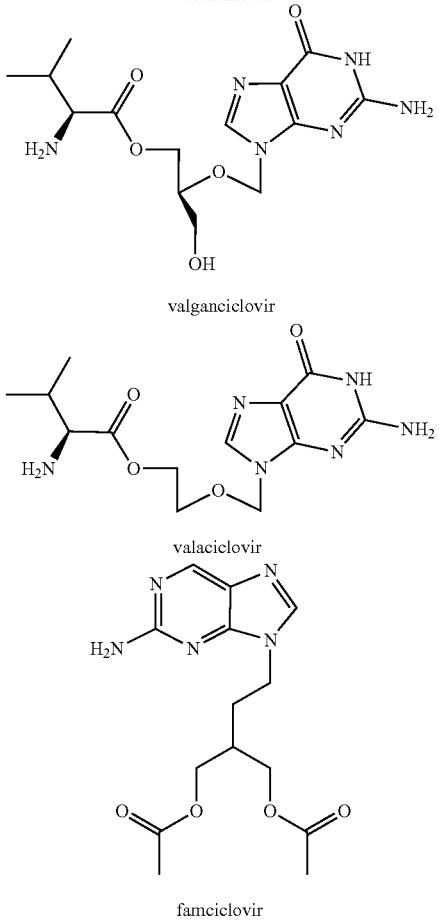

valganciclovir valaciclovir famciclovir

In some cases, a synthetic analog of 2'-deoxy-guanosine is administered in a dose of less than 4000 mg per day orally. In some cases, a suitable oral dose of a synthetic analog of 2'-deoxy-guanosine is in the range of from about 50 mg per day to about 2500 mg per day, e.g., from about 50 mg per day to about 100 mg per day, from about 100 mg per day to about 200 mg per day, from about 200 mg per day to about 300 mg per day, from about 300 mg per day to about 400 mg per day, from about 400 mg per day to about 500 mg per day, from about 500 mg per day to about 600 mg per day, from about 600 mg per day to about 700 mg per day, from about 700 mg per day to about 800 mg per day, from about 800 mg per day to about 900 mg per day, from about 900 mg per day to about 1000 mg per day, from about 1000 mg per day to about 1250 mg per day, from about 1250 mg per day to about 1500 mg per day, from about 1500 mg per day to about 1750 mg per day, from about 1750 mg per day to about 2000 mg per day, from about 2000 mg per day to about 2250 mg per day, or from about 2250 mg per day to about 2500 mg per day. In some cases, a suitable oral dose of a synthetic analog of 2'-deoxy-guanosine is in the range of from about 2500 mg per day to about 3000 mg per day, from about 3000 mg per day to about 3500 mg per day, or from about 3500 mg per day to about 4000 mg per day.

As one non-limiting example, ganciclovir administered in a dose of 1000 mg 3 times per day, for a total daily dose of 3000 mg. Ganciclovir can be administered in a total daily dose of less than 3000 mg (e.g., from about 50 mg per day to about 2500 mg per day, e.g., from about 50 mg per day to about 100 mg per day, from about 100 mg per day to about 200 mg per day, from about 200 mg per day to about 300 mg per day, from about 300 mg per day to about 400 mg per day, from about 400 mg per day to about 500 mg per day, from about 500 mg per day to about 600 mg per day, from about 600 mg per day to about 700 mg per day, from about 700 mg per day to about 800 mg per day, from about 800 mg per day to about 900 mg per day, from about 900 mg per day to about 1000 mg per day, from about 1000 mg per day to about 1250 mg per day, from about 1250 mg per day to about 1500 mg per day, from about 1500 mg per day to about 1750 mg per day, from about 1750 mg per day to about 2000 mg per day, from about 2000 mg per day to about 2250 mg per day, or from about 2250 mg per day to about 2500 mg per day). In some cases, ganciclovir is administered via oral administration.

As another non-limiting example, acyclovir can be administered in a total daily dose of from 1000 mg to 4000 mg. Acyclovir can be administered in a total daily dose of less than 4000 mg (e.g., from about 50 mg per day to about 2500 mg per day, e.g., from about 50 mg per day to about 100 mg per day, from about 100 mg per day to about 200 mg per day, from about 200 mg per day to about 300 mg per day, from about 300 mg per day to about 400 mg per day, from about 400 mg per day to about 500 mg per day, from about 500 mg per day to about 600 mg per day, from about 600 mg per day to about 700 mg per day, from about 700 mg per day to about 800 mg per day, from about 800 mg per day to about 900 mg per day, from about 900 mg per day to about 1000 mg per day, from about 1000 mg per day to about 1250 mg per day, from about 1250 mg per day to about 1500 mg per day, from about 1500 mg per day to about 1750 mg per day, from about 1750 mg per day to about 2000 mg per day, from about 2000 mg per day to about 2250 mg per day, or from about 2250 mg per day to about 2500 mg per day). In some cases, acyclovir is administered via oral administration.

As another example valganciclovir is administered in a total daily dose of from about 900 mg to about 1800 mg. Valganciclovir can be administered in a total daily dose of less than 1800 mg (e.g., from about 500 mg/day to about 600 mg/day, from about 600 mg/day to about 700 mg/day, from about 700 mg/day to about 800 mg/day, from about 800 mg/day to about 900 mg/day, from about 900 mg/day to about 1000 mg/day, from about 1000 mg/day to about 1200 mg/day, from about 1200 mg/day to about 1400 mg/day, or from about 1400 mg/day to about 1600 mg/day). In some cases, valganciclovir is administered via oral administration.

As another example, famciclovir is administered in a total daily dose of from about 2000 mg/day to about 4000 mg/day. Famciclovir can be administered in a total daily dose of less than 4000 mg (e.g., from about 50 mg per day to about 2500 mg per day, e.g., from about 50 mg per day to about 100 mg per day, from about 100 mg per day to about 200 mg per day, from about 200 mg per day to about 300 mg per day, from about 300 mg per day to about 400 mg per day, from about 400 mg per day to about 500 mg per day, from about 500 mg per day to about 600 mg per day, from about 600 mg per day to about 700 mg per day, from about 700 mg per day to about 800 mg per day, from about 800 mg per day to about 900 mg per day, from about 900 mg per day to about 1000 mg per day, from about 1000 mg per day to about 1250 mg per day, from about 1250 mg per day to about 1500 mg per day, from about 1500 mg per day to about 1750 mg per day, from about 1750 mg per day to about 2000 mg per day, from about 2000 mg per day to about 2250 mg per day, or from about 2250 mg per day to about 2500 mg per day). In some cases, famciclovir is administered via oral administration.

As another example valacyclovir is administered in a total daily dose of from about 2000 mg to about 4000 mg. Valacyclovir can be administered in a total daily dose of less than 4000 mg (e.g., from about 50 mg per day to about 2500 mg per day, e.g., from about 50 mg per day to about 100 mg per day, from about 100 mg per day to about 200 mg per day, from about 200 mg per day to about 300 mg per day, from about 300 mg per day to about 400 mg per day, from about 400 mg per day to about 500 mg per day, from about 500 mg per day to about 600 mg per day, from about 600 mg per day to about 700 mg per day, from about 700 mg per day to about 800 mg per day, from about 800 mg per day to about 900 mg per day, from about 900 mg per day to about 1000 mg per day, from about 1000 mg per day to about 1250 mg per day, from about 1250 mg per day to about 1500 mg per day, from about 1500 mg per day to about 1750 mg per day, from about 1750 mg per day to about 2000 mg per day, from about 2000 mg per day to about 2250 mg per day, or from about 2250 mg per day to about 2500 mg per day). In some cases, valacyclovir is administered via oral administration.

As another example, ganciclovir is administered in a total daily dose of about 10 mg/kg. Ganciclovir can be administered in a total daily dose of less than 10 mg/kg (e.g., from about 1 mg/kg to about 2 mg/kg, from about 2 mg/kg to about 3 mg/kg, from about 3 mg/kg to about 4 mg/kg, from about 4 mg/kg to about 5 mg/kg, from about 5 mg/kg to about 6 mg/kg, from about 6 mg/kg to about 7 mg/kg, from about 7 mg/kg to about 8 mg/kg, or from about 8 mg/kg to about 9 mg/kg). In some cases, ganciclovir is administered via injection (e.g., intramuscular injection, intravenous injection, or subcutaneous injection).

As another example, acyclovir is administered in a total daily dose of from about 15 mg/kg to about 30 mg/kg, or from about 30 mg/kg to about 45 mg/kg. Acyclovir can be administered in a total daily dose of less than 45 mg/kg (e.g., from about 5 mg/kg to about 7.5 mg/kg, from about 7.5 mg/kg to about 10 mg/kg, from about 10 mg/kg to about 12.5 mg/kg, from about 12.5 mg/kg to about 15 mg/kg, from about 15 mg/kg to about 20 mg/kg, from about 20 mg/kg to about 25 mg/kg, from about 25 mg/kg to about 30 mg/kg, or from about 30 mg/kg to about 35 mg/kg. In some cases, acyclovir is administered via injection (e.g., intramuscular injection, intravenous injection, or subcutaneous injection).

As another example, valganciclovir is administered in a total daily dose of about 10 mg/kg. Valganciclovir can be administered in a total daily dose of less than 10 mg/kg (e.g., from about 1 mg/kg to about 2 mg/kg, from about 2 mg/kg to about 3 mg/kg, from about 3 mg/kg to about 4 mg/kg, from about 4 mg/kg to about 5 mg/kg, from about 5 mg/kg to about 6 mg/kg, from about 6 mg/kg to about 7 mg/kg, from about 7 mg/kg to about 8 mg/kg, or from about 8 mg/kg to about 9 mg/kg). In some cases, valganciclovir is administered via injection (e.g., intramuscular injection, intravenous injection, or subcutaneous injection).

In some cases, a synthetic analog of 2'-deoxy-guanosine is administered topically. Formulations suitable for topical administration include, e.g., dermal formulations (e.g., liquids, creams, gels, and the like) and ophthalmic formulations (e.g., creams, liquids, gels, and the like). Topical doses of ganciclovir can be, e.g., 1 drop of a 0.15% formulation 5 times per day, e.g., for ophthalmic indications. Topical doses of acyclovir can be, e.g., application 6 times per day of a 5% formulation in an amount sufficient to cover a skin lesion. Topical doses of idoxuridine can be, e.g., application every 4 hours of 1 drop of a 0.5% ointment or a 0.1% cream.

In some cases, a synthetic analog of 2'-deoxy-guanosine is administered in a dose less than 10 mg/kg body weight intravenously. In some cases, a suitable intravenous dose of a synthetic analog of 2'-deoxy-guanosine is in the range of from about 1 mg/kg body weight to about 2.5 mg/kg body weight, from about 2.5 mg/kg body weight to about 5 mg/kg body weight, from about 5 mg/kg body weight to about 7.5 mg/kg body weight, or from about 7.5 mg/kg body weight to about 10 mg/kg body weight.

Cancers

Cancer cells that may be treated by methods and compositions of the present disclosure include cells from the bladder, blood, bone, bone marrow, brain, breast, colon, esophagus, gastrointestine, gum, head, kidney, liver, lung, nasopharynx, neck, ovary, prostate, skin, stomach, spinal cord, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma;

hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; pancreatic cancer; rectal cancer; and hairy cell leukemia.

Tumors that can be treated using a method of the present disclosure include, e.g., a brain cancer tumor, a head and neck cancer tumor, an esophageal cancer tumor, a skin cancer tumor, a lung cancer tumor, a thymic cancer tumor, a stomach cancer tumor, a colon cancer tumor, a liver cancer tumor, an ovarian cancer tumor, a uterine cancer tumor, a bladder cancer tumor, a testicular cancer tumor, a rectal cancer tumor, a breast cancer tumor, or a pancreatic cancer tumor.

In some cases, the tumor is a colorectal adenocarcinoma. In some cases, the tumor is non-small cell lung carcinoma. In some cases, the tumor is a triple-negative breast cancer. In some cases, the tumor is a solid tumor. In some cases, the tumor is a liquid tumor. In some cases, the tumor is recurrent. In some cases, the tumor is a primary tumor. In some cases, the tumor is metastatic.

Detection

The present disclosure provides a method of detecting a replication-competent, recombinant oncolytic vaccinia virus of the present disclosure in a tissue, organ, or fluid in an individual. For example, a replication-competent, recombinant oncolytic vaccinia virus of the present disclosure can be detected in an individual after the vaccinia virus has been administered to the individual. The detection can be carried out to determine whether the replication-competent, recombinant oncolytic vaccinia virus is present at or near the intended target (e.g., at or near a tumor). The detection can be carried out to determine the distribution of the replication-competent, recombinant oncolytic vaccinia virus in various tissues, organs, and fluids of the individual. The detection can be carried out to determine whether, and/or to what degree, the administered replication-competent, recombinant oncolytic vaccinia virus is replicating.

A detection method of the present disclosure can comprise: a) administering to an individual, to whom a replication-competent, recombinant oncolytic vaccinia virus of the present disclosure has been administered, a detectably labeled synthetic analog of 2'-deoxy-guanosine; and b) detecting the detectably labeled synthetic analog in the individual in vivo. A detection method of the present disclosure can comprise: a) administering to an individual, to whom a replication-competent, recombinant oncolytic vaccinia virus of the present disclosure has been administered, a detectably labeled synthetic analog of 2'-deoxy-guanosine; and b) detecting the detectably labeled synthetic analog in a biological sample (e.g., a tissue, organ, or fluid) obtained from the individual. Detection of a replication-competent, recombinant oncolytic vaccinia virus of the present disclosure can comprise detecting activity of the variant TK encoded by the vaccinia virus.

Detectably labeled synthetic analogs of 2'-deoxy-guanosine include radiolabelled versions of any synthetic analog of 2'-deoxy-guanosine. Suitable radiolabels include, e.g., $^{131}$I, $^{14}$C, $^{18}$F, $^{64}$Cu, $^{99m}$Te, $^{11}$C, $^{124}$I, $^{123}$I, $^{15}$O, $^{13}$N, $^{82}$RbCl, and the like. For example, a suitable detectably labeled analog is radiolabelled (e.g., $^{131}$I labeled) 2'-fluoro-2'-deoxy-5-iodo-1-beta-d-arabinofuranosyluracil (FIAU). As another example, a suitable detectably labeled analog is 9-[(3-[$^{18}$F]fluoro-1-hydroxy-2-propoxy)methyl]guanine ([$^{18}$F]FHPG. As another example, a suitable detectably labeled analog is radioiodinated (E)-5-(2-iodovinyl)-2'-fluoro-2'-deoxyuridine (IVFRU).

The detectably labeled HSV-TK substrate can be a detectably labeled version of a compound selected from FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpryrimidine-2,4(1H,-3H)-dione), ganciclovir, valganciclovir, acyclovir, valacyclovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains.

Suitable methods for detecting a detectably labeled synthetic analog in an individual in vivo include, e.g., positron emission tomography (PET), magnetic resonance imaging (MRI), single-photon emission computerized tomography (SPECT), computed tomography (CT), and the like.

As noted above, in some cases, the detection comprises detecting the replication-competent, recombinant oncolytic vaccinia virus (e.g., detecting variant TK activity) in a biological sample obtained from an individual.

Suitable biological samples include but are not limited to saliva, blood, serum, plasma, urine, aspirate, and biopsy samples. Thus, the term "biological sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; by washing; or by enrichment for certain cell populations, such as cancer cells. The definition also includes samples that have been enriched for particular types of molecules. The term "biological sample" encompasses biological samples such as a clinical sample such as blood, plasma, serum, aspirate, cerebral spinal fluid (CSF), vitreal fluid, aqueous fluid, synovial fluid, and the like; and also includes tissue obtained by surgical resection, tissue obtained by biopsy, cells in culture, cell supernatants, cell lysates, tissue samples, organs, bone marrow, and the like. A "biological sample" includes biological fluids derived from cells, organs, or tissues (e.g., biological fluids derived from cancer cells, tumors, etc.). Suitable biological samples include, e.g., a tumor biopsy, fluid surrounding a tumor, blood, serum, plasma, pleural fluid, ascites, an organ, a tissue, and the like. The biological sample can include cells, or may be acellular.

Detection of a replication-competent, recombinant oncolytic vaccinia virus of the present disclosure in an individual (in vivo) or in a biological sample obtained from the individual can be carried out at any time after the replication-competent, recombinant oncolytic vaccinia virus has been administered to the individual. For example, detection of a replication-competent, recombinant oncolytic vaccinia virus of the present disclosure in an individual (in vivo) or in a biological sample obtained from the individual can be carried out from 1 day to 7 days, from 1 week to 4 weeks, from 4 weeks to 1 month, from 1 month to 3 months, from 3 months to 6 months, from 6 months to 1 year, or more than 1 year, after the replication-competent, recombinant oncolytic vaccinia virus has been administered to the individual.

Subjects Suitable for Treatment

A variety of subjects are suitable for treatment with a subject method of treating cancer. Suitable subjects include any individual, e.g., a human or non-human animal who has cancer, who has been diagnosed with cancer, who is at risk for developing cancer, who has had cancer and is at risk for recurrence of the cancer, who has been treated with an agent other than an oncolytic vaccinia virus of the present disclosure for the cancer and failed to respond to such treatment, or who has been treated with an agent other than an oncolytic vaccinia virus of the present disclosure for the cancer but relapsed after initial response to such treatment.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-41 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A replication-competent, recombinant oncolytic vaccinia virus comprising a nucleotide sequence encoding a heterologous thymidine kinase (TK) polypeptide, wherein the heterologous TK polypeptide is capable of catalyzing phosphorylation of deoxyguanosine.

Aspect 2. The replication-competent, recombinant oncolytic vaccinia virus of aspect 1, wherein the vaccinia virus comprises a modification that results in a lack of thymidine kinase expression or function.

Aspect 3. The replication-competent, recombinant oncolytic vaccinia virus of aspect 1 or 2, wherein the heterologous TK polypeptide is a variant herpes simplex virus (HSV) TK polypeptide Aspect 4. The replication-competent, recombinant oncolytic vaccinia virus of aspect 3, wherein the variant HSV TK polypeptide comprises an amino acid sequence having at least 80% amino acid sequence identity to wild-type HSV TK, and comprises a substitution of one or more of L159, I160, F161, A168, and L169, based on the amino acid numbering of wild-type HSV TK amino acid sequence of SEQ ID NO: 1.

Aspect 5. The replication-competent, recombinant oncolytic vaccinia virus of aspect 4, wherein the variant HSV TK polypeptide comprises an A168H substitution.

Aspect 6. The replication-competent, recombinant oncolytic vaccinia virus of aspect 4, wherein the variant HSV TK polypeptide comprises an L159I substitution, an I160L substitution, an F161A substitution, an A168Y substitution, and an L169F substitution.

Aspect 7. The replication-competent, recombinant oncolytic vaccinia virus of aspect 4, wherein the variant TK polypeptide comprises an L159I substitution, an I160F substitution, an F161L substitution, an A168F substitution, and an L169M substitution.

Aspect 8. The replication-competent, recombinant oncolytic vaccinia virus of aspect 3, wherein the variant HSV TK polypeptide comprises the amino acid sequence of SEQ ID NO: 2, 3 or 4.

Aspect 9. The replication-competent, recombinant oncolytic vaccinia virus of any one of aspects 1-8, wherein the vaccinia virus is a Copenhagen strain vaccinia virus.

Aspect 10. The replication-competent, recombinant oncolytic vaccinia virus of any one of aspects 1-8, wherein the vaccinia virus is a WR strain vaccinia virus.

Aspect 11. The replication-competent, recombinant oncolytic vaccinia virus of any one of aspects 1-10, wherein the vaccinia virus comprises a deletion of all or a portion of a vaccinia virus gene.

Aspect 12. The replication-competent, recombinant oncolytic vaccinia virus of any one of aspects 1-11, wherein the vaccinia virus comprises one or more amino acid substitutions that enhance production of extracellular enveloped virus.

Aspect 13. The replication-competent, recombinant oncolytic vaccinia virus of aspect 10, wherein the vaccinia virus comprises an A34R gene that encodes an A34 polypeptide comprising a K151E substitution.

Aspect 14. The replication-competent, recombinant oncolytic vaccinia virus of any one of aspects 1-13, wherein the vaccinia virus comprises a heterologous nucleic acid comprising a nucleotide sequence encoding an immunomodulatory polypeptide.

Aspect 15. A composition comprising: a) the vaccinia virus of any one of aspects 1-12; and b) a pharmaceutically acceptable excipient.

Aspect 16. A method of inducing oncolysis in an individual having a tumor, the method comprising administering to the individual an effective amount of the vaccinia virus of any one of aspects 1-14, or the composition of aspect 15.

Aspect 17. The method of aspect 16, wherein said administering comprises administering a single dose of the virus or the composition.

Aspect 18. The method of aspect 17, wherein the single dose comprises at least $10^6$ plaque forming units (pfu) of the vaccinia virus.

Aspect 19. The method of aspect 17, wherein the single dose comprises from $10^9$ to $10^{12}$ pfu of the vaccinia virus.

Aspect 20. The method of aspect 16, wherein said administering comprises administering multiple doses of the vaccinia virus or the composition.

Aspect 21. The method of aspect 20, wherein the vaccinia virus or composition is administered every other day.

Aspect 22. The method of any one of aspects 16-21, wherein the vaccinia virus or the composition is administered once per week.

Aspect 23. The method of any one of aspects 16-21, wherein the vaccinia virus or the composition is administered every other week.

Aspect 24. The method of any one of aspects 16-23, wherein the tumor is a brain cancer tumor, a head and neck cancer tumor, an esophageal cancer tumor, a skin cancer tumor, a lung cancer tumor, a thymic cancer tumor, a stomach cancer tumor, a colon cancer tumor, a liver cancer tumor, an ovarian cancer tumor, a uterine cancer tumor, a bladder cancer tumor, a testicular cancer tumor, a rectal cancer tumor, a breast cancer tumor, or a pancreatic cancer tumor.

Aspect 25. The method of any one of aspects 16-23, wherein the tumor is a colorectal adenocarcinoma.

Aspect 26. The method of any one of aspects 16-23, wherein the tumor is non-small cell lung carcinoma.

Aspect 27. The method of any one of aspects 16-23, wherein the tumor is a triple-negative breast cancer.

Aspect 28. The method of any one of aspects 16-23, wherein the tumor is a solid tumor.

Aspect 29. The method of any one of aspects 16-23, wherein the tumor is a liquid tumor.

Aspect 30. The method of any one of aspects 16-29, wherein the tumor is recurrent.

Aspect 31. The method of any one of aspects 16-29, wherein the tumor is a primary tumor.

Aspect 32. The method of any one of aspects 16-29, wherein the tumor is metastatic.

Aspect 33. The method of any one of aspects 16-32, further comprising administering to the individual a second cancer therapy.

Aspect 34. The method of aspect 33, wherein the second cancer therapy is selected from chemotherapy, biological therapy, radiotherapy, immunotherapy, hormone therapy, anti-vascular therapy, cryotherapy, toxin therapy, oncolytic virus therapy, a cell therapy, and surgery.

Aspect 35. The method of aspect 33, wherein the second cancer therapy comprises an anti-PD1 agent or an anti-PD-L1 agent.

Aspect 36. The method of any one of aspects 16-35, wherein the individual is immunocompromised.

Aspect 37. The method of any one of aspects 16-35, wherein said administering of the vaccinia virus or the composition is intratumoral.

Aspect 38. The method of any one of aspects 16-35, wherein said administering of the vaccinia virus or the composition is peritumoral.

Aspect 39. The method of any one of aspects 16-35, wherein said administering of the vaccinia virus or the composition is intravenous.

Aspect 40. The method of any one of aspects 16-35, wherein said administering of the vaccinia virus or the composition is intra-arterial, intraperitoneal, intrabladder, or intrathecal.

Aspect 41. The method of any one of aspects 16-40, comprising administering to the individual an amount of ganciclovir that, in combination with the vaccinia virus, is effective to reduce an adverse side effect of the vaccinia virus.

Aspect 42. The method of aspect 41, wherein the side effect is a skin lesion.

Aspect 43. A replication-competent, recombinant oncolytic vaccinia virus comprising a nucleotide sequence encoding a variant herpes simplex virus (HSV) TK polypeptide comprising the amino acid sequence of SEQ ID NO: 2, 3 or 4.

Aspect 44. A replication-competent, recombinant oncolytic vaccinia virus comprising a nucleotide sequence encoding a variant herpes simplex virus (HSV) TK polypeptide comprising the amino acid sequence of SEQ ID NO: 2, 3 or 4, wherein the vaccinia virus is a Copenhagen strain vaccinia virus and comprises an A34R gene comprising a K151E substitution.

Aspect 45. A replication-competent, recombinant oncolytic vaccinia virus comprising a variant herpes simplex virus (HSV) TK polypeptide nucleotide sequence comprising SEQ ID NO: 11, 12 or 13.

Aspect 46. A composition, comprising: (i) the vaccinia virus of any one of claims 43-45, and (ii) a pharmaceutically acceptable carrier.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

Materials and Methods

Plasmid Construction

Figure 1:
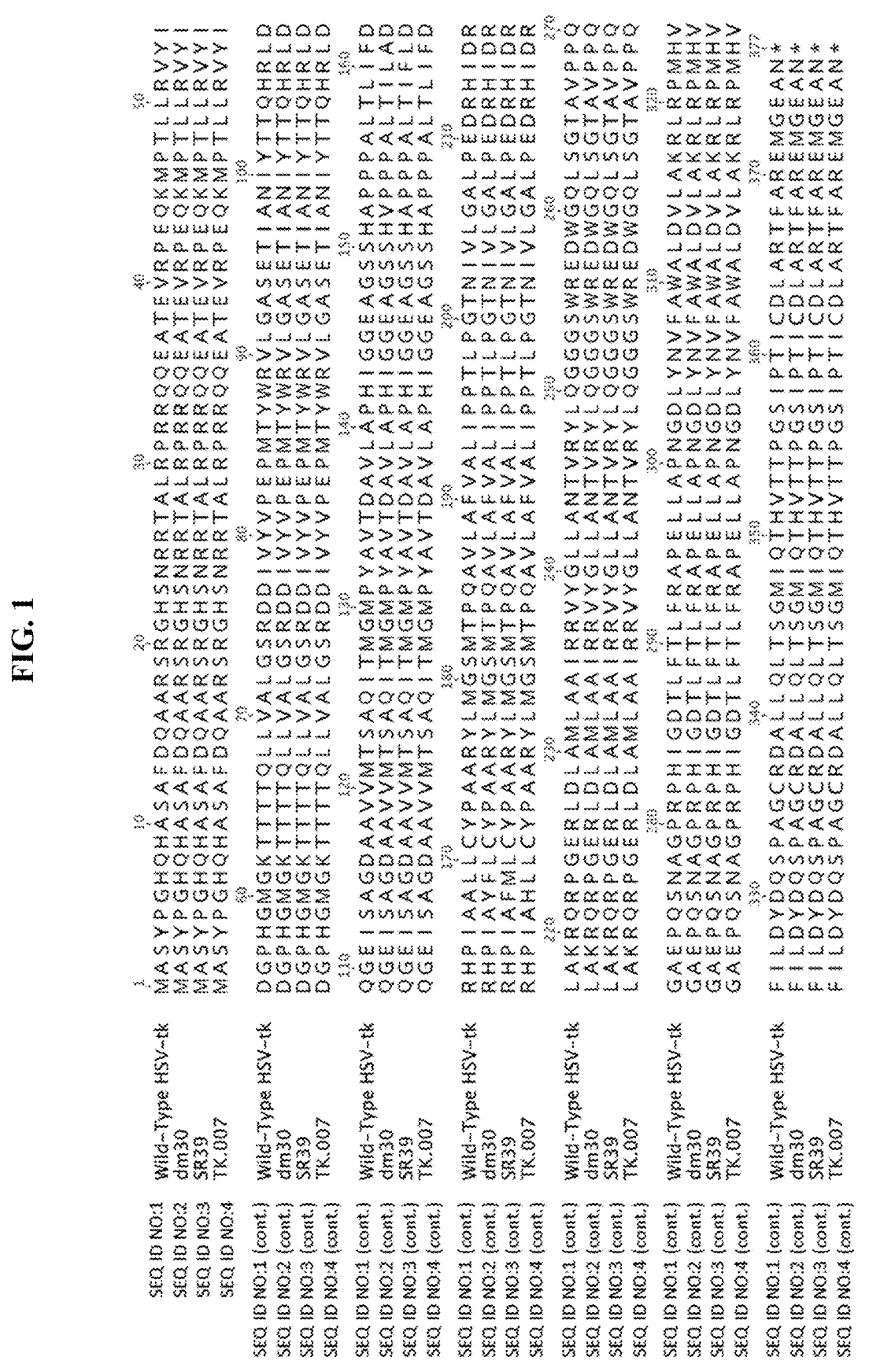

Plasmids containing WT HSV-TK, dm30 HSV-TK variant, SR39 HSV-TK variant, or TK.007 HSV-TK variant were generated using gene synthesis techniques. A sequence encoding WT HSV-TK, dm30 HSV-TK, SR39 HSV-TK, or TK.007 HSV-TK, controlled by the pSEL promoter, was codon optimized for vaccinia virus expression, submitted to GenScript for gene synthesis, and inserted into the pUC57-mini vector. The amino acid sequence of WT HSV-TK, dm30 HSV-TK, SR39 HSV-TK, or TK.007 is annotated in FIG. 1 as SEQ ID NO:1, 2, 3, and 4, respectively. An alignment of amino acids 151-175 of WT HSV-TK, dm30 HSV-Tk, SR39 HSV-TK, or TK.007 is annotated in FIG. 2 as SEQ ID NO:5, 6, 7 and 8, respectively. The pSEL promoter has the following nucleotide sequence: aaaaattgaaatttattttttttttttggaatataaata (SEQ ID NO:9).

Features of certain vaccinia virus constructs generated in connection with the examples provided below are summarized in Table 1, below.

TABLE 1

Features of Certain Recombinant Vaccinia Virus Constructs

| Vaccinia Virus Construct ID# | Strain | Transgene 1 | Transgene 1 location | Transgene 2 | Transgene 2 location | Other Deletions |
|---|---|---|---|---|---|---|
| IGV-006 | Cop | Luc-GFP | J2R (deletion) | | | |
| IGV-023 | Cop | HSV TK | J2R (deletion) | | | |
| IGV-033 | Cop | HSV TK SR39 | J2R (deletion) | | | |
| IGV-034 | Cop | HSV TK dm30 | J2R (deletion) | | | |
| IGV-035 | Cop | HSV TK.007 | J2R (deletion) | | | |
| IGV-077 | Cop | HSV TK.007 | J2R (deletion) | Luc-GFP | B19R (deletion) | C11R |

Viruses and Cells

Wild-type poxvirus strain Copenhagen was used as an initial vector for further modifications. Vaccinia virus IGV-006 was constructed by insertion of a luciferase-2A-green fluorescent protein (GFP) cassette under the control of the pSEL promoter into the thymidine kinase gene (J2R region) of the Copenhagen strain of vaccinia virus. The expression of the luciferase reporter gene was confirmed by luminescence using the Bright-Glo™ Luciferase Assay System (Promega) and a Spectramax M5 (Molecular Devices). GFP expression was confirmed via fluorescent microscopy.

Vaccinia strains expressing WT HSV-TK (IGV-023), TK.007 HSV-TK (IGV-035), SR39 HSV-TK (IGV-034), and dm30 HSV-TK (IGV-033) were constructed by recombination of the synthesized HSV-TK gene under the control of the pSEL promoter into the thymidine kinase region of IGV-006. Successful insertion of the HSV-TK gene into the IGV-006 thymidine kinase region was verified by Sanger sequencing and sensitivity to ganciclovir. Viruses were amplified and purified as described below.

HeLa and BSC-40 cells were obtained from ATCC. A549, Colo205, and MDA MB 231 cells were obtained from the NCI DCTD Repository of Tumors and Tumor Cell Lines. HMEC and SAEC cells were obtained from Lonza. HeLa S3 and VeroB4 cells were obtained from DSMZ.

Virus Amplification and Purification

HeLa S3 cells (DSMZ) were infected by adding virus and incubating for 1 hour. Following infection, the media was replaced with fresh media and incubated for 48 hours to allow for virus amplification. Following incubation, the cells were harvested and collected by centrifugation. Cells were lysed by mechanical disruption with a Dounce homogenizer (Wheaton). Virus purification was accomplished with a 24% to 40% sucrose gradient and ultracentrifugation. Purified virus was stored at −80° C. and titered in duplicate by adding serial dilutions of purified virus to BSC-40 cells (ATCC) as previously described (Cotter et al. (2015) *Current Protocols in Microbiology* 39:14A.3.1-14A.3.18).

Virus Titering by Plaque Assay

Virus titer was determined by ten-fold serial dilutions, with a final dilution of $10^{-9}$ of the stock concentrated, purified virus. The virus dilutions were used to infect BSC-40 cells to determine the number of plaque forming units per mL (PFU/mL). 1 mL of each serial dilution was applied in duplicate to wells containing a confluent monolayer of BSC-40 cells in a standard 6-well microplate (BD Falcon). Cells were infected for an hour, washed with fresh media, and overlaid with a solution of fresh media containing 1.5% carboxymethylcellulose (Teknova). Following 48 hours of incubation, the media was removed, and the cells were fixed and stained with a 20% ethanol solution containing 0.1% crystal violet (Sigma). The stock titer was then determined by counting the number of plaques in each well, averaging between duplicate titers, and adjusting for the dilution factor.

One-Step Growth Curve

Virus replication was determined by infecting a monolayer of HeLa cells (ATCC) with virus at a multiplicity of infection (MOI) of 3 for 1 hour in triplicate. Following infection, the viral inoculum was replaced with fresh media. Cells were harvested into media and frozen at −80° C. at 12, 18, 24, 48, and 72 hours post-infection. Viral titer for each sample was determined in duplicate via viral plaque assay.

Sensitivity of Viral Replication to Ganciclovir

Inhibition of viral replication for viruses expressing HSV-TK in the presence of ganciclovir was determined by infecting a monolayer of HeLa cells with virus at an MOI of 3 for 1 hour in triplicate. Following infection, the viral inoculum was replaced with fresh media. The infected HeLa cells were dosed with 0 μM, 0.05 μM, 0.1 μM, 0.25 μM, 0.5 μM, 0.75 μM, or 1 μM of ganciclovir (Calbiochem). Cells were harvested into media and frozen at −80° C. at 48 hours post-infection. Viral titer for each sample was determined in duplicate via viral plaque assay.

Viral Replication in Tumor and Normal Primary Human Cells

Virus replication in the tumor cell lines A549 (NCI), Colo205 (NCI), MDA MB 231 (NCI), and HeLa and primary human cells HMEC (Lonza) and SAEC (Lonza) was determined by infecting a monolayer of cells with virus at an MOI of 1 for 1 hour in triplicate. Following infection, the viral inoculum was replaced with fresh media. Cells were harvested into media and frozen at −80° C. at 24 and 48 hours post-infection. Viral titer for each sample was determined in duplicate via viral plaque assay.

Cytotoxicity Assay in Tumor and Normal Primary Human Cells

Cell killing in the tumor cell lines A549 (NCI), Colo205 (NCI), and MDA MB 231 (NCI), and primary human cells HMEC (Lonza) and SAEC (Lonza) was determined by infecting monolayers of cells with various MOI of virus in quadruplicate for 1 hour. Following infection, the viral inoculum was replaced with fresh media. At 48 hours post-infection, cytotoxicity was determined by LDH release using Cytotox96 assay (Promega) and Spectramax M5 (Molecular Devices) at 490 nm. Data analysis was performed with Prism 7 software.

Animal Model, Tumor Model Preparation, and Test Agent Preparation

Nude BALB/c mice (Charles River Laboratories) were housed in a temperature (68°-79° F.) and humidity (30-70%) controlled facility Animal rooms were maintained on 12-hour alternating light and dark cycles. Dry food (5053 Irradiated Pico Lab Rodent Diet 20) was made available ad libitum throughout acclimation and the biological phase of the study. HCT-116 cells were cultured and implanted (1 million cells in 100 μL) in the right front flank of each mouse. Each animal was dosed intravenously with viral test agent (30 million PFU in 100 μL) when HCT 116 tumor volumes reached 150 to 250 mm$^3$.

In Vivo Imaging

Animals were assessed using bioluminescence imaging (BLI) and positron emission tomography (PET) imaging 3 or 4, and 7 days post-test agent administration. For BLI, animals were injected intraperitoneally then immediately anesthetized with isoflurane gas in oxygen for BLI. Imaging was performed with an IVIS Spectrum (Perkin-Elmer). At each imaging time point, two scaled subject images were generated with VivoQuant (Invicro) for a shielded and unshielded prone- and supine-positioned animal and luciferin radiance determined for regions of interest. Images were generated in units of radiance (photos/second/millimeter$^2$/steradian) and co-registered to white light images for anatomical reference for analysis.

For PET imaging, animals were injected intravenously with $^{18}$F-FHBG under awake conditions before being anesthetized with isoflurane gas in oxygen 105 minutes later and imaged following 120 minutes of $^{18}$F-FHBG uptake time. Imaging was performed with an Inveon (Siemens) multi-modal PET/SPECT/CT imager. Maximum intensity projection (MIP) images were generated using VivoQuant software. Specifically, co-registered PET/CT MIPs were generated for each animal at each time point scaled to a fixed range of 0.1-10% injected dose/g (ID/g). Furthermore, co-registered PET/CT MIPs were generated with gut signal manually removed to better display lower uptake across other regions. These MIPs were scaled to a fixed range of 0.5-3% ID/g and were generated at each imaging time point.

Reconstructed images were generated in units of activity, co-registered to each other, resampled to 0.2 mm$^3$ voxels, and cropped to a uniform size prior to analysis. To estimate tissue uptake of $^{18}$F-FHBG, regions of interest (ROIs) for the muscle (brachial), mandible (left and right), and liver (left and right lobes) were generated by placing fixed volume spherical ROIs in the center of the tissue to encompass areas of representative concentration throughout each respective organ. Whole body ROIs were generated by applying a combination of manual and automated segmentation thresholds to the CT. ROIs for the intestines and gallbladder were generated by using connected thresholding on relevant PET signal in the appropriate region. Tail and tumor ROIs were manually segmented due to the anatomical variability of these regions between subjects.

Organ Sample Collection 7 days post-test agent administration, all animals were humanely euthanized, and tissue resected for further ex vivo analysis. Head, heart, left and right hindlimbs, left and right kidneys, large intestines, liver, lungs, left and right ovaries, small intestines, spleen, tail, and tumor tissues were resected from each animal Following ex vivo analysis, tissue samples were snap frozen in liquid nitrogen and stored at −80° C.

Viral Titering from Tissue Samples

Organ samples were thawed in a room temperature water bath, weighed, and homogenized for 20 seconds at 6,000 RPM twice, with five-minute rest intervals on ice bath between sessions using the BeadRuptor Elite homogenizer (Omni). Reinforced plastic tubes with either 1.4 mm or 2.8 mm ceramic beads were used to homogenize the samples. Samples were then clarified with a 2-minute centrifugation, sonicated and the supernatant was used to titer immediately. Virus titer was determined by ten-fold serial dilutions with a final dilution up to $10^{-6}$. The virus dilutions were used to infect U-2 OS cells in 6-well plates (BD Falcon). Cells were infected with 1 mL of each serial dilution for an hour, washed with fresh media, and overlaid with a solution of fresh media containing 1.5% carboxymethylcellulose (Teknova). Following 48 hours of incubation, the media was removed, and the cells were fixed and stained with a 20% ethanol solution containing 0.1% crystal violet (Sigma). The titer was then determined by counting the number of plaques in each well, averaging between duplicate titers, and adjusting for the dilution factor. The data is expressed in number of plaques forming units per gram of tissue (PFU/gram).

Example 2

Figure 3:
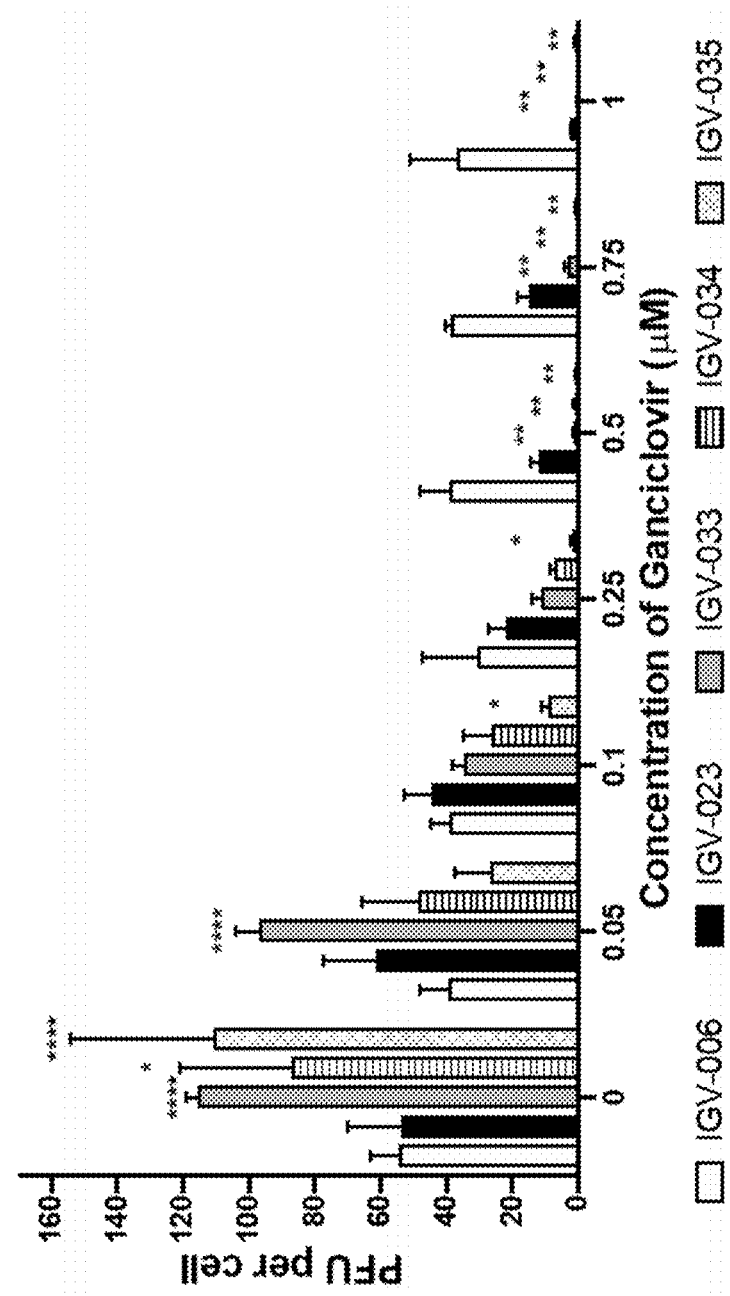
FIG. 3 depicts the effect of HSV-TK on sensitivity of vaccinia virus to ganciclovir in the context of virus replication.
Figure 4D:
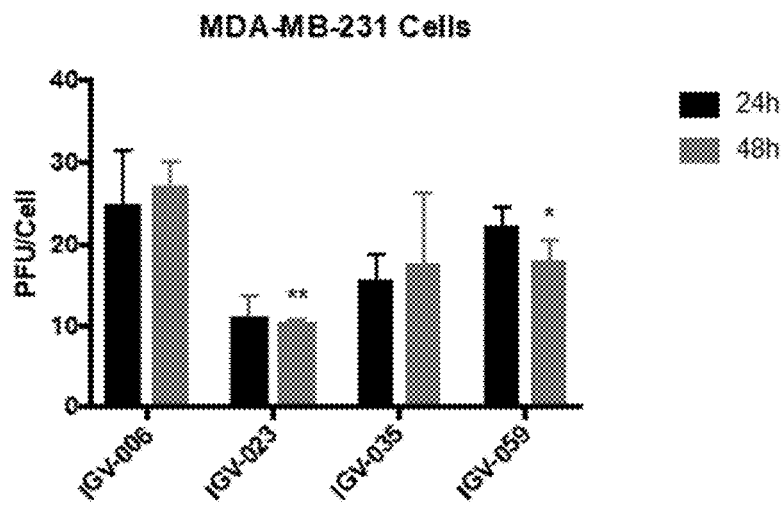
Figure 4E:
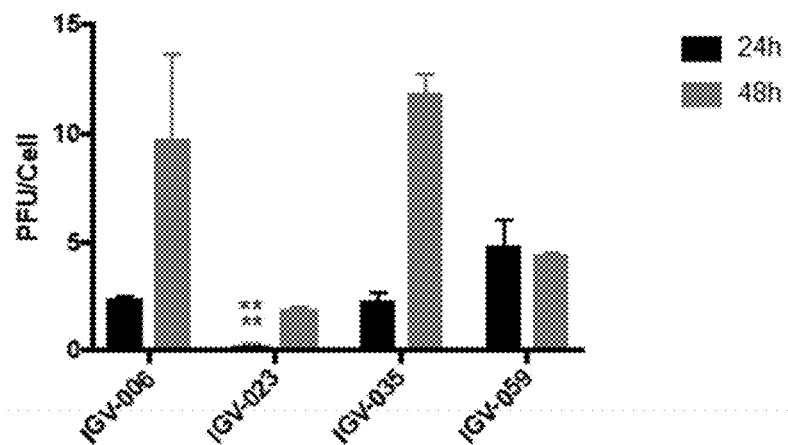
Figure 4F:
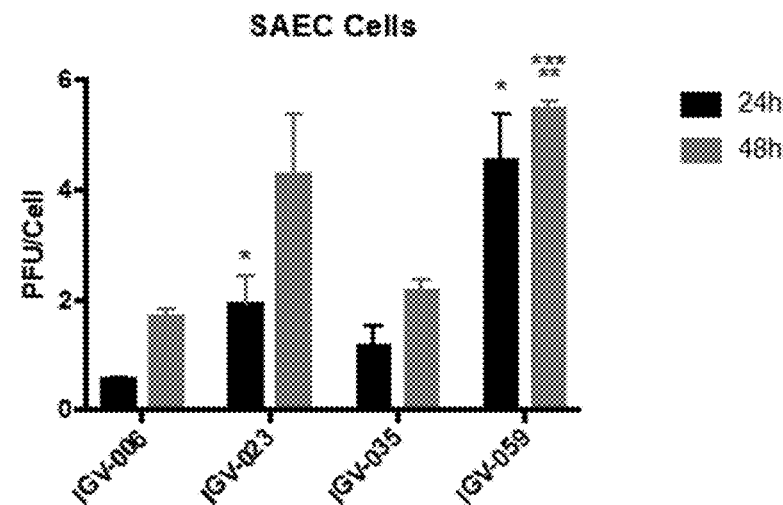

The impact of HSV-TK expression and ganciclovir sensitivity on vaccinia virus replication was assessed in vitro using HeLa cells. Vaccinia viruses expressing the TK.007 HSV-TK variant (IGV-035), the SR39 HSV-TK variant (IGV-034), the dm30 HSV-TK variant (IGV-033), the wild-type HSV-TK (IGV-023), or no HSV-TK control (IGV-006) were generated and manufactured as described in Example 1. HeLa cells were infected with vaccinia viruses expressing the TK.007 HSV-TK variant (IGV-035), the SR39 HSV-TK variant (IGV-034), the dm30 HSV-TK variant (IGV-033), the wild-type HSV-TK (IGV-023), or no HSV-TK control (IGV-006) for 1 hour at 37° C. After the incubation time, the infected cells were washed and overlaid with fresh media with increasing amounts of ganciclovir at concentrations of 0 μM, 0.05 μM, 0.1 μM, 0.25 μM, 0.5 μM, 0.75 μM, and 1 μM. Viral replication was determined at 48 hours post-infection by plaque assay for vaccinia virus titers, as described in Example 1, to determine the number of viral plaque-forming units per cell, which represents the amount of viral replication in each condition. Relative to the no HSV-TK control (IGV-006), the TK.007 HSV-TK variant (IGV-035), the SR39 HSV-TK variant (IGV-034), the dm30 HSV-TK variant (IGV-033), and the wild-type HSV-TK (IGV-023) significantly reduced vaccinia virus replication in the presence of ganciclovir (FIG. 3). In particular, expression of the TK.007 HSV-TK variant significantly reduced vaccinia virus replication at lower concentrations of ganciclovir compared to vaccinia virus expressing variant or wild-type HSV-TK, demonstrating that the TK.007 HSV-TK variant was most sensitive to ganciclovir (FIG. 3). This study illustrates that incorporation of HSV-TK leads to vaccinia virus sensitivity to ganciclovir.

FIG. 3 provides data on HSV-TK conferring sensitivity to ganciclovir in the context of vaccinia virus replication. HeLa cells were infected with vaccinia viruses expressing the TK.007 HSV-TK variant (IGV-035), the SR39 HSV-TK variant (IGV-034), the dm30 HSV-TK variant (IGV-033), the wild-type HSV-TK (IGV-023), or no HSV-TK control (IGV-006) at a MOI of 1.2 hours post-infection, the infected HeLa cells were washed once with fresh media and dosed with ganciclovir at concentrations of 0 µM, 0.05 µM, 0.1 µM, 0.25 µM, 0.5 µM, 0.75 µM, and 1 µM. At 48 hours post infection, vaccinia virus replication was determined by plaque assay. Increasing ganciclovir dose concentration lead to a reduction in vaccinia virus replication for vaccinia virus expressing HSV-TK WT or HSV-TK variants. Vaccinia virus expressing the TK.007 HSV-TK variant had the lowest vaccinia virus production at the lowest concentration of ganciclovir, thus demonstrating the greatest sensitivity to ganciclovir of the vaccinia viruses expressing HSV-TK WT or the HSV-TK variants tested. Error bars indicate SD (n=3). Data were analyzed by two-way analysis of variance (ANOVA) followed by Tukey's multiple comparisons test against no HSV-TK control (IGV-006). (*p<0.05; p<0.01; *p<0.001, ****p<0.0001).

Example 3

The impact of HSV-TK variant expression on vaccinia virus replication was assessed in vitro using representative human cancer cell lines and normal primary human cells. Vaccinia virus expressing the wild-type HSV-TK (IGV-023), the TK.007 HSV-TK variant (IGV-035), no TK control (IGV-006), and wild type vaccinia TK without HSV-TK (IGV-059) were generated and manufactured as described in Example 1. HeLa (cervical cancer), A549 (lung adenocarcinoma), Colo 205 (colon cancer), and MDA-MB-231 (breast cancer) cancer cells and normal primary human mammary epithelial cells (HMEC) and small airway epithelial cells (SAEC) were infected with vaccinia viruses expressing the wild-type HSV-TK (IGV-023), the TK.007 HSV-TK variant (IGV-035), no TK control (IGV-006), and wild type vaccinia TK without HSV-TK (IGV-059). At 24 and 48 hours post-infection, viral replication was determined by viral plaque assay and plaques counted to determine the number of viral plaque-forming units produced per cell, as described in Example 1. Less viral plaque-forming units were produced per normal primary human cell compared to per cancer cell. Furthermore, viruses expressing HSV-TK variants do not replicate significantly more than virus expressing the wild-type vaccinia TK. FIGS. 4A-4F provides data on the effect of HSV-TK expression on vaccinia virus replication in representative human cancer cell lines and normal primary human cells. Cancer cell lines A) A549 (lung adenocarcinoma), B) HeLa (cervical cancer), C) Colo-205 (colon cancer), and D) MDA MB 231 (breast cancer) and E) normal primary human mammary epithelial cells (HMEC) and F) small airway epithelial cells (SAEC) were infected with vaccinia virus expressing wild-type HSV-TK (IGV-023), the TK.007 HSV-TK variant (IGV-035), no HSV-TK or J2R vaccinia TK (IGV-006), or wild type J2R vaccinia TK without HSV-TK (IGV-059) at an MOI of 1. The infected cells were harvested at 24 and 48 hours post-infection. The viral titer of each sample was determined by viral plaque assay and represented by plaque-forming units (pfu) produced per cell. Selectivity of vaccinia virus replication for tumor cells rather than normal cells is maintained with vaccinia virus expressing the TK.007 HSV-TK variant (IGV-035), which shows very similar viral replication compared to vaccinia virus without J2R vaccinia TK (IGV-006) in various cancer and normal human cells tested. Error bars indicate SD (n=3). Asterisks indicate statistical significance against no HSV-TK control (IGV-006) (*p<0.05; p<0.01; *p<0.001; **p<0.0001; ***p<0.00001 Student's t-test).

Example 4

Figure 5A:
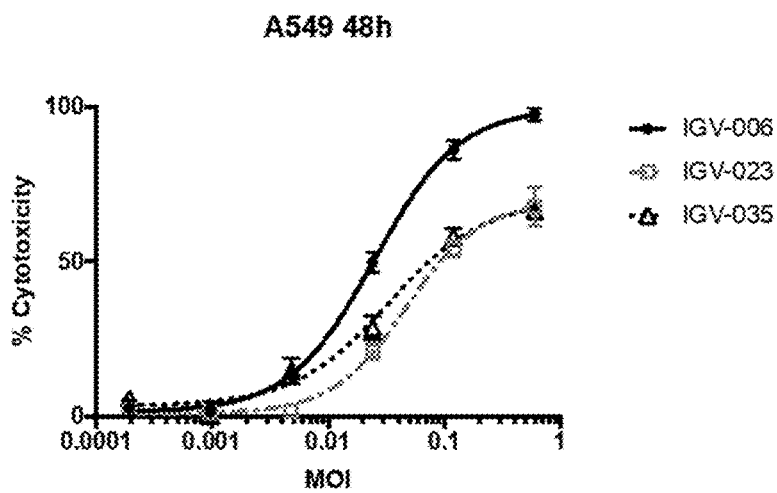
FIGS. 5A-5C depict the effect of HSV-TK expression on vaccinia virus's ability to kill human cancer cells, as assessed by an in vitro cytotoxicity assay.
Figure 5B:
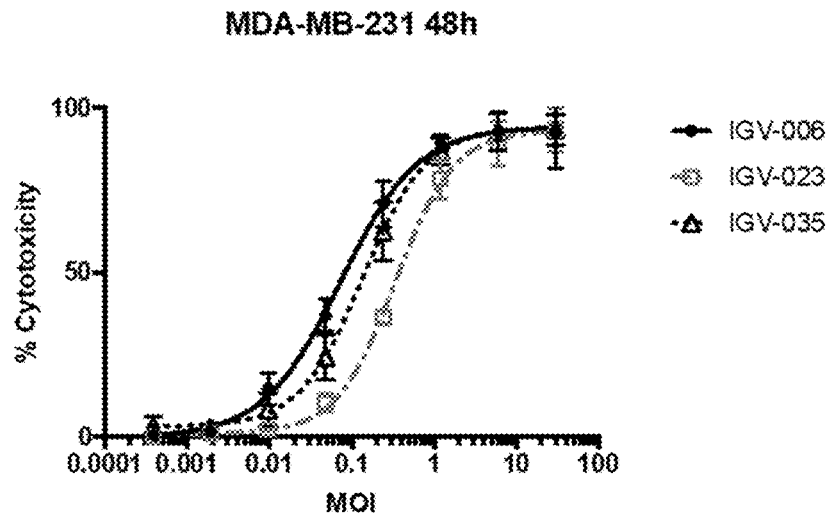
Figure 5C:
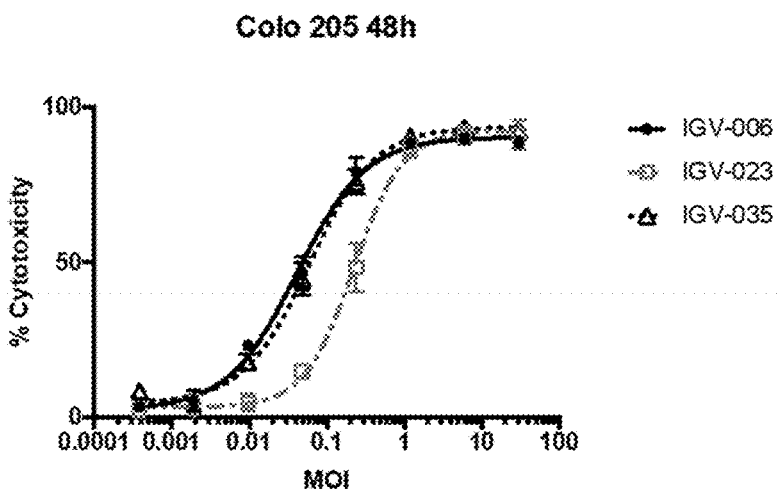
Figure 6A:
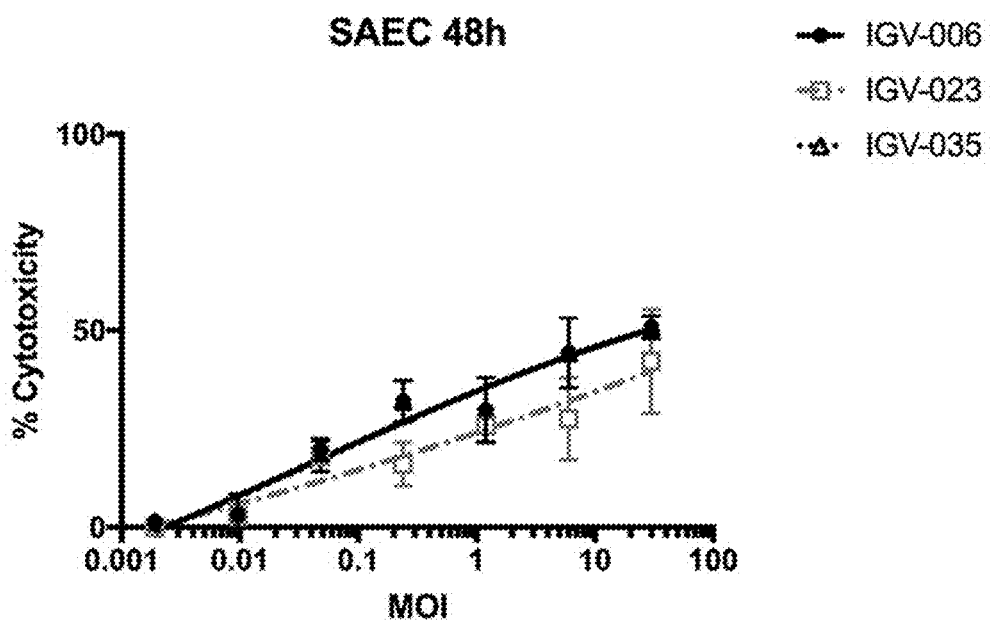
FIGS. 6A and 6B depict the effect of HSV-TK expression on vaccinia virus's ability to kill human normal primary cells, as assessed by an in vitro cytotoxicity assay.
Figure 6B:
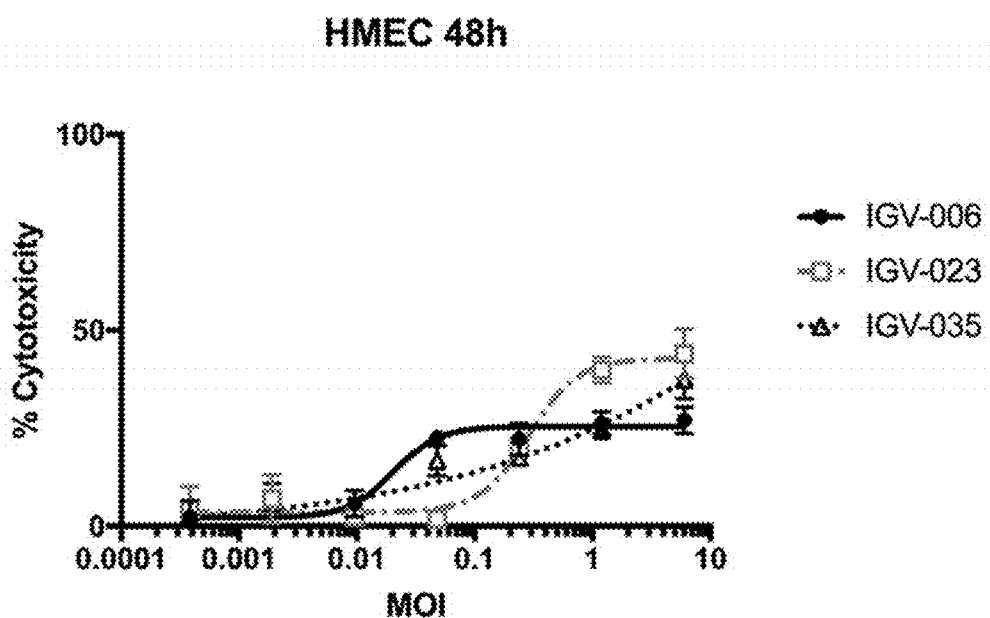

The impact of HSV-TK variant expression on vaccinia virus killing potency targeting cancer cells while sparing normal human cells was assessed in vitro using representative human cancer cell lines and normal primary human cells. Vaccinia virus expressing the wild-type HSV-TK (IGV-023), the TK.007 HSV-TK variant (IGV-035), and no TK control (IGV-006), were generated and manufactured as described in Example 1. A549 (lung adenocarcinoma), Colo 205 (colon cancer), and MDA-MB-231 (breast cancer) human cancer cells and SAEC and HMEC normal primary human cells were infected with vaccinia viruses expressing the wild-type HSV-TK (IGV-023), the TK.007 HSV-TK variant (IGV-035), or no TK control (IGV-006). At 48 hours post-infection, cytotoxicity was determined by LDH release using Cytotox96 assay readout at 490 nm, as described in Example 1. Similar cytotoxicity of the virus expressing the TK.007 HSV-TK variant (IGV-035) compared to the no HSV-TK (IGV-006) was observed in human cancer cells (FIGS. 5A-5C). However, the virus expressing wild-type (HSV-TK) rendered less killing potency than the other two viruses in all cancer cells (FIGS. 5A-5C). In normal cells, all the viruses tested show lower cytotoxicity (FIGS. 6A-6B). These results demonstrate that the TK.007 HSV-TK variant has similar killing potency in human cancer cell lines as a vaccinia virus that does not express TK (FIGS. 5A-5C). Furthermore, the TK.007 HSV-TK variant does not alter the vaccinia virus specificity to replicate and kill tumor cells lines while sparing normal cells.

FIGS. 5A-5C provides data on the effect of HSV-TK expression on vaccinia virus potency to kill human cancer cells, as assessed by an in vitro cytotoxicity assay. A) A549 (lung adenocarcinoma), B) MDA MB 231 (breast cancer), and C) Colo-205 (colon cancer) cancer cells were infected with vaccinia virus expressing wild-type HSV-TK (IGV-023), the TK.007 HSV-TK variant (IGV-035), or the control virus not expressing HSV-TK or J2R vaccinia TK (IGV-006), with a range of different MOIs. The infected cells were washed after 1 hour of absorption and incubated for 48 hours. Supernatants were collected and incubated with Cytotox96 Non-Radioactive Cytotoxicity Assay Buffer (Promega) for 30 minutes and absorption was read with a plate reader at 490 nm. Similar cytotoxicity is observed between the virus that expresses TK.007 HSV-TK and the virus without J2R vaccinia TK in MDA-MB-231 and Colo-205 cell lines. However, lower cytotoxicity is observed with vaccinia virus expressing the TK.007 HSV-TK variant or wildtype HSV-TK compared to vaccinia virus without J2R at higher MOIs in A549 human tumor cell lines. Lower cytotoxicity is observed in all human cancer cell lines infected with vaccinia virus expressing wild-type HSV-TK. This is a representative experiment from N=3, error bars indicate SD (n=4).

FIGS. 6A and 6B provides data on the effect of HSV-TK expression on vaccinia virus potency to kill human normal primary cells, as assessed by an in vitro cytotoxic assay. A) SAEC and B) HMEC normal primary human cells were infected with vaccinia virus expressing wild-type HSV-TK (IGV-023), the TK.007 HSV-TK variant (IGV-035), or the control virus not expressing HSV-TK or J2R vaccinia TK (IGV-006) with a range of different MOIs. The infected cells were washed after 1 hour of absorption and incubated for 48 hours. Supernatants were collected and incubated with Cytotox96 Non-Radioactive Cytotoxicity Assay Buffer (Promega) for 30 minutes and absorption was read with a plate reader at 490 nm Similar low cytotoxicity is observed between all the viruses tested in both normal primary human cell types. No significant differences were observed. Error bars indicate SD (n=4).

Example 5

Vaccinia virus expressing TK.007 HSV-TK variant demonstrates efficacy in subcutaneous patient derived xenografts (PDX) of non-small cell lung cancer and colorectal tumor models. Vaccinia virus TK.007 HSV-TK variant (IGV-038) was generated and manufactured as described in Example 1. NOD/SCID female mice were implanted subcutaneously in both flanks with either lung (LU5191) or colorectal (CR5043) PDX models. After the tumors reached a volume range between 50 and 100 mm$^3$, the animals were randomized in two groups, and the vaccinia virus expressing the TK.007 HSV-TK variant (IGV-038) or vehicle were dosed twice with $1\times10^8$ pfu (for LU5191) or $1\times10^7$ pfu (for CR5043) at day 1 and day 3 of the study. The tumor size and animal body weight were measured twice weekly for 36 days for LU5191 and 33 days for CR5043 during the course of the experiment, and the tumor volume and change in percentage of body weight were determined (FIGS. 7A-7C and FIGS. 8A-8C, respectively). In both PDX models, administration of vaccinia virus containing the TK.007 HSV-TK variant significantly reduced tumor volume compared to vehicle alone. This study demonstrates efficacy of a vaccinia virus expressing the variant TK.007 HSV-TK in two different PDX models.

Figure 7A:
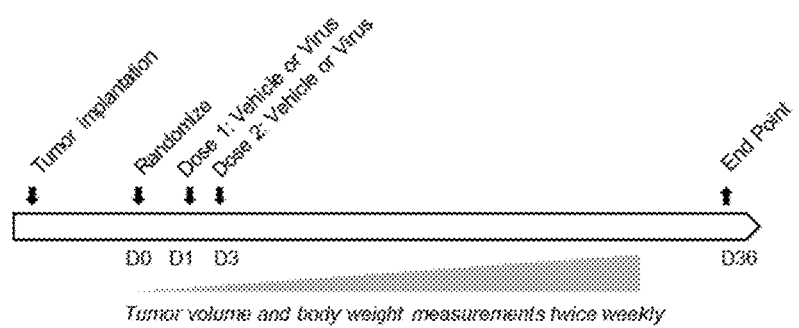
FIGS. 7A-7C depict the efficacy of an oncolytic vaccinia virus expressing variant HSV-TK in a lung patient-derived xenograft (PDX) tumor model in vivo.
Figure 7B:
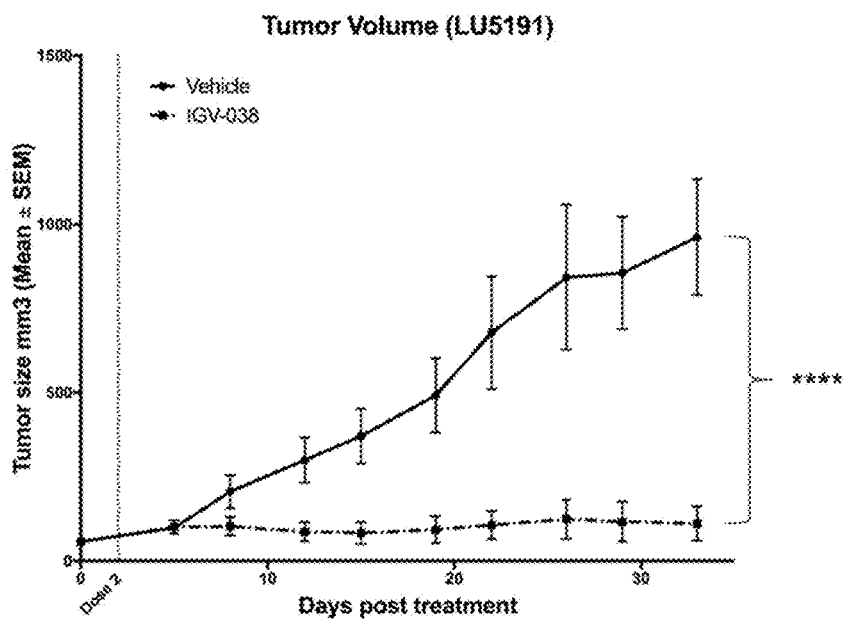
Figure 7C:
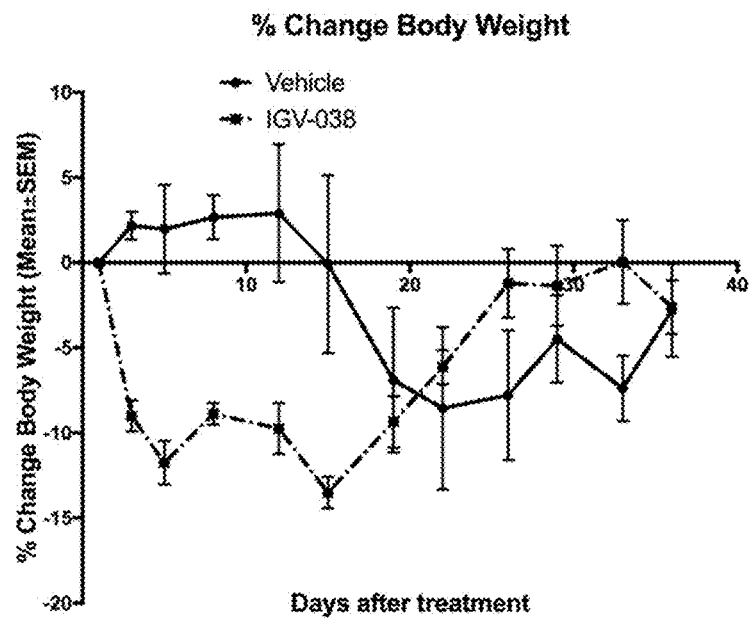

FIGS. 7A-7C provides data on efficacy of an oncolytic vaccinia virus expressing HSV-TK in a lung patient derived xenograft (PDX) tumor model in vivo. A) Study design schematic. Female NOD/SCID mice were implanted with LU5191 subcutaneously on the right and left flank of each mouse. After the tumors reached a volume range between 50 and 100 mm$^3$, the mice were randomized in two groups, and the vaccinia virus expressing the TK.007 HSV-TK variant (IGV-038) or the vehicle were dosed twice with $1\times10^8$ pfu at day 1 and day 3 of the study. B) Tumors were measured twice per week for all the animals. C) Animals were weighed twice per week, and the percentage of pre-dose body weight was calculated for both groups. Error bars indicate SEM. Data was analyzed by one-way analysis of variance (ANOVA) followed by Dunnett's multiple comparison tests. (****p<0.0001).

Figure 8A:
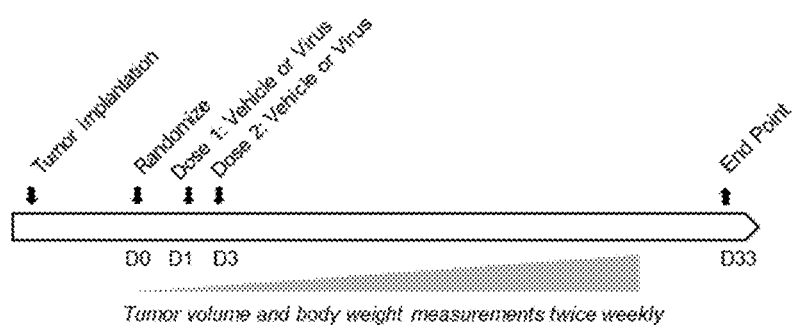
FIGS. 8A-8C depict efficacy of an oncolytic vaccinia virus expressing variant HSV-TK in a colorectal PDX tumor model in vivo.
Figure 8B:
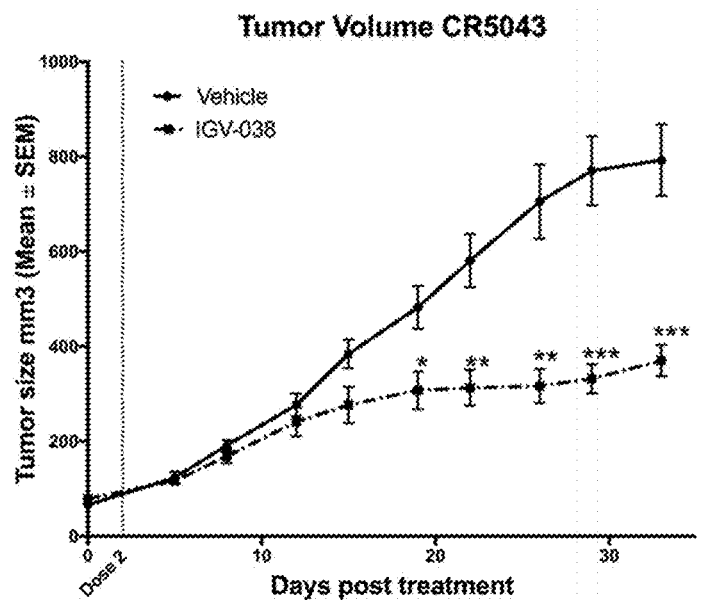
Figure 8C:
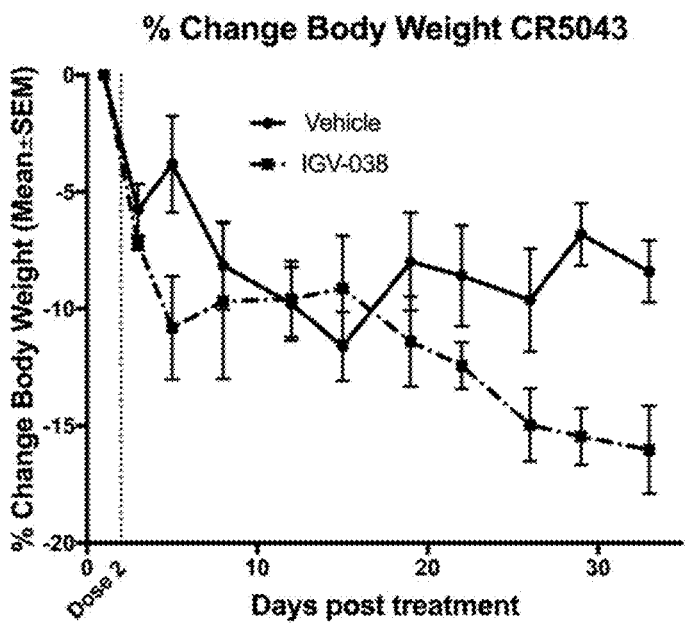

FIGS. 8A-8C provides data on efficacy of an oncolytic vaccinia virus expressing HSV-TK in a colorectal PDX tumor model in vivo. A) Study design schematic. Female NOD/SCID mice were implanted with CR5043 subcutaneously on the right and left flank of each mouse. After the tumors reached a volume range between 50 and 100 mm$^3$, the animals were randomized in two groups, and the vaccinia virus expressing the TK.007 HSV-TK variant (IGV-038) or the vehicle were dosed twice with $1\times10^7$ pfu at day 1 and day 3 of the study. B) Tumors were measured twice per week for all the animals. C) Animals were weighed twice per week, and the percentage of pre-dose body weight was calculated for both groups. Error bars indicate SEM. Data was analyzed by one-way analysis of variance (ANOVA) followed by Dunnett's multiple comparison tests. (*p<0.01; p<0.001; *p<0.0001).

Example 6

Figure 9A:
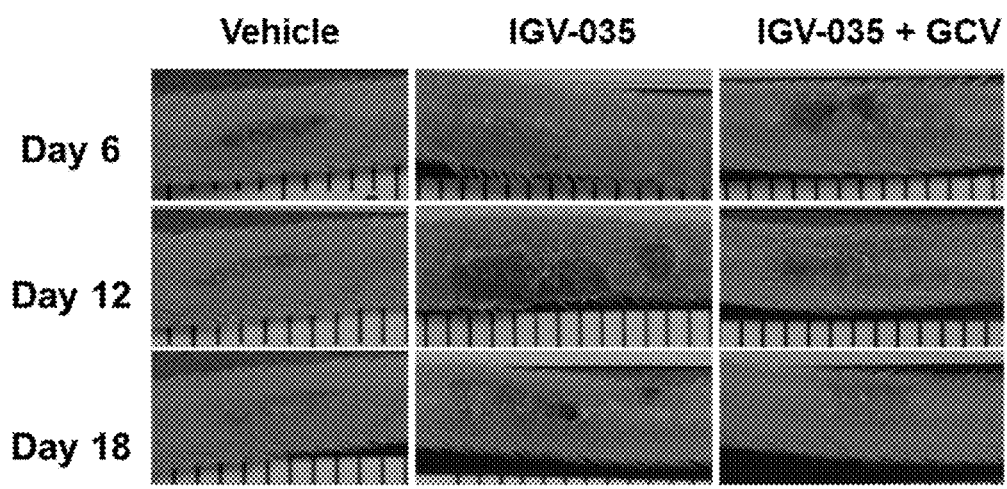
FIGS. 9A-9C depict the effect of topical ganciclovir administration on lesions in mice treated with an oncolytic recombinant vaccinia virus of the present disclosure.
Figure 9B:
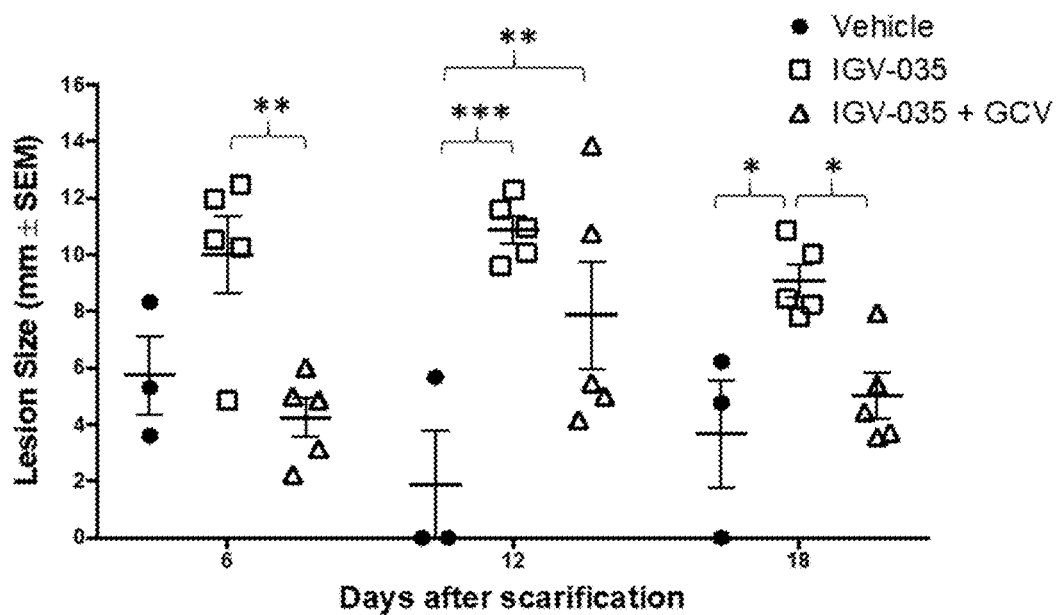
Figure 9C:
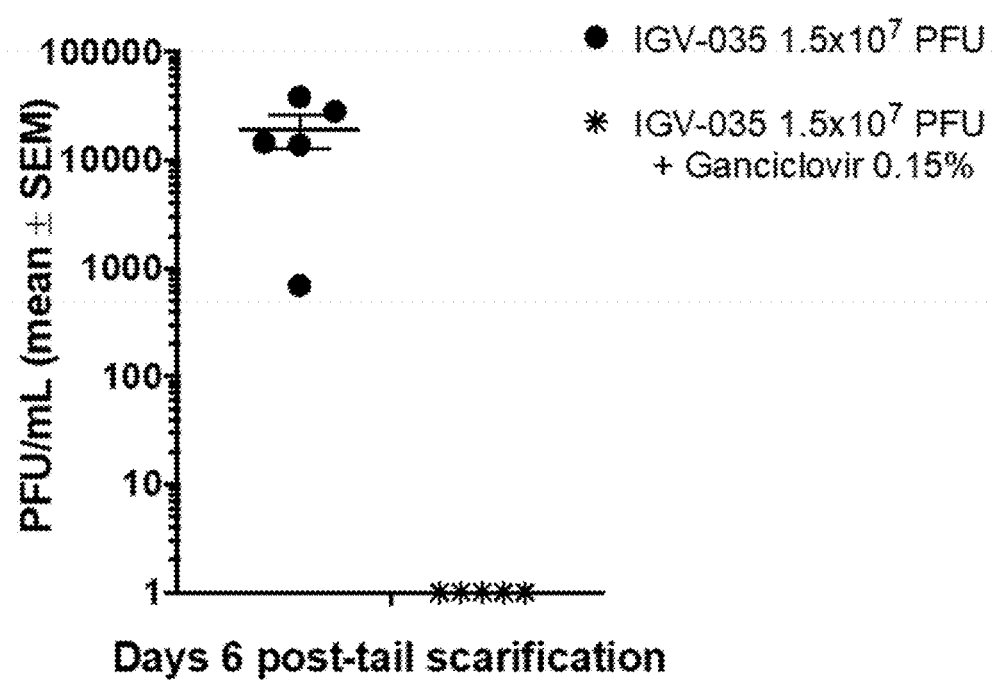

The evaluation of the sensitivity of a vaccinia virus expressing the TK.007 HSV-TK variant to topical ganciclovir administration was assessed in vivo using a tail scarification model in BALB/c mice. Vaccinia virus expressing the TK.007 HSV-TK variant was generated and manufactured as described in Example 1. Ganciclovir sensitivity was assessed by testing the ability of ganciclovir treatment to reduce the severity of virus-induced lesions in a mouse tail scarification model. Mice tail lesions were formed by scarifying $1.5\times10^7$ pfu vaccinia virus expressing the TK.007 HSV-TK variant (IGV-035) in the base of the tail. The animals were divided in three groups: one group received vehicle (no vaccinia virus); one group received 10 μL of 0.15% ganciclovir gel on the area of the lesion four times per day, every day for six days after scarification, starting 4 hours post-administration of vaccinia; and one group did not receive ganciclovir. The virus shedding was determined on day 6 post-administration in both groups. The lesion progression was observed and measured every 6 days for a total of 18 days after scarification. The lesion length was measured and photographed on day 6, day 12, and day 18. Topical lesions caused by vaccinia virus healed faster, and the lesions were significantly smaller in the group treated with ganciclovir compared to the non-treated group (FIGS. 9A and 9B). The average lesion size in the group treated with ganciclovir was comparable to the group treated with vehicle (FIGS. 9A and 9B). The lesion severity in the group treated with ganciclovir was similar to the group treated with vehicle. In the absence of ganciclovir treatment, all scarified animals exhibited increasingly severe lesions over time (FIG. 9A). Finally, topical ganciclovir treatment reduced virus shedding from the tail scarification site on day 6 post-administration (FIG. 9C). This study demonstrates that the topical treatment with ganciclovir has an effect on lesion development, lesion size, lesion severity, and virus shedding when it is applied early following administration of oncolytic vaccinia virus. In addition, the lesions were healed and cleared faster in animals treated with ganciclovir.

FIGS. 9A-9C provide data on variant HSV-TK-expressing vaccinia virus sensitivity to topical ganciclovir administration and reduction of lesion development. Vaccinia virus expressing the TK.007 HSV-TK variant (IGV-035) was administered via tail scarification in the absence or presence of topical ganciclovir (GCV) treatment. A) representative images of tail lesions, B) quantification of lesion size at days 6, 12, and 18 post-virus scarification in the presence or absence of topical 0.15% ganciclovir gel treatment, and C) quantification of infectious virus shedding from the tail scarification site at day 6 post-virus scarification in the presence or absence of topical 0.15% ganciclovir gel treatment. Error bars indicate SEM. Data was analyzed by two-way analysis of variance (ANOVA) followed by Tukey's multiple comparisons test. (*p<0.05; p<0.01; *p<0.001).

Example 7

Figure 10A:
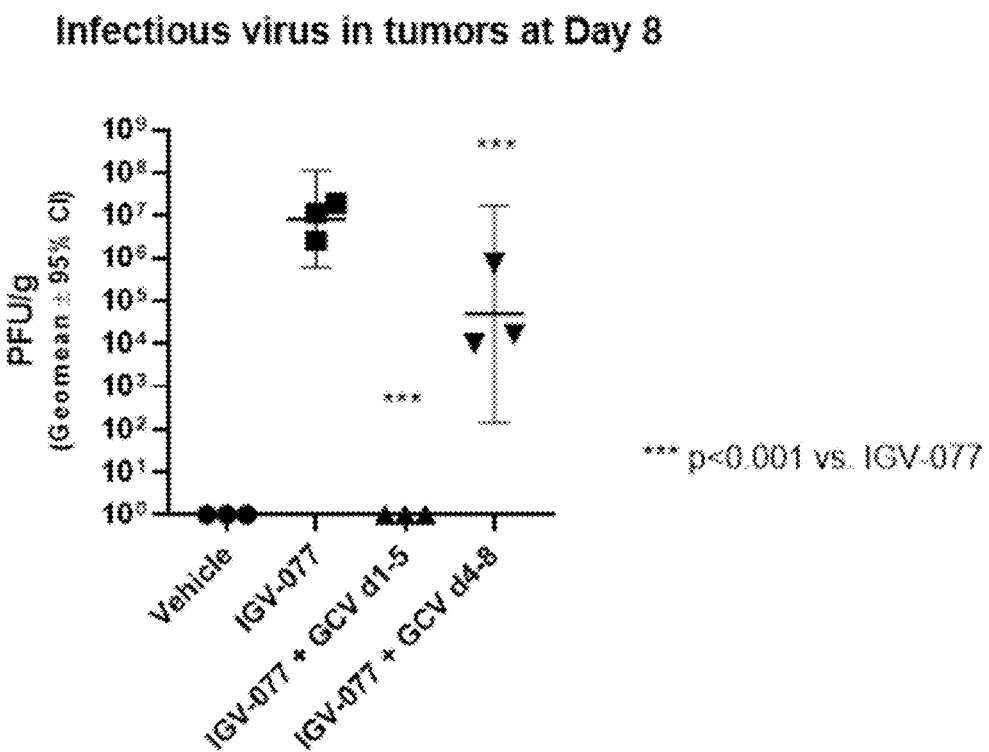
FIGS. 10A and 10B depict the effect of systemic ganciclovir administration on replication of an oncolytic recombinant vaccinia virus of the present disclosure in vivo.
Figure 10B:
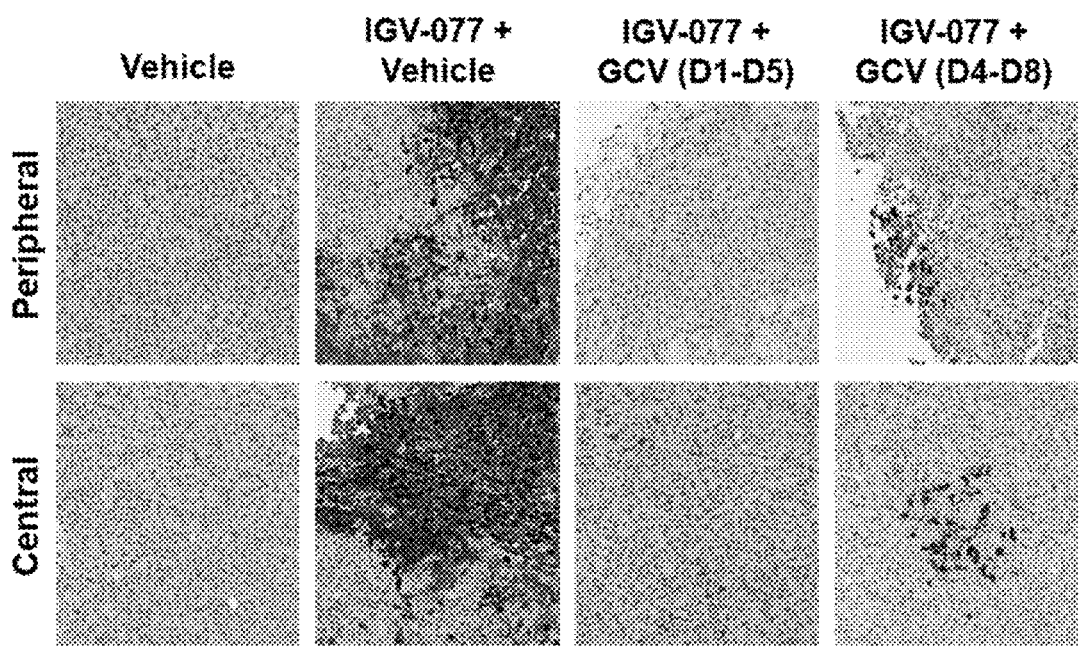

The impact of ganciclovir on a systemically delivered vaccinia virus expressing the TK.007 HSV-TK variant was assessed in vivo by evaluating virus replication in the tumor in a subcutaneous non-small cell lung cancer patient derived xenograft (PDX) model. Vaccinia virus expressing the TK.007 HSV-TK variant was generated and manufactured as described in Example 1. Mice were implanted subcutaneously on the right flank with non-small cell lung cancer (LU5191) PDX cells. Once tumor volumes reached a volume range between 100 and 200 mm$^3$ (approximately 3 weeks post-implantation), mice were randomized into 4 treatment groups. Mice in group 1 were administered vehicle, mice in groups 2, 3 and 4 were administered intravenous vaccinia virus expressing the TK.007 HSV-TK variant (IGV-077) twice, on day 1 and 3 of the study with 1×10$^7$ pfu each treatment day. Ganciclovir 50 mg/kg was administered intraperitoneally on days 1-5 of the study to group 3 and on days 4-8 of the study to group 4. Group 2 received vehicle instead of ganciclovir. Animals on each group were sacrificed on day 8 of the study, tumors were harvested, and virus replication and virus-mediated transgene expression throughout the tumor were determined by plaque assay and immunohistochemistry. Virus replication was significantly reduced in tumors when ganciclovir was administered on days 4-8 of the study, and viral replication was completely inhibited when ganciclovir was administered on days 1-5 of the study (FIG. 10A). In addition, no replicating virus was detected for any groups in normal organs, including ovaries, spleen, lungs and liver. Low levels of virus-mediated GFP expression were detected at day 8 by immunohistochemistry when ganciclovir was administered on days 4-8 of the study, and no virus-mediated GFP expression was detected when ganciclovir was administered on days 1-5 of the study (FIG. 10B). This study illustrates that incorporation of the TK.007 HSV-TK variant in vaccinia virus makes this virus susceptible to replication inhibition and clearance by systemic treatment with ganciclovir. Furthermore, the timing of ganciclovir treatment can be modified to reduce, but not completely inhibit viral replication as a method of modifying the activity of the oncolytic virus.

FIGS. 10A and 10B provide data on systemic inhibition of variant HSV-TK-expressing vaccinia virus by systemic ganciclovir administration. Vaccinia virus expressing the TK.007 HSV-TK variant (IGV-077) was intravenously administered in the absence or presence of systemic ganciclovir (GCV) treatment using two different ganciclovir treatment timelines. A) quantification of viral replication (infectious virus) in tumors on day 8 post-administration. Error bars indicate 95% CI. ***p<0.001 by ANOVA. B) representative images of vaccinia virus-mediated GFP transgene expression in tumors.

Example 8

Figure 11A:
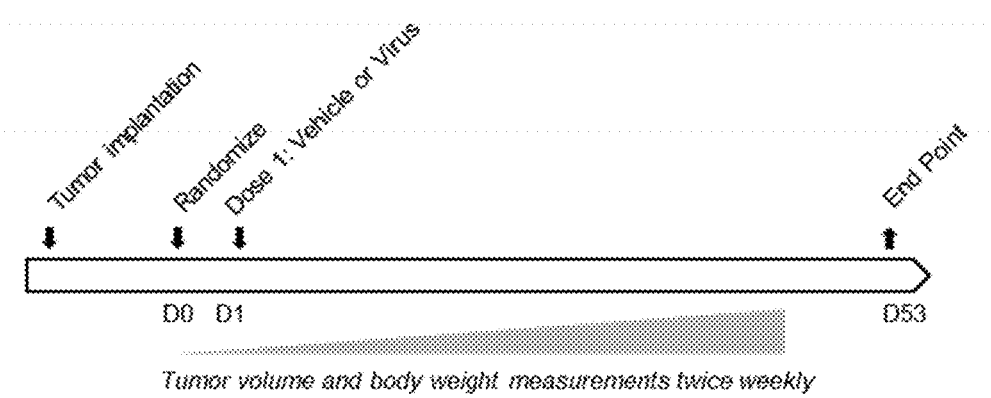
FIGS. 11A and 11B depict the efficacy of an oncolytic vaccinia virus expressing variant HSV-TK in a lung patient-derived xenograft (PDX) tumor model in vivo.
Figure 11B:
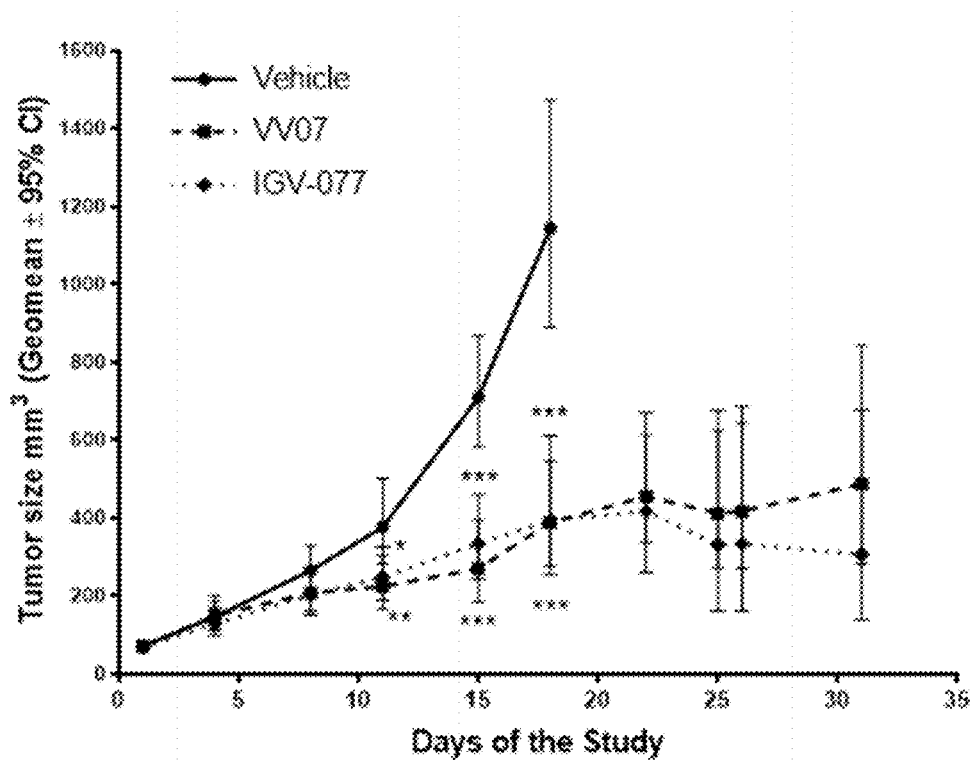
Figure 12A:
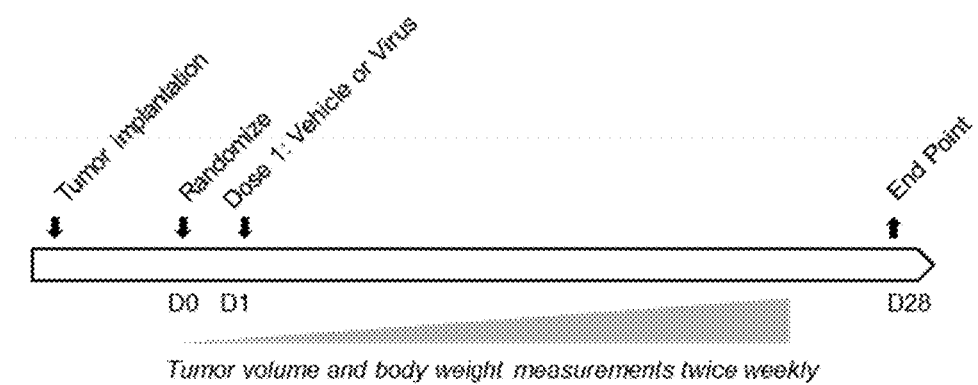
FIGS. 12A and 12B depict the efficacy of an oncolytic vaccinia virus expressing variant HSV-TK in a colorectal cancer xenograft tumor model in vivo.
Figure 12B:
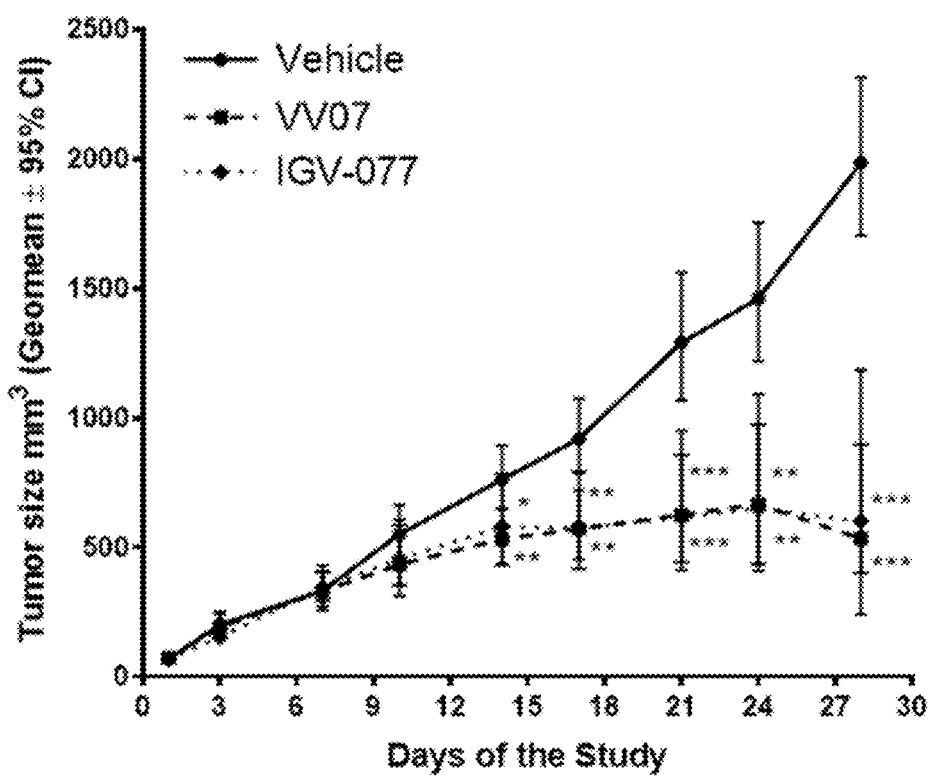

The impact of the substitution variants was assessed in vivo by evaluating tumor growth inhibition of human PDX and human tumor cell line xenograft implants in nude mice. Copenhagen vaccinia viruses lacking vaccinia virus TK and containing either Luciferase-2A-GFP (VV07) or the TK.007 HSV-TK variant (IGV-077) were generated and manufactured as described in Example 1. In the first study, NOD/SCID female mice were implanted subcutaneously in the rear flank with lung (LU5191) PDX tissue. After the tumors reached a volume range between 50 and 85 mm$^3$, the animals were randomized in three groups. Mice in group 1 were administered vehicle, and mice in groups 2-3 were intravenously administered 3×10$^6$ PFU of recombinant Copenhagen vaccinia viruses lacking vaccinia virus TK and containing either Luciferase-2A-GFP (VV07) or the TK.007 HSV-TK variant (IGV-077) on Day 1 (FIG. 11A). Tumor volumes were measured twice per week until endpoint (tumor volume exceeding 2000 mm$^3$) Mice administered with IGV-077 and VV07 showed statistically significant increased tumor growth inhibition compared to vehicle (FIG. 11B). In the second study, mice were implanted subcutaneously on the right front flank with human HCT-116 colorectal cells. Once tumors reach a size range of 50-85 mm$^3$, mice were randomized into three treatment groups. Mice in group 1 were administered vehicle, and mice in groups 2-3 were intravenously administered 3×10$^6$ PFU of recombinant Copenhagen vaccinia viruses lacking vaccinia virus TK and containing either Luciferase-2A-GFP (VV07) or the TK.007 HSV-TK variant (IGV-077) on Day 1 (FIG. 12A). Tumor volumes were measured twice per week until endpoint (tumor volume exceeds 2000 mm$^3$). Mice administered with IGV-077 and VV07 showed significant increased tumor growth inhibition compared to vehicle (FIG. 12B). These studies illustrate that incorporation of variant HSV-TK does not adversely affect the efficacy of the oncolytic vaccinia virus in tumor growth inhibition and thus survival in vivo.

FIGS. 11A and 11B provides data on efficacy of oncolytic vaccinia virus expressing HSV-TK in a lung PDX tumor model in vivo. A) Study design schematic. Female NOD/SCID mice were implanted subcutaneously with human LU5191 PDX tissue on the rear flank of each mouse. After the tumors reached a volume range between 56.5 and 84.3 mm$^3$, the mice were randomized in three groups, and the vaccinia virus expressing Luciferase-2A-GFP (VV007), the vaccinia virus expressing the TK.007 HSV-TK variant (IGV-077), or the vehicle were dosed once with 3×10$^6$ pfu on day 1 of the study. B) Tumors were measured twice per week for all the animals.

FIGS. 12A and 12B provides data on efficacy of oncolytic vaccinia virus expressing HSV-TK in a colorectal cancer xenograft tumor model in vivo. A) Study design schematic. Mice were implanted with HCT-116 subcutaneously on the right front flank of each mouse. After the tumors reached a volume range between 56.5 and 84.3 mm$^3$, the mice were randomized in three groups, and the vaccinia virus expressing Luciferase-2A-GFP (VV007), the vaccinia virus expressing the TK.007 HSV-TK variant (IGV-077), or the vehicle were dosed once with 3×10$^6$ pfu on day 1 of the study. B) Tumors were measured twice per week for all the animals.

Example 9

Figure 13A:
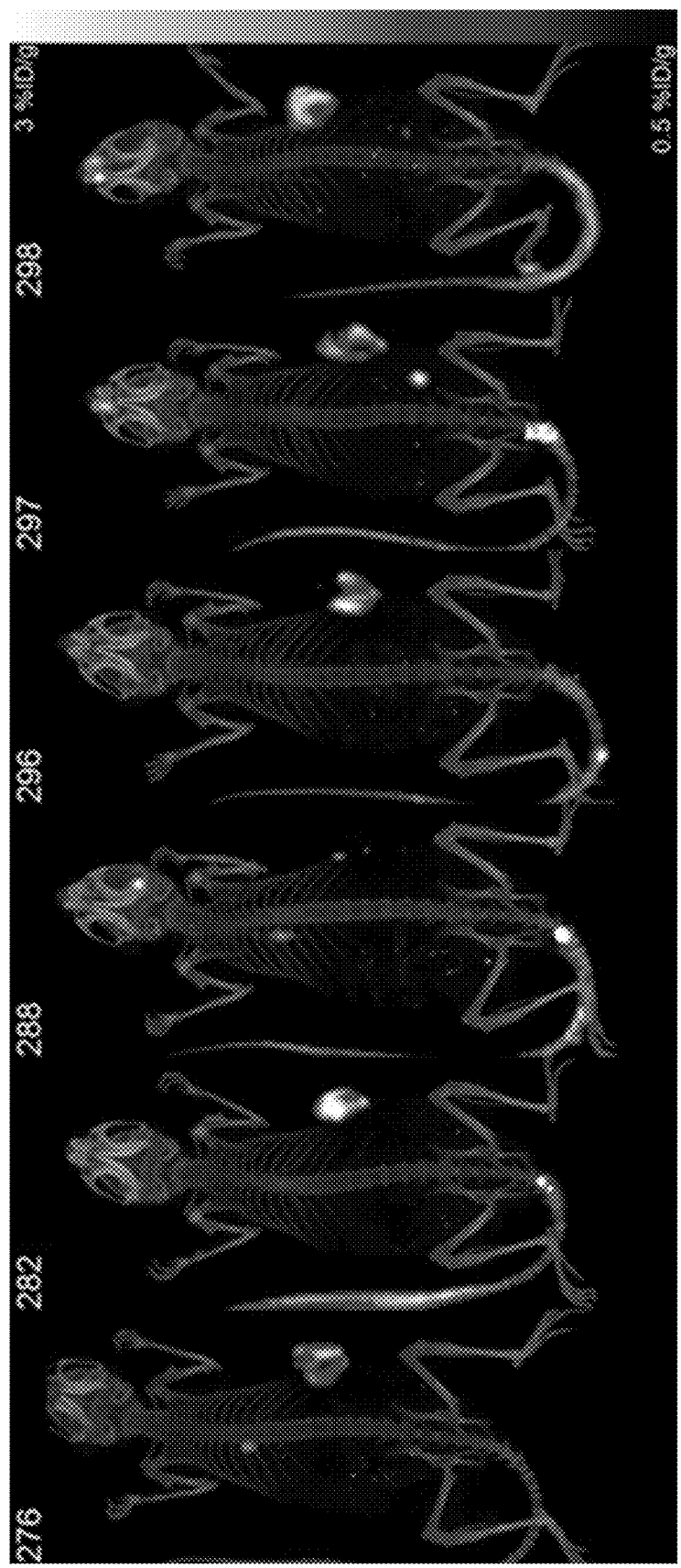
FIGS. 13A-13E depict the use of radiolabeled TK substrate to detect distribution in real time and replication of an oncolytic vaccinia virus expressing variant HSV-TK in a colorectal cancer xenograft tumor model in vivo.
Figure 13B:
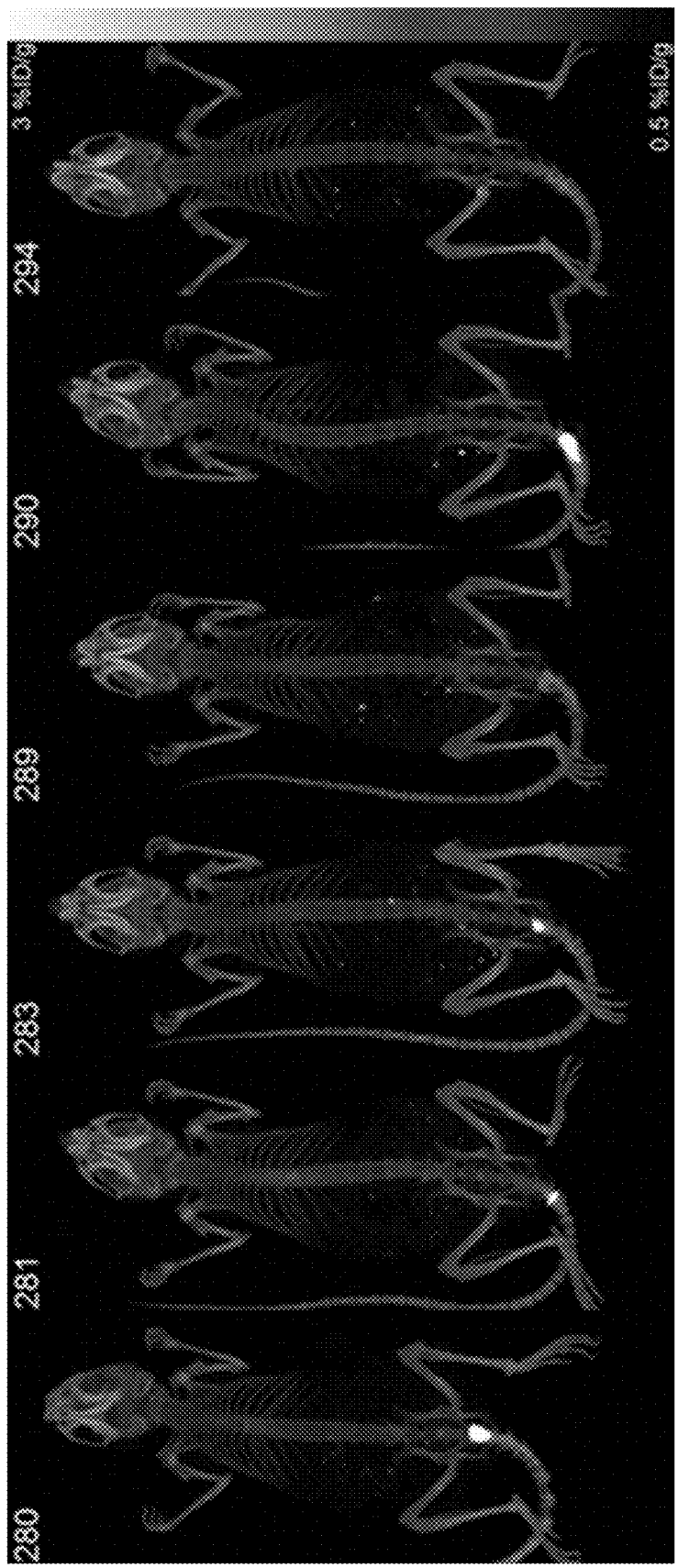
Figure 13C:
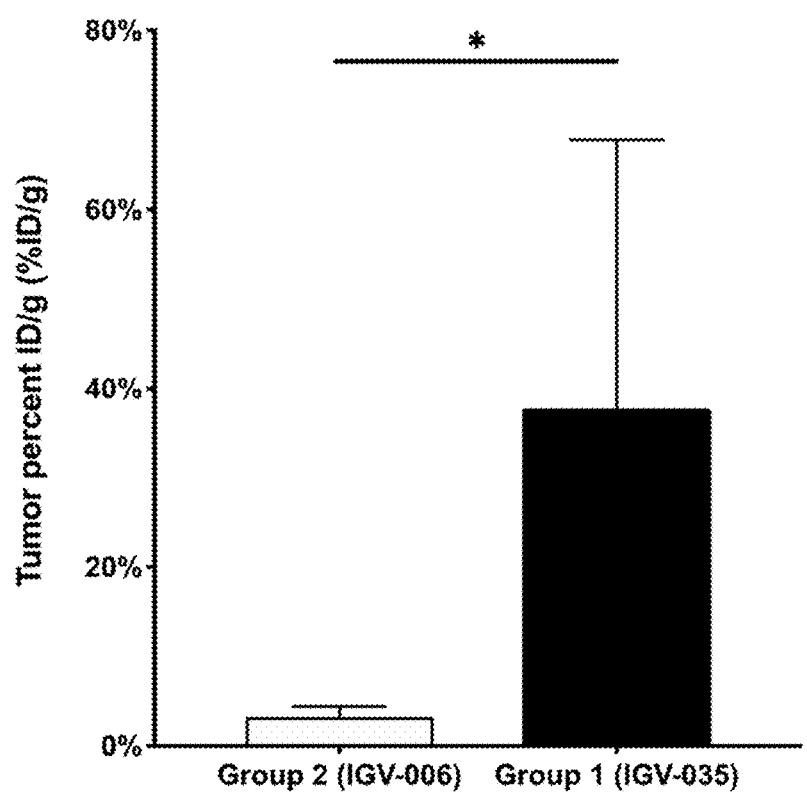
Figure 13D:
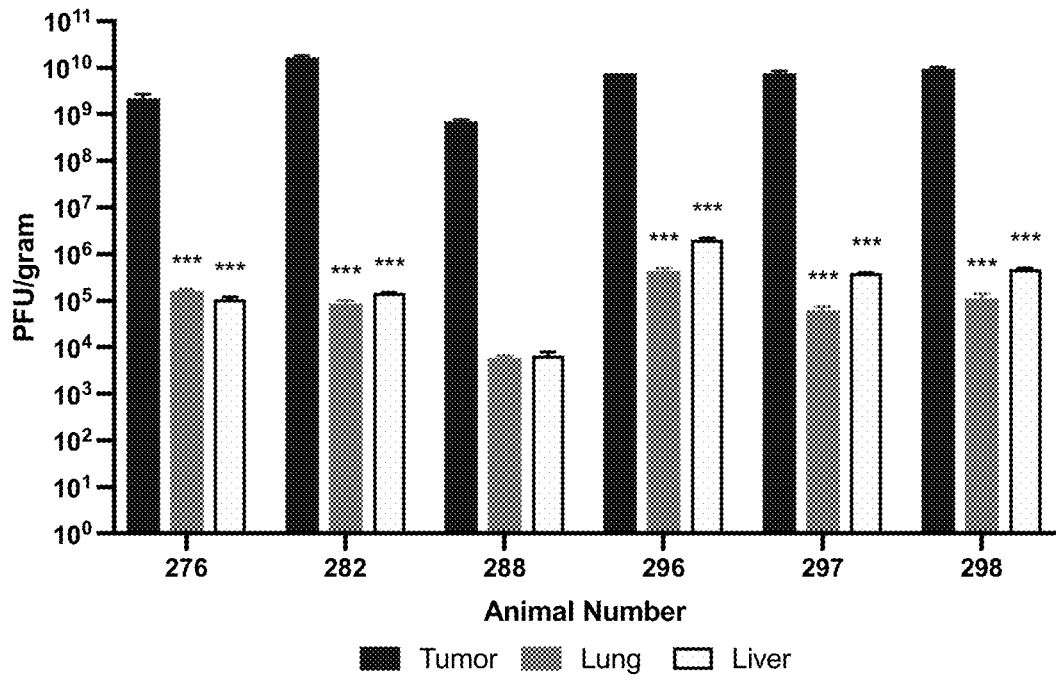
Figure 13E:
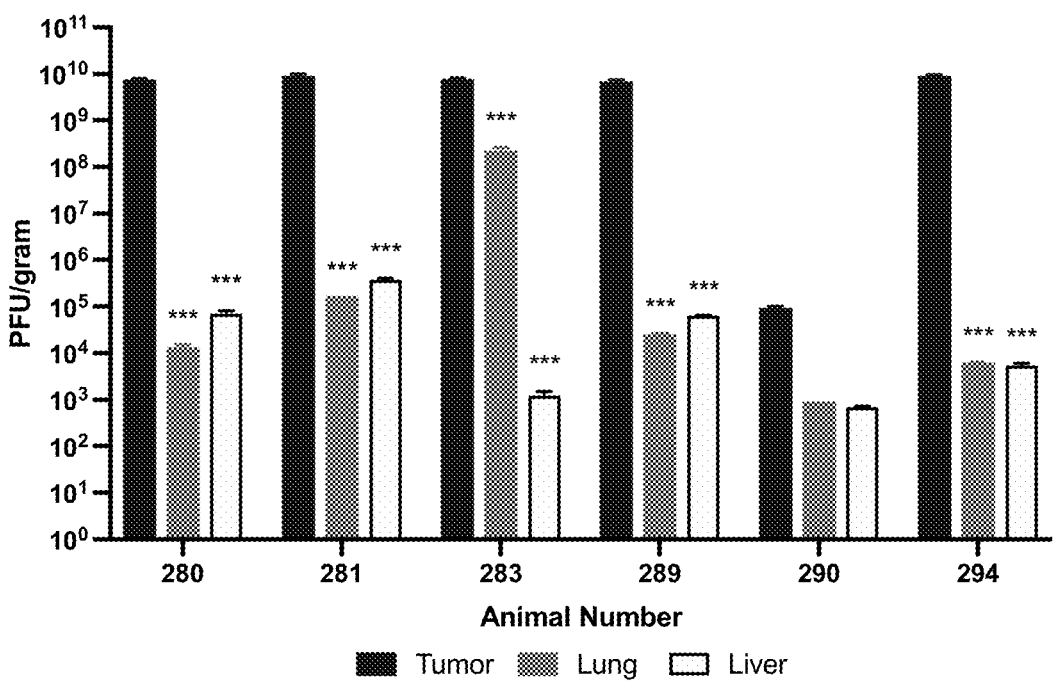

The ability to detect images in real time of the distribution and replication of an oncolytic vaccinia in vivo was assessed through use of radiolabeled ganciclovir and positron emission tomography-computed tomography (PET-CT). Copenhagen vaccinia viruses lacking vaccinia virus TK and containing either Luciferase-2A-GFP (IGV-006) or the TK.007 HSV-TK variant (IGV-035) were generated and manufactured as described in Example 1. Mice were implanted subcutaneously on the right front flank with HCT-116 human colorectal cells. Once tumors reached a size range of 90-220 mm$^3$, mice were randomized into two treatment groups. Mice were intravenously administered 3×10$^7$ PFU of recombinant Copenhagen Vaccinia viruses lacking vaccinia virus TK and containing either the TK.007 HSV-TK variant (IGV-035; Group 1) or Luciferase-2A-GFP (IGV-006; Group 2) on Day 1. On Day 5 and Day 8, mice were administered radiolabeled $^{18}$F-fluoro-3-[hydroxymethyl]

butyl)guanine ($^{18}$F-FHBG) and imaged using PET-CT. Mice administered IGV-035 showed increased tumor-specific signal on Day 8 (FIG. 13A). In comparison, mice administered IGV-006 showed no tumor-specific signal, as expected due to the lack of HSV-TK in the IGV-006 oncolytic vaccinia virus administered to Group 2 (FIG. 13B). $^{18}$F-FHBG signal was quantified and reported as the percentage of injected $^{18}$F-FHGB activity detected in the tumor normalized to the weight (in grams) of tissue. Mice administered IGV-035 had significantly higher $^{18}$F-FHBG signal compared to mice administered IGV-006 (FIG. 13C), demonstrating that expression of HSV-TK could be used to image oncolytic virus replication in vivo. Viral titers per weight of tissue were multiple orders of magnitude higher in tumors compared to liver and lung tissue for both IGV-035 (FIG. 13D) and IGV-006 (FIG. 13E). The high viral titers in tumor compared to other tissues further demonstrate that the signal observed from IGV-035 is specifically localized to tumor tissue. The average viral titers per weight of tumor tissue were similar for IGV-035 and IGV-006, which shows that the presence of signal in tumor tissue for IGV-035 but not IGV-006 is due to the presence of the variant HSV-TK, and not a difference in viral titer. These studies illustrate that incorporation of a variant HSV-TK can facilitate imaging detection, distribution and replication of oncolytic vaccinia virus in vivo.

FIGS. 13A-13E provides data on the use of radiolabeled substrate to detect images in real time of distribution and replication of an oncolytic vaccinia virus expressing a variant HSV-TK in a human colorectal cancer xenograft tumor model in vivo. A) Full body PET-CT imaging of mice intravenously administered with 3×10$^7$ pfu oncolytic vaccinia virus expressing variant HSV-TK (IGV-035) and radiolabeled substrate. Mice were implanted with human HCT-116 colorectal cells subcutaneously on the right front flank of each mouse. B) Full body PET-CT imaging of mice intravenously administered with 3×10$^7$ pfu oncolytic vaccinia virus containing Luciferase-2A-GFP (IGV-006) and radiolabeled substrate ($^{18}$F-FHBG). Mice were implanted with human HCT-116 colorectal cells subcutaneously on the right front flank of each mouse. C) Quantification of $^{18}$F-FHBG activity in tumors, expressed as percentage of $^{18}$F-FHGB activity of the injected dose per gram of tissue weight. D) Quantification of viral titers in tumor and non-tumor tissues of mice administered 3×10$^7$ pfu oncolytic vaccinia virus expressing variant HSV-TK (IGV-035). E) Quantification of viral titers in tumor and non-tumor tissues of mice administered 3×10$^7$ pfu oncolytic vaccinia virus containing Luciferase-2A-GFP (IGV-006). For A) and B), non-specific signal observed in gut has been removed from all images. Error bars indicate SEM for C), D) and E). Data was analyzed by student's T-test for C) or 2-way ANOVA for D) and E). Asterisks indicate significance compared against IGV-006 for c) or significance compared with tumor tissue titers for D) and E) (*p<0.05, p<0.01, p<0.001).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A replication-competent, recombinant oncolytic vaccinia virus comprising: a) a nucleotide sequence encoding a variant herpes simplex virus (HSV) TK polypeptide capable of catalyzing phosphorylation of deoxyguanosine; and b) a modification that results in a lack of endogenous thymidine kinase expression or function, wherein the variant HSV TK polypeptide comprises the amino acid sequence of SEQ ID NO:2, 3, or 4.

2. The replication-competent, recombinant oncolytic vaccinia virus of claim 1, wherein the variant HSV TK polypeptide comprises the amino acid sequence of SEQ ID NO:2.

3. The replication-competent, recombinant oncolytic vaccinia virus of claim 1, wherein the variant HSV TK polypeptide comprises the amino acid sequence of SEQ ID NO:3.

4. The replication-competent, recombinant oncolytic vaccinia virus of claim 1, wherein the variant HSV TK polypeptide comprises the amino acid sequence of SEQ ID NO: 4.

5. The replication-competent, recombinant oncolytic vaccinia virus of claim 1, wherein the vaccinia virus is a Copenhagen strain vaccinia virus.

6. The replication-competent, recombinant oncolytic vaccinia virus of claim 1 wherein the vaccinia virus is a WR strain vaccinia virus.

7. The replication-competent, recombinant oncolytic vaccinia virus of claim 1, wherein the vaccinia virus comprises an A34R gene that encodes an A34 polypeptide comprising a K151E substitution.

8. A composition comprising:
a) the vaccinia virus of claim 1; and
b) a pharmaceutically acceptable excipient.

9. A method of inducing oncolysis in an individual having a tumor, the method comprising administering to the individual an effective amount of the composition of claim 8.

10. The method of claim 9, further comprising administering to the individual a second cancer therapy.

11. The method of claim 10, wherein the second cancer therapy comprises an anti-PD1 agent or an anti-PD-L1 agent.

12. The method of claim 9, further comprising administering to the individual an amount of ganciclovir that, in combination with the vaccinia virus, is effective to reduce an adverse side effect of the vaccinia virus.

13. The method of claim 9, wherein the variant (HSV) HSV TK polypeptide comprises the amino acid sequence of SEQ ID NO: 4.

14. The method of claim 13, wherein the vaccinia virus is a Copenhagen strain vaccinia virus and comprises an A34R gene comprising a K151E substitution.

15. The replication-competent, recombinant oncolytic vaccinia virus of claim 1, wherein the nucleotide sequence encoding the variant HSV TK polypeptide is set forth in SEQ ID NO: 11, 12 or 13.

* * * * *

SEQUENCE LISTING

<160> NUMBER OF SEQ ID NOS: 13

<210> SEQ ID NO 1
<211> LENGTH: 376
<212> TYPE: PRT
<213> ORGANISM: human herpesvirus 1

<400> SEQUENCE: 1

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140
```

-continued

```
Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Ile Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375
```

<210> SEQ ID NO 2
<211> LENGTH: 376
<212> TYPE: PRT
<213> ORGANISM: Artificial Sequence
<220> FEATURE:
<223> OTHER INFORMATION: Synthetic peptide sequence

<400> SEQUENCE: 2

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125
```

```
Gly Met Pro Tyr Ala Val Thr Asp Ala Val Leu Ala Pro His Ile Gly
        130                 135                 140

Gly Glu Ala Gly Ser Ser His Val Pro Pro Ala Leu Thr Ile Leu
145                 150                 155                 160

Ala Asp Arg His Pro Ile Ala Tyr Phe Leu Cys Tyr Pro Ala Ala Arg
                    165                 170                 175

Tyr Leu Met Gly Ser Met Thr Pro Gln Ala Val Leu Ala Phe Val Ala
                    180                 185                 190

Leu Ile Pro Pro Thr Leu Pro Gly Thr Asn Ile Val Leu Gly Ala Leu
                    195                 200                 205

Pro Glu Asp Arg His Ile Asp Arg Leu Ala Lys Arg Gln Arg Pro Gly
210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Ser Trp Arg
                    245                 250                 255

Glu Asp Trp Gly Gln Leu Ser Gly Thr Ala Val Pro Gln Gly Ala
                    260                 265                 270

Glu Pro Gln Ser Asn Ala Gly Pro Arg Pro His Ile Gly Asp Thr Leu
                    275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                    325                 330                 335

Arg Asp Ala Leu Leu Gln Leu Thr Ser Gly Met Ile Gln Thr His Val
                    340                 345                 350

Thr Thr Pro Gly Ser Ile Pro Thr Ile Cys Asp Leu Ala Arg Thr Phe
                    355                 360                 365

Ala Arg Glu Met Gly Glu Ala Asn
            370                 375

<210> SEQ ID NO 3
<211> LENGTH: 376
<212> TYPE: PRT
<213> ORGANISM: Artificial Sequence
<220> FEATURE:
<223> OTHER INFORMATION: Synthetic peptide sequence

<400> SEQUENCE: 3

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Pro Glu Gln Lys Met Pro Thr
            35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
                100                 105                 110
```

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Ala Leu Thr Ile Phe
145                 150                 155                 160

Leu Asp Arg His Pro Ile Ala Phe Met Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Ile Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 4
<211> LENGTH: 376
<212> TYPE: PRT
<213> ORGANISM: Artificial Sequence
<220> FEATURE:
<223> OTHER INFORMATION: Synthetic peptide sequence

<400> SEQUENCE: 4

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

```
Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala His Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
                275                 280                 285

Phe Thr Leu Phe Arg Ala Pro Glu Leu Leu Ala Pro Asn Gly Asp Leu
            290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Ile Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 5
<211> LENGTH: 25
<212> TYPE: PRT
<213> ORGANISM: human herpesvirus 1

<400> SEQUENCE: 5

His Ala Pro Pro Ala Leu Thr Leu Ile Phe Asp Arg His Pro Ile
1               5                   10                  15

Ala Ala Leu Leu Cys Tyr Pro Ala Ala
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthetic peptide sequence

<400> SEQUENCE: 6

His Val Pro Pro Pro Ala Leu Thr Ile Leu Ala Asp Arg His Pro Ile
```

```
                1               5                   10                  15

Ala Tyr Phe Leu Cys Tyr Pro Ala Ala
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic peptide sequence

<400> SEQUENCE: 7

His Ala Pro Pro Pro Ala Leu Thr Ile Phe Leu Asp Arg His Pro Ile
1               5                   10                  15

Ala Phe Met Leu Cys Tyr Pro Ala Ala
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic peptide sequence

<400> SEQUENCE: 8

His Ala Pro Pro Pro Ala Leu Thr Leu Ile Phe Asp Arg His Pro Ile
1               5                   10                  15

Ala His Leu Leu Cys Tyr Pro Ala Ala
            20                  25

<210> SEQ ID NO 9
<211> LENGTH: 40
<212> TYPE: DNA
<213> ORGANISM: Artificial Sequence
<220> FEATURE:
<223> OTHER INFORMATION: Synthetic nucleotide sequence

<400> SEQUENCE: 9
aaaaattgaa attttatttt ttttttttgg aatataaata                          40

<210> SEQ ID NO 10
<211> LENGTH: 1128
<212> TYPE: DNA
<213> ORGANISM: human herpesvirus 1

<400> SEQUENCE: 10
atggcctcat atcctggtca tcaacacgct agtgccttcg accaggcggc gagatctcga    60
ggacattcga atagcgaaca agcattacgt ccacgaagac aacaggaggc gacagaggtc   120
cgacctgaac agaaaatgcc tacacttttg cgagtctaca tagatggtcc ccacggaatg   180
ggtaaaacta ccactaccca gttgttagtc gccttaggtt ctcgagacga tattgtctat   240
gtgcccgagc ccatgactta ctggcgagtc ctaggtgcat cggaaacgat agcgaacatc   300
tatacgacac agcatcgttt ggaccaggga gagatctcgg ccggtgacgc agcagtcgta   360
atgacaagtg ctcaaattac gatgggtatg ccttatgcgg taactgacgc agtcttggct   420
ccgcatatcg gtggagaggc cggatcgtca cacgctcccc ctccagcgtt aactctaatt   480
ttcgaccgac acccaattgc tgcgctttta tgttaccccg cggcaagata tttaatggga   540
tcaatgaccc cgcaagctgt gttagctttt gtggcattga ttcgccaac cttacctgga   600 acgaatatag tccttggtgc attaccagag gatagacata ttgacagact tgctaagcga   660
```

| | |
|---|---|
| cagcgaccgg gagagagatt ggacttagca atgttggcgg ccataagacg agtctacgga | 720 |
| cttttggcta atacggttag atatttgcaa ggaggaggaa gttggcgaga ggattggggt | 780 |
| cagttgtctg gtactgctgt gcctccgcag ggagctgagc ctcagtctaa cgctggacca | 840 |
| cgacctcaca tcggagatac gttatttacc ctattccgtg cgccggaatt attagcaccc | 900 |
| aacggtgatc tatacaacgt cttttgcgtgg gccttggacg tacttgcaaa gcgtctacgt | 960 |
| cctatgcatg tcttcatcct agactacgac cagtcgcccg cgggatgtcg agacgccttg | 1020 |
| ctacagttga cctcgggaat gattcagaca cacgtcacca ccccgggatc catacccact | 1080 |
| atttgtgact tagcaagaac atttgcccga gaaatgggtg aagctaac | 1128 |

<210> SEQ ID NO 11
<211> LENGTH: 1128
<212> TYPE: DNA
<213> ORGANISM: Artificial Sequence
<220> FEATURE:
<223> OTHER INFORMATION: Synthetic nucleotide sequence

<400> SEQUENCE: 11

| | |
|---|---|
| atggcctcat atcctggtca tcaacacgct agtgccttcg accaggcggc gagatctcga | 60 |
| ggacattcga atagacgaac agcattacgt ccacgaagac aacaggaggc gacagaggtc | 120 |
| cgacctgaac agaaaatgcc tacacttttg cgagtctaca tagatggtcc ccacggaatg | 180 |
| ggtaaaacta ccactaccca gttgttagtc gccttaggtt ctcgagacga tattgtctat | 240 |
| gtgcccgagc ccatgactta ctggcgagtc ctaggtgcat cggaaacgat agcgaacatc | 300 |
| tatacgacac agcatcgttt ggaccaggga gagatctcgg ccggtgacgc agcagtcgta | 360 |
| atgacaagtg ctcaaattac gatgggtatg ccttatgcgg taactgacgc agtcttggct | 420 |
| ccgcatatcg gtggagaggc cggatcgtca cacgtgcccc ctccagcgtt aactatttta | 480 |
| gcggaccgac acccaattgc ttacttctta tgttaccccg cggcaagata tttaatggga | 540 |
| tcaatgaccc cgcaagctgt gttagctttt gtggcattga ttccgccaac cttacctgga | 600 |
| acgaatatag tccttggtgc attaccagag gatagacata ttgacagact tgctaagcga | 660 |
| cagcgaccgg gagagagatt ggacttagca atgttggcgg ccataagacg agtctacgga | 720 |
| cttttggcta atacggttag atatttgcaa ggaggaggaa gttggcgaga ggattggggt | 780 |
| cagttgtctg gtactgctgt gcctccgcag ggagctgagc ctcagtctaa cgctggacca | 840 |
| cgacctcaca tcggagatac gttatttacc ctattccgtg cgccggaatt attagcaccc | 900 |
| aacggtgatc tatacaacgt cttttgcgtgg gccttggacg tacttgcaaa gcgtctacgt | 960 |
| cctatgcatg tcttcatcct agactacgac cagtcgcccg cgggatgtcg agacgccttg | 1020 |
| ctacagttga cctcgggaat gattcagaca cacgtcacca ccccgggatc catacccact | 1080 |
| atttgtgact tagcaagaac atttgcccga gaaatgggtg aagctaac | 1128 |

<210> SEQ ID NO 12
<211> LENGTH: 1128
<212> TYPE: DNA
<213> ORGANISM: Artificial Sequence
<220> FEATURE:
<223> OTHER INFORMATION: Synthetic nucleotide sequence

<400> SEQUENCE: 12

| | |
|---|---|
| atggcctcat atcctggtca tcaacacgct agtgccttcg accaggcggc gagatctcga | 60 |
| ggacattcga atagacgaac agcattacgt ccacgaagac aacaggaggc gacagaggtc | 120 |
| cgacctgaac agaaaatgcc tacacttttg cgagtctaca tagatggtcc ccacggaatg | 180 |

```
ggtaaaacta ccactaccca gttgttagtc gccttaggtt ctcgagacga tattgtctat        240
gtgcccgagc ccatgactta ctggcgagtc ctaggtgcat cggaaacgat agcgaacatc        300
tatacgacac agcatcgttt ggaccaggga gagatctcgg ccggtgacgc agcagtcgta        360
atgacaagtg ctcaaattac gatgggtatg ccttatgcgg taactgacgc agtcttggct        420
ccgcatatcg gtggagaggc cggatcgtca cacgctcccc ctccagcgtt aactattttc        480
ttagaccgac acccaattgc tttcatgtta tgttaccccg cggcaagata tttaatggga        540
tcaatgaccc cgcaagctgt gttagctttt gtggcattga ttccgccaac cttacctgga        600
acgaatatag tccttggtgc attaccagag gatagacata ttgacagact tgctaagcga        660
cagcgaccgg gagagagatt ggacttagca atgttggcgg ccataagacg agtctacgga        720
cttttggcta atacggttag atatttgcaa ggaggaggaa gttggcgaga ggattggggt        780
cagttgtctg gtactgctgt gcctccgcag ggagctgagc ctcagtctaa cgctggacca        840
cgacctcaca tcggagatac gttatttacc ctattccgtg cgccggaatt attagcaccc        900
aacggtgatc tatacaacgt ctttgcgtgg gccttggacg tacttgcaaa gcgtctacgt        960
cctatgcatg tcttcatcct agactacgac cagtcgcccg cgggatgtcg agacgccttg       1020
ctacagttga cctcgggaat gattcagaca cacgtcacca ccccgggatc catacccact       1080
atttgtgact tagcaagaac atttgcccga gaaatgggtg aagctaac                    1128
```

<210> SEQ ID NO 13
<211> LENGTH: 1128
<212> TYPE: DNA
<213> ORGANISM: Artificial Sequence
<220> FEATURE:
<223> OTHER INFORMATION: Synthetic nucleotide sequence

<400> SEQUENCE: 13

```
atggcctcat atcctggtca tcaacacgct agtgccttcg accaggcggc gagatctcga         60
ggacattcga atagcgaac agcattacgt ccacgaagac aacaggaggc gacagaggtc        120
cgacctgaac agaaaatgcc tacactttg cgagtctaca tagatggtcc ccacggaatg        180
ggtaaaacta ccactaccca gttgttagtc gccttaggtt ctcgagacga tattgtctat        240
gtgcccgagc ccatgactta ctggcgagtc ctaggtgcat cggaaacgat agcgaacatc        300
tatacgacac agcatcgttt ggaccaggga gagatctcgg ccggtgacgc agcagtcgta        360
atgacaagtg ctcaaattac gatgggtatg ccttatgcgg taactgacgc agtcttggct        420
ccgcatatcg gtggagaggc cggatcgtca cacgctcccc ctccagcgtt aactctaatt        480
ttcgaccgac acccaattgc tcacctttta tgttaccccg cggcaagata tttaatggga        540
tcaatgaccc cgcaagctgt gttagctttt gtggcattga ttccgccaac cttacctgga        600
acgaatatag tccttggtgc attaccagag gatagacata ttgacagact tgctaagcga        660
cagcgaccgg gagagagatt ggacttagca atgttggcgg ccataagacg agtctacgga        720
cttttggcta atacggttag atatttgcaa ggaggaggaa gttggcgaga ggattggggt        780
cagttgtctg gtactgctgt gcctccgcag ggagctgagc ctcagtctaa cgctggacca        840
cgacctcaca tcggagatac gttatttacc ctattccgtg cgccggaatt attagcaccc        900
aacggtgatc tatacaacgt ctttgcgtgg gccttggacg tacttgcaaa gcgtctacgt        960
```

```
                                    -continued cctatgcatg tcttcatcct agactacgac cagtcgcccg cgggatgtcg agacgccttg    1020
ctacagttga cctcgggaat gattcagaca cacgtcacca ccccgggatc catacccact    1080
atttgtgact tagcaagaac atttgcccga gaaatgggtg aagctaac                 1128
```